US012077589B2

(12) United States Patent
Fu et al.

(10) Patent No.: US 12,077,589 B2
(45) Date of Patent: Sep. 3, 2024

(54) FUSION PROTEIN OF INTERFERON (IFN) AND ANTI-PD-L1 ANTIBODY AND USE THEREOF

(71) Applicant: INSTITUTE OF BIOPHYSICS CHINESE ACADEMY OF SCIENCES, Beijing (CN)

(72) Inventors: Yangxin Fu, Beijing (CN); Yong Liang, Beijing (CN); Hua Peng, Beijing (CN)

(73) Assignee: INSTITUTE OF BIOPHYSICS CHINESE ACADEMY OF SCIENCES, Beijing (CN)

( * ) Notice: Subject to any disclaimer, the term of this patent is extended or adjusted under 35 U.S.C. 154(b) by 877 days.

(21) Appl. No.: 17/048,106

(22) PCT Filed: Apr. 12, 2019

(86) PCT No.: PCT/CN2019/082360

§ 371 (c)(1),
(2) Date: Oct. 16, 2020

(87) PCT Pub. No.: WO2019/201161

PCT Pub. Date: Oct. 24, 2019

(65) Prior Publication Data

US 2021/0147548 A1 May 20, 2021

(30) Foreign Application Priority Data

Apr. 16, 2018 (CN) ........................ 201810336178.1

(51) Int. Cl.

| | |
|---|---|
| ***C07K 16/28*** | (2006.01) |
| ***A61K 38/21*** | (2006.01) |
| ***A61K 39/395*** | (2006.01) |
| ***A61K 47/68*** | (2017.01) |
| ***A61P 35/00*** | (2006.01) |
| ***C07K 14/555*** | (2006.01) |
| ***C07K 14/56*** | (2006.01) |
| ***C07K 14/565*** | (2006.01) |
| ***C07K 14/57*** | (2006.01) |

(52) U.S. Cl.

CPC .......... *C07K 16/2827* (2013.01); *A61K 38/21* (2013.01); *A61K 38/212* (2013.01); *A61K 38/215* (2013.01); *A61K 38/217* (2013.01); *A61K 39/3955* (2013.01); *A61K 47/6849* (2017.08); *A61P 35/00* (2018.01); *C07K 14/555* (2013.01); *C07K 14/56* (2013.01); *C07K 14/565* (2013.01); *C07K 14/57* (2013.01); *C07K 16/2818* (2013.01); *C07K 2317/21* (2013.01); *C07K 2317/24* (2013.01); *C07K 2317/54* (2013.01); *C07K 2317/55* (2013.01); *C07K 2317/569* (2013.01); *C07K 2317/622* (2013.01); *C07K 2319/30* (2013.01)

(58) Field of Classification Search

CPC combination set(s) only.
See application file for complete search history.

(56) References Cited

U.S. PATENT DOCUMENTS

| | | | | |
|---|---|---|---|---|
| 8,217,149 | B2 | 7/2012 | Irving et al. | |
| 10,471,124 | B2 * | 11/2019 | Xu | A61P 35/00 |
| 2002/0081664 | A1 * | 6/2002 | Lo | A61P 43/00 530/391.1 |
| 2018/0057594 | A1 * | 3/2018 | Evnin | C07K 16/3092 |

FOREIGN PATENT DOCUMENTS

| | | | |
|---|---|---|---|
| CN | 104403004 | A | 3/2015 |
| CN | 108727504 | A | 11/2018 |
| WO | 2017134302 | A2 | 8/2017 |

OTHER PUBLICATIONS

Strohl (BioDrugs. 29:215-239. (2015)) (Year: 2015).*

* cited by examiner

*Primary Examiner* — Jessica H Roark
*Assistant Examiner* — Francesca Edgingtongiordano
(74) *Attorney, Agent, or Firm* — Bayramoglu Law Offices LLC

(57) ABSTRACT

An IFN-anti-PD-L1 fusion protein, a pharmaceutical composition and a kit containing the same for treating tumors are disclosed. The IFN-anti-PD-L1 fusion protein of the present invention can simultaneously target PD-L1 and IFN receptors, and the activation of IFN signals in a tumor microenvironment (TME) can enhance the PD-1/PD-L1 therapy against tumors by inducing stronger T cell activation. The anti-PD-L1 antibody can be used to specifically deliver immunomodulatory molecules to tumor tissues, and the fusion protein results in the generation of multiple feedforward responses, which can increase the targeting effect, reduce the toxicity, and enhance the response to IFN therapy, thereby maximizing the anti-tumor effect.

11 Claims, 13 Drawing Sheets

Specification includes a Sequence Listing.

| Name | Mutation site and codon | Codon after mutation |
|---|---|---|
| Mouse IFNa4 (wt) | | |
| Mouse IFNa4 (L30A) | 30:CTG (leucine) | GCG (alanine) |
| Mouse IFNa4 (R144A) | 144:AGA (arginine) | GCA (alanine) |
| Mouse IFNa4 (A145G) | 145:GCA (alanine) | GGA (glycine) |
| Mouse IFNa4 (R149A) | 149:AGA (arginine) | GCA (alanine) |
| Mouse IFNa4 (S152A) | 152:TCT (serine) | GCA (alanine) |
| Human IFNa2 (Q124R) | | |

FIG. 11

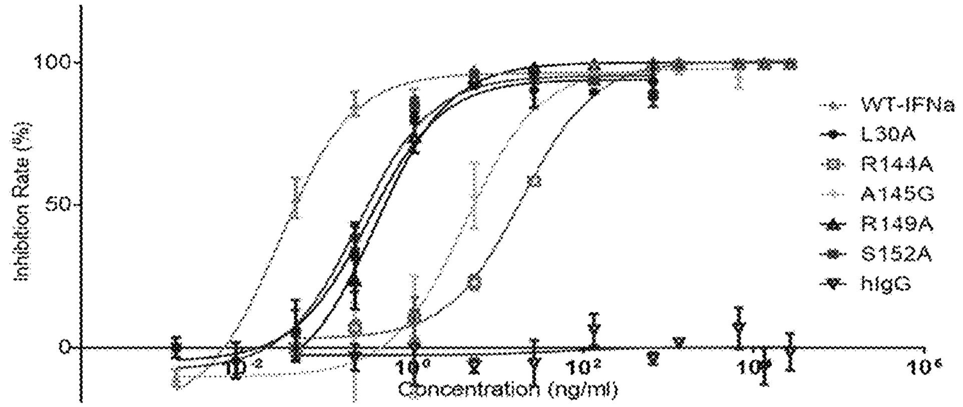

FIG. 12A

| Name | EC50 (ng/ml) | Relative activity |
|---|---|---|
| Mouse IFNa4 (wt) | 0.02616 | 1 |
| Mouse IFNa4 (L30A) | 0.2322 | 1/8.9 |
| Mouse IFNa4 (R144A) | 14.27 | 1/545.5 |
| Mouse IFNa4 (A145G) | 3.769 | 1/144.1 |
| Mouse IFNa4 (R149A) | 0.2864 | 1/10.9 |
| Mouse IFNa4 (S152A) | 0.1877 | 1/7.2 |

FIG. 12B

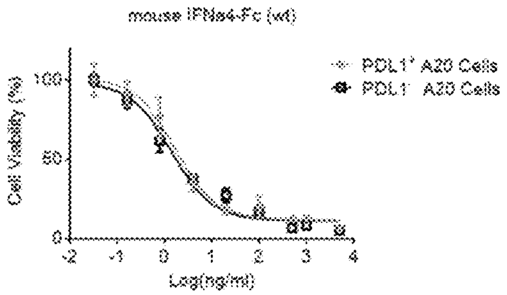
FIG. 13A
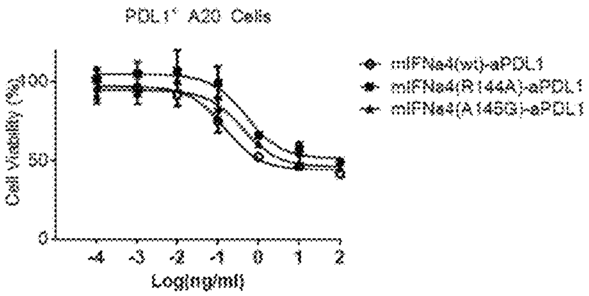
FIG. 13B
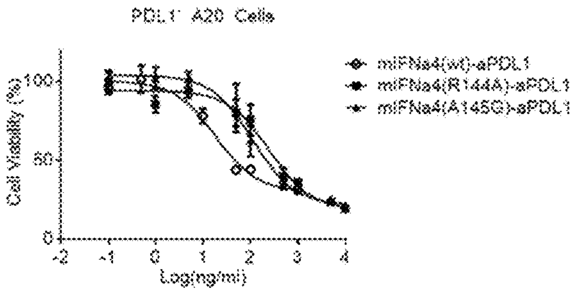
FIG. 13C
| | PDL1$^+$ A20 Cells | | PDL1$^-$ A20 Cells | | | |
|---|---|---|---|---|---|---|
| | EC50 | EC50 IFN/EC50 variant | EC50 | EC50 IFN/EC50 variant | Specificity index | Specificity index 2 |
| WT-mIFNa4-Fc | 1.689 | 1 | 1.423 | 1 | 1 | |
| mIFNa4(wt)-aPDL1 | 0.1393 | 12.12 | 9.473 | 0.150216 | 81 | 1 |
| mIFNa4(R144A)-aPDL1 | 0.5248 | 3.22 | 251.4 | 0.005660 | 569 | 7.0 |
| mIFNa4(A145G)-aPDL1 | 0.3714 | 4.55 | 383.5 | 0.003711 | 1,226 | 15.2 |
| mIFNa4(L30A)-aPDL1 | 4.552 | 0.37 | 1783 | 0.000798 | 465 | 5.8 |
| mIFNa4(R149A)-aPDL1 | 1.323 | 1.28 | 124.5 | 0.011430 | 112 | 1.4 |
| mIFNa4(S152A)-aPDL1 | 0.4274 | 3.95 | 5.013 | 0.283862 | 14 | 0.2 |
FIG. 13D

SEQUENCE LISTING

```
<160> NUMBER OF SEQ ID NOS: 48

<210> SEQ ID NO 1
<211> LENGTH: 472
<212> TYPE: PRT
<213> ORGANISM: Artificial Sequence
<220> FEATURE:
<223> OTHER INFORMATION: Amino acid sequence of Anti-PD-L1 (ScFvPD-L1)-
      Fc-knob) in heterodimer

<400> SEQUENCE: 1

Glu Leu Asp Ile Gln Met Thr Gln Ser Pro Ser Ser Leu Ser Ala Ser
1               5                   10                  15

Val Gly Asp Arg Val Thr Ile Thr Cys Arg Ala Ser Gln Asp Val Ser
            20                  25                  30

Thr Ala Val Ala Trp Tyr Gln Gln Lys Pro Gly Lys Ala Pro Lys Leu
        35                  40                  45

Leu Ile Tyr Ser Ala Ser Phe Leu Tyr Ser Gly Val Pro Ser Arg Phe
    50                  55                  60

Ser Gly Ser Gly Ser Gly Thr Asp Phe Thr Leu Thr Ile Ser Ser Leu
65                  70                  75                  80

Gln Pro Glu Asp Phe Ala Thr Tyr Tyr Cys Gln Gln Tyr Leu Tyr His
                85                  90                  95

Pro Ala Thr Phe Gly Gln Gly Thr Lys Val Glu Ile Lys Arg Gly Gly
            100                 105                 110

Gly Gly Ser Gly Gly Gly Gly Ser Gly Gly Gly Gly Ser Glu Val Gln
        115                 120                 125

Leu Val Glu Ser Gly Gly Gly Leu Val Gln Pro Gly Gly Ser Leu Arg
    130                 135                 140
```

Leu Ser Cys Ala Ala Ser Gly Phe Thr Phe Ser Asp Ser Trp Ile His
145 150 155 160

Trp Val Arg Gln Ala Pro Gly Lys Gly Leu Glu Trp Val Ala Trp Ile
165 170 175

Ser Pro Tyr Gly Gly Ser Thr Tyr Tyr Ala Asp Ser Val Lys Gly Arg
180 185 190

Phe Thr Ile Ser Ala Asp Thr Ser Lys Asn Thr Ala Tyr Leu Gln Met
195 200 205

Asn Ser Leu Arg Ala Glu Asp Thr Ala Val Tyr Tyr Cys Ala Arg Arg
210 215 220

His Trp Pro Gly Gly Phe Asp Tyr Trp Gly Gln Gly Thr Leu Val Thr
225 230 235 240

Val Ser Ala Arg Ser Asp Lys Thr His Thr Cys Pro Pro Cys Pro Ala
245 250 255

Pro Glu Leu Leu Gly Gly Pro Ser Val Phe Leu Phe Pro Pro Lys Pro
260 265 270

Lys Asp Thr Leu Met Ile Ser Arg Thr Pro Glu Val Thr Cys Val Val
275 280 285

Val Asp Val Ser His Glu Asp Pro Glu Val Lys Phe Asn Trp Tyr Val
290 295 300

Asp Gly Val Glu Val His Asn Ala Lys Thr Lys Pro Arg Glu Glu Gln
305 310 315 320

Tyr Asn Ser Thr Tyr Arg Val Val Ser Val Leu Thr Val Leu His Gln
325 330 335

Asp Trp Leu Asn Gly Lys Glu Tyr Lys Cys Lys Val Ser Asn Lys Ala
340 345 350

Leu Pro Ala Pro Ile Glu Lys Thr Ile Ser Lys Ala Lys Gly Gln Pro
355 360 365

Arg Glu Pro Gln Val Tyr Thr Leu Pro Pro Cys Arg Asp Glu Leu Thr
370 375 380

Lys Asn Gln Val Ser Leu Trp Cys Leu Val Lys Gly Phe Tyr Pro Ser
385 390 395 400

Asp Ile Ala Val Glu Trp Glu Ser Asn Gly Gln Pro Glu Asn Asn Tyr
405 410 415

Lys Thr Thr Pro Pro Val Leu Asp Ser Asp Gly Ser Phe Phe Leu Tyr
420 425 430

Ser Lys Leu Thr Val Asp Lys Ser Arg Trp Gln Gln Gly Asn Val Phe
435 440 445

Ser Cys Ser Val Met His Glu Ala Leu His Asn His Tyr Thr Gln Lys
450 455 460

Ser Leu Ser Leu Ser Pro Gly Lys
465 470

<210> SEQ ID NO 2
<211> LENGTH: 413
<212> TYPE: PRT
<213> ORGANISM: Artificial Sequence
<220> FEATURE:
<223> OTHER INFORMATION: Amino acid sequence of mIFNa4-Fc-hole in heterodimer

<400> SEQUENCE: 2

Cys Asp Leu Pro His Thr Tyr Asn Leu Gly Asn Lys Arg Ala Leu Thr
1 5 10 15

```
Val Leu Glu Glu Met Arg Arg Leu Pro Pro Leu Ser Cys Leu Lys Asp
            20                  25                  30

Arg Lys Asp Phe Gly Phe Pro Leu Glu Lys Val Asp Asn Gln Gln Ile
        35                  40                  45

Gln Lys Ala Gln Ala Ile Leu Val Leu Arg Asp Leu Thr Gln Gln Ile
    50                  55                  60

Leu Asn Leu Phe Thr Ser Lys Asp Leu Ser Ala Thr Trp Asn Ala Thr
65                  70                  75                  80

Leu Leu Asp Ser Phe Cys Asn Asp Leu His Gln Gln Leu Asn Asp Leu
                85                  90                  95

Lys Ala Cys Val Met Gln Glu Pro Pro Leu Thr Gln Glu Asp Ser Leu
            100                 105                 110

Leu Ala Val Arg Thr Tyr Phe His Arg Ile Thr Val Tyr Leu Arg Lys
        115                 120                 125

Lys Lys His Ser Leu Cys Ala Trp Glu Val Ile Arg Ala Glu Val Trp
    130                 135                 140

Arg Ala Leu Ser Ser Ser Thr Asn Leu Leu Ala Arg Leu Ser Glu Glu
145                 150                 155                 160

Lys Glu Ser Gly Gly Gly Gly Ser Gly Gly Gly Gly Ser Gly Gly Gly
                165                 170                 175

Gly Ser Gly Gly Gly Gly Arg Thr Asp Lys Thr His Thr Cys Pro Pro
            180                 185                 190

Cys Pro Ala Pro Glu Leu Leu Gly Gly Pro Ser Val Phe Leu Phe Pro
        195                 200                 205

Pro Lys Pro Lys Asp Thr Leu Met Ile Ser Arg Thr Pro Glu Val Thr
    210                 215                 220

Cys Val Val Val Asp Val Ser His Glu Asp Pro Glu Val Lys Phe Asn
225                 230                 235                 240

Trp Tyr Val Asp Gly Val Glu Val His Asn Ala Lys Thr Lys Pro Arg
                245                 250                 255

Glu Glu Gln Tyr Asn Ser Thr Tyr Arg Val Val Ser Val Leu Thr Val
            260                 265                 270

Leu His Gln Asp Trp Leu Asn Gly Lys Glu Tyr Lys Cys Lys Val Ser
        275                 280                 285

Asn Lys Ala Leu Pro Ala Pro Ile Glu Lys Thr Ile Ser Lys Ala Lys
    290                 295                 300

Gly Gln Pro Arg Glu Pro Gln Val Cys Thr Leu Pro Pro Ser Arg Asp
305                 310                 315                 320

Glu Leu Thr Lys Asn Gln Val Ser Leu Ser Cys Ala Val Lys Gly Phe
                325                 330                 335

Tyr Pro Ser Asp Ile Ala Val Glu Trp Glu Ser Asn Gly Gln Pro Glu
            340                 345                 350

Asn Asn Tyr Lys Thr Thr Pro Pro Val Leu Asp Ser Asp Gly Ser Phe
        355                 360                 365

Phe Leu Val Ser Lys Leu Thr Val Asp Lys Ser Arg Trp Gln Gln Gly
    370                 375                 380

Asn Val Phe Ser Cys Ser Val Met His Glu Ala Leu His Asn His Tyr
385                 390                 395                 400

Thr Gln Lys Ser Leu Ser Leu Ser Pro Gly Lys His Val
                405                 410
```

<210> SEQ ID NO 3
<211> LENGTH: 660

<212> TYPE: PRT
<213> ORGANISM: Artificial Sequence
<220> FEATURE:
<223> OTHER INFORMATION: Amino acid sequence of mIFNa4-anti-PD-L1-Fc in homodimer

<400> SEQUENCE: 3

```
Cys Asp Leu Pro His Thr Tyr Asn Leu Gly Asn Lys Arg Ala Leu Thr
1               5                   10                  15

Val Leu Glu Glu Met Arg Arg Leu Pro Pro Leu Ser Cys Leu Lys Asp
            20                  25                  30

Arg Lys Asp Phe Gly Phe Pro Leu Glu Lys Val Asp Asn Gln Gln Ile
        35                  40                  45

Gln Lys Ala Gln Ala Ile Leu Val Leu Arg Asp Leu Thr Gln Gln Ile
    50                  55                  60

Leu Asn Leu Phe Thr Ser Lys Asp Leu Ser Ala Thr Trp Asn Ala Thr
65                  70                  75                  80

Leu Leu Asp Ser Phe Cys Asn Asp Leu His Gln Gln Leu Asn Asp Leu
                85                  90                  95

Lys Ala Cys Val Met Gln Glu Pro Pro Leu Thr Gln Glu Asp Ser Leu
            100                 105                 110

Leu Ala Val Arg Thr Tyr Phe His Arg Ile Thr Val Tyr Leu Arg Lys
        115                 120                 125

Lys Lys His Ser Leu Cys Ala Trp Glu Val Ile Arg Ala Glu Val Trp
    130                 135                 140

Arg Ala Leu Ser Ser Ser Thr Asn Leu Leu Ala Arg Leu Ser Glu Glu
145                 150                 155                 160

Lys Glu Ser Gly Gly Gly Gly Ser Gly Gly Gly Gly Ser Gly Gly Gly
                165                 170                 175

Gly Ser Gly Gly Gly Gly Arg Thr Asp Ile Gln Met Thr Gln Ser Pro
            180                 185                 190

Ser Ser Leu Ser Ala Ser Val Gly Asp Arg Val Thr Ile Thr Cys Arg
        195                 200                 205

Ala Ser Gln Asp Val Ser Thr Ala Val Ala Trp Tyr Gln Gln Lys Pro
    210                 215                 220

Gly Lys Ala Pro Lys Leu Leu Ile Tyr Ser Ala Ser Phe Leu Tyr Ser
225                 230                 235                 240

Gly Val Pro Ser Arg Phe Ser Gly Ser Gly Ser Gly Thr Asp Phe Thr
                245                 250                 255

Leu Thr Ile Ser Ser Leu Gln Pro Glu Asp Phe Ala Thr Tyr Tyr Cys
            260                 265                 270

Gln Gln Tyr Leu Tyr His Pro Ala Thr Phe Gly Gln Gly Thr Lys Val
        275                 280                 285

Glu Ile Lys Arg Gly Gly Gly Gly Ser Gly Gly Gly Gly Ser Gly Gly
    290                 295                 300

Gly Gly Ser Glu Val Gln Leu Val Glu Ser Gly Gly Gly Leu Val Gln
305                 310                 315                 320

Pro Gly Gly Ser Leu Arg Leu Ser Cys Ala Ala Ser Gly Phe Thr Phe
                325                 330                 335

Ser Asp Ser Trp Ile His Trp Val Arg Gln Ala Pro Gly Lys Gly Leu
            340                 345                 350

Glu Trp Val Ala Trp Ile Ser Pro Tyr Gly Gly Ser Thr Tyr Tyr Ala
        355                 360                 365

Asp Ser Val Lys Gly Arg Phe Thr Ile Ser Ala Asp Thr Ser Lys Asn
    370                 375                 380
```

```
Thr Ala Tyr Leu Gln Met Asn Ser Leu Arg Ala Glu Asp Thr Ala Val
385                 390                 395                 400

Tyr Tyr Cys Ala Arg Arg His Trp Pro Gly Gly Phe Asp Tyr Trp Gly
                405                 410                 415

Gln Gly Thr Leu Val Thr Val Ser Ala Phe Glu Glu Pro Lys Ser Cys
            420                 425                 430

Asp Lys Thr His Thr Cys Pro Pro Cys Pro Ala Pro Glu Leu Leu Gly
        435                 440                 445

Gly Pro Ser Val Phe Leu Phe Pro Pro Lys Pro Lys Asp Gln Leu Met
    450                 455                 460

Ile Ser Arg Thr Pro Glu Val Thr Cys Val Val Val Asp Val Ser His
465                 470                 475                 480

Glu Asp Pro Glu Val Lys Phe Asn Trp Tyr Val Asp Gly Val Glu Val
                485                 490                 495

His Asn Ala Lys Thr Lys Pro Arg Glu Glu Gln Tyr Asn Ser Thr Tyr
            500                 505                 510

Arg Val Val Ser Val Leu Thr Val Leu His Gln Asp Trp Leu Asn Gly
        515                 520                 525

Lys Glu Tyr Lys Cys Lys Val Ser Asn Lys Ala Leu Pro Ala Pro Ile
    530                 535                 540

Glu Lys Thr Ile Ser Lys Ala Lys Gly Gln Pro Arg Glu Pro Gln Val
545                 550                 555                 560

Tyr Thr Leu Pro Pro Ser Arg Asp Glu Leu Thr Lys Asn Gln Val Ser
                565                 570                 575

Leu Thr Cys Leu Val Lys Gly Phe Tyr Pro Ser Asp Ile Ala Val Glu
            580                 585                 590

Trp Glu Ser Asn Gly Gln Pro Glu Asn Asn Tyr Lys Thr Thr Pro Pro
        595                 600                 605

Val Leu Asp Ser Asp Gly Ser Phe Leu Tyr Ser Lys Leu Thr Val Asp
    610                 615                 620

Lys Ser Arg Trp Gln Gln Gly Asn Val Phe Ser Cys Ser Val Leu His
625                 630                 635                 640

Glu Ala Leu His Asn His Tyr Thr Gln Lys Ser Leu Ser Leu Ser Pro
                645                 650                 655

Gly Lys His Val
            660
```

<210> SEQ ID NO 4
<211> LENGTH: 1482
<212> TYPE: DNA
<213> ORGANISM: Artificial Sequence
<220> FEATURE:
<223> OTHER INFORMATION: Anti-PD-L1-Fc-knob (coding nucleic acid sequence of Anti-PD-L1 in heterodimer)

<400> SEQUENCE: 4

```
atggagacag acacactcct gctatgggta ctgctgctct gggttccagg ttccactggt      60

gacgagctcg acatccagat gacccagagc cccagcagcc tgagcgccag cgtgggcgac     120

agagtgacca tcacctgcag agccagccag gacgtgagca ccgccgtggc ctggtaccag     180

cagaagcccg gcaaggcccc caagctgctg atctacagcg ccagcttcct gtacagcggc     240

gtgcccagca gattcagcgg cagcggcagc ggcaccgact tcaccctgac catcagcagc     300

ctgcagcccg aggacttcgc cacctactac tgccagcagt acctgtacca ccccgccacc     360

ttcggccagg gcaccaaggt ggagatcaag agaggcggcg gcggcagcgg cggcggcggc     420
```

```
agcggcggcg gcggcagcga ggtgcagctg gtggagagcg gcggcggcct ggtgcagccc    480

ggcggcagcc tgagactgag ctgcgccgcc agcggcttca ccttcagcga cagctggatc    540

cactgggtga gacaggcccc cggcaagggc ctggagtggg tggcctggat cagcccctac    600

ggcggcagca cctactacgc cgacagcgtg aagggcagat tcaccatcag cgccgacacc    660

agcaagaaca ccgcctacct gcagatgaac agcctgagag ccgaggacac cgccgtgtac    720

tactgcgcca gaagacactg gcccggcggc ttcgactact ggggccaggg caccctggtg    780

accgtgagcg ccagatctga caagacccac acctgccccc cctgccccgc ccccgagctg    840

ctgggcggcc ccagcgtgtt cctgttcccc cccaagccca aggacaccct gatgatcagc    900

cgcacccccg aggtgacctg cgtggtggtg gacgtgagcc acgaggaccc cgaggtgaag    960

ttcaactggt acgtggacgg cgtggaggtg cacaacgcca agaccaagcc ccgcgaggag   1020

cagtacaaca gcacctaccg cgtggtgagc gtgctgaccg tgctgcacca ggactggctg   1080

aacggcaagg agtacaagtg caaggtgagc aacaaggccc tgcccgcccc catcgagaag   1140

accatcagca aggccaaggg ccagccccgc gagccccagg tgtacaccct gccccccctgc   1200

cgcgacgagc tgaccaagaa ccaggtgagc ctgtggtgcc tggtgaaggg cttctacccc   1260

agcgacatcg ccgtggagtg ggagagcaac ggccagcccg agaacaacta caagaccacc   1320

ccccccgtgc tggacagcga cggcagcttc ttcctgtaca gcaagctgac cgtggacaag   1380

agccgctggc agcagggcaa cgtgttcagc tgcagcgtga tgcacgaggc cctgcacaac   1440

cactacaccc agaagagcct gagcctgagc cccggcaagt aa                      1482
```

<210> SEQ ID NO 5
<211> LENGTH: 1311
<212> TYPE: DNA
<213> ORGANISM: Artificial Sequence
<220> FEATURE:
<223> OTHER INFORMATION: mIFNa4-Fc-hole (coding nucleic acid sequence of mIFNa4-Fc in heterodimer)

<400> SEQUENCE: 5

```
gccgccacca tggagacaga cacactcctg ctatgggtac tgctgctctg ggttccaggt     60

tccactggtt cgcgatgtga cctgcctcac acttataacc tcgggaacaa gagggccttg    120

acagtcctgg aagaaatgag aagactcccc cctctttcct gcctgaagga caggaaggat    180

tttggattcc ccttggagaa ggtggataac caacagatcc agaaggctca agccatcctt    240

gtgctaagag atcttaccca gcagattttg aacctcttca catcaaaaga cttgtctgct    300

acttggaatg caactctact agactcattc tgcaatgacc tccatcagca gctcaatgac    360

ctcaaagcct gtgtgatgca ggaacctcct ctgacccagg aagactccct gctggctgtg    420

aggacatact tccacaggat cactgtgtac ctgagaaaga agaaacacag cctctgtgcc    480

tgggaggtga tcagagcaga agtctggaga gccctctctt cctcaaccaa cttgctggca    540

agactgagtg aggagaagga gagtggcggt ggtggctccg gcggtggtgg ctccggcggt    600

ggtggctccg gcggtggtgg ccgtacggac aagacccaca cctgcccccc ctgccccgcc    660

cccgagctgc tgggcggccc cagcgtgttc ctgttccccc ccaagcccaa ggacaccctg    720

atgatcagcc gcacccccga ggtgacctgc gtggtggtgg acgtgagcca cgaggacccc    780

gaggtgaagt tcaactggta cgtggacggc gtggaggtgc acaacgccaa gaccaagccc    840

cgcgaggagc agtacaacag cacctaccgc gtggtgagcg tgctgaccgt gctgcaccag    900

gactggctga acggcaagga gtacaagtgc aaggtgagca acaaggccct gcccgccccc    960
```

atcgagaaga ccatcagcaa ggccaagggc cagccccgcg agccccaggt gtgcaccctg 1020
ccccccagcc gcgacgagct gaccaagaac caggtgagcc tgagctgcgc cgtgaagggc 1080
ttctacccca gcgacatcgc cgtggagtgg gagagcaacg gccagcccga gaacaactac 1140
aagaccaccc cccccgtgct ggacagcgac ggcagcttct tcctggtgag caagctgacc 1200
gtggacaaga gccgctggca gcagggcaac gtgttcagct gcagcgtgat gcacgaggcc 1260
ctgcacaacc actacaccca gaagagcctg agcctgagcc ccggcaagta a 1311

<210> SEQ ID NO 6
<211> LENGTH: 2052
<212> TYPE: DNA
<213> ORGANISM: Artificial Sequence
<220> FEATURE:
<223> OTHER INFORMATION: mIFNa4-anti-PD-L1-Fc (coding nucleic acid sequence of mIFNa4-anti-PD-L1-Fc in homodimer)

<400> SEQUENCE: 6
atggagacag acacactcct gctatgggta ctgctgctct gggttccagg ttccactggt 60
tcgcgatgtg acctgcctca cacttataac ctcgggaaca agagggcctt gacagtcctg 120
gaagaaatga gaagactccc ccctctttcc tgcctgaagg acaggaagga ttttggattc 180
cccttggaga aggtggataa ccaacagatc cagaaggctc aagccatcct tgtgctaaga 240
gatcttaccc agcagatttt gaacctcttc acatcaaaag acttgtctgc tacttggaat 300
gcaactctac tagactcatt ctgcaatgac ctccatcagc agctcaatga cctcaaagcc 360
tgtgtgatgc aggaacctcc tctgacccag gaagactccc tgctggctgt gaggacatac 420
ttccacagga tcactgtgta cctgagaaag aagaaacaca gcctctgtgc ctgggaggtg 480
atcagagcag aagtctggag agccctctct tcctcaacca acttgctggc aagactgagt 540
gaggagaagg agagtggcgg tggtggctcc ggcggtggtg gctccggcgg tggtggctcc 600
ggcggtggtg gccgtacgga catccagatg acccagagcc ccagcagcct gagcgccagc 660
gtgggcgaca gagtgaccat cacctgcaga gccagccagg acgtgagcac cgccgtggcc 720
tggtaccagc agaagcccgg caaggccccc aagctgctga tctacagcgc cagcttcctg 780
tacagcggcg tgcccagcag attcagcggc agcggcagcg gcaccgactt caccctgacc 840
atcagcagcc tgcagcccga ggacttcgcc acctactact gccagcagta cctgtaccac 900
cccgccacct tcggccaggg caccaaggtg gagatcaaga gaggcggcgg cggcagcggc 960
ggcggcggca gcggcggcgg cggcagcgag gtgcagctgg tggagagcgg cggcggcctg 1020
gtgcagcccg gcggcagcct gagactgagc tgcgccgcca gcggcttcac cttcagcgac 1080
agctggatcc actgggtgag acaggccccc ggcaagggcc tggagtgggt ggcctggatc 1140
agcccctacg gcggcagcac ctactacgcc gacagcgtga agggcagatt caccatcagc 1200
gccgacacca gcaagaacac cgcctacctg cagatgaaca gcctgagagc cgaggacacc 1260
gccgtgtact actgcgccag aagacactgg cccggcggct tcgactactg gggccagggc 1320
accctggtga ccgtgagcgc cttcgaagag cccaagagct gcgacaagac ccacacctgt 1380 ccccccttgtc ctgcccctga gctgctgggc ggacccagcg tgttcctgtt cccccccaaag 1440 cccaaggacc agctgatgat cagccggacc cccgaagtga cctgcgtggt ggtggacgtg 1500
tcccacgagg accctgaagt gaagttcaat tggtacgtgg acggcgtgga ggtgcacaac 1560
gccaagacca agccccggga ggaacagtac aacagcacct accgggtggt gtccgtgctg 1620
accgtgctgc accaggactg gctgaacggc aaagagtaca agtgcaaggt ctccaacaag 1680

-continued gccctgcctg cccccatcga aaagaccatc agcaaggcca agggccagcc cagagaaccc 1740
caggtgtaca ccctgccccc cagcagagat gagctgacca agaaccaggt gtccctgacc 1800
tgcctggtca agggcttcta ccccagcgat atcgccgtgg agtgggagag caacggccag 1860
cctgagaaca actacaagac cacccccccct gtgctggaca gcgatggcag cttcctctac 1920
agcaaactga ccgtggacaa gagccggtgg cagcagggca acgtgttcag ctgcagcgtg 1980
ttgcacgagg ccctgcacaa ccactacacc cagaagtccc tgagcctgag ccccggcaaa 2040
cacgtgtagt aa 2052

<210> SEQ ID NO 7
<211> LENGTH: 1314
<212> TYPE: DNA
<213> ORGANISM: Artificial Sequence
<220> FEATURE:
<223> OTHER INFORMATION: mIFNb-Fc-hole (coding nucleic acid sequence of mIFNb-Fc in heterodimer)

<400> SEQUENCE: 7
aagcttgccg ccaccatgga gacagacaca ctcctgctat gggtactgct gctctgggtt 60
ccaggttcca ctggttcgcg aatcaactat aagcagctcc agctccaaga aaggacgaac 120
attcggaaat gtcaggagct cctggagcag ctgaatggaa agatcaacct cacctacagg 180
gcggacttca agatccctat ggagatgacg gagaagatgc agaagagtta cactgccttt 240
gccatccaag agatgctcca gaatgtcttt cttgtcttca gaaacaattt ctccagcact 300
gggtggaatg agactattgt tgtacgtctc ctggatgaac tccaccagca gacagtgttt 360
ctgaagacag tactagagga aaagcaagag gaaagattga cgtgggagat gtcctcaact 420
gctctccact tgaagagcta ttactggagg gtgcaaaggt accttaaact catgaagtac 480
aacagctacg cctggatggt ggtccgagca gagatcttca ggaactttct catcattcga 540
agacttacca gaaacttcca aaacagtggc ggtggtggct ccggcggtgg tggctccggc 600
ggtggtggct ccggcggtgg tggccgtacg gacaagaccc acacctgccc ccccctgcccc 660 gcccccgagc tgctgggcgg ccccagcgtg ttcctgttcc cccccaagcc caaggacacc 720
ctgatgatca gccgcacccc cgaggtgacc tgcgtggtgg tggacgtgag ccacgaggac 780
cccgaggtga agttcaactg gtacgtggac ggcgtggagg tgcacaacgc caagaccaag 840
ccccgcgagg agcagtacaa cagcacctac cgcgtggtga gcgtgctgac cgtgctgcac 900
caggactggc tgaacggcaa ggagtacaag tgcaaggtga gcaacaaggc cctgcccgcc 960
cccatcgaga agaccatcag caaggccaag ggccagcccc gcgagcccca ggtgtgcacc 1020
ctgcccccca gccgcgacga gctgaccaag aaccaggtga gcctgagctg cgccgtgaag 1080
ggcttctacc ccagcgacat cgccgtggag tgggagagca acggccagcc cgagaacaac 1140
tacaagacca cccccccgt gctggacagc gacggcagct tcttcctggt gagcaagctg 1200
accgtggaca agagccgctg gcagcagggc aacgtgttca gctgcagcgt gatgcacgag 1260
gccctgcaca accactacac ccagaagagc ctgagcctga gccccggcaa gtaa 1314

<210> SEQ ID NO 8
<211> LENGTH: 1326
<212> TYPE: DNA
<213> ORGANISM: Artificial Sequence
<220> FEATURE:
<223> OTHER INFORMATION: hIFNa2-Fc-hole (coding nucleic acid sequence of hIFN a2-Fc in heterodimer)

-continued

<400> SEQUENCE: 8
aagcttgccg ccaccatgga gacagacaca ctcctgctat gggtactgct gctctgggtt 60
ccaggttcca ctggttcgcg atgtgatctg cctcaaaccc acagcctggg tagcaggagg 120
accttgatgc tcctggcaca gatgaggaga atctctcttt tctcctgctt gaaggacaga 180
catgactttg gatttcccca ggaggagttt ggcaaccagt tccaaaaggc tgaaaccatc 240
cctgtcctcc atgagatgat ccagcagatc ttcaatctct tcagcacaaa ggactcatct 300
gctgcttggg atgagaccct cctagacaaa ttctacactg aactctacca gcagctgaat 360
gacctggaag cctgtgtgat acagggggtg ggggtgacag agactcccct gatgaaggag 420
gactccattc tggctgtgag gaaatacttc caaagaatca ctctctatct gaaagagaag 480
aaatacagcc cttgtgcctg ggaggttgtc agagcagaaa tcatgagatc tttttctttg 540
tcaacaaact tgcaagaaag tttaagaagt aaggaaagtg gcggtggtgg ctccggcggt 600
ggtggctccg gcggtggtgg ctccggcggt ggtggccgta cggacaagac ccacacctgc 660 ccccccctgcc ccgcccccga gctgctgggc ggccccagcg tgttcctgtt cccccccaag 720
cccaaggaca ccctgatgat cagccgcacc cccgaggtga cctgcgtggt ggtggacgtg 780
agccacgagg accccgaggt gaagttcaac tggtacgtgg acggcgtgga ggtgcacaac 840
gccaagacca agccccgcga ggagcagtac aacagcacct accgcgtggt gagcgtgctg 900
accgtgctgc accaggactg gctgaacggc aaggagtaca agtgcaaggt gagcaacaag 960
gccctgcccg cccccatcga gaagaccatc agcaaggcca agggccagcc ccgcgagccc 1020
caggtgtgca ccctgccccc cagccgcgac gagctgacca agaaccaggt gagcctgagc 1080
tgcgccgtga agggcttcta ccccagcgac atcgccgtgg agtgggagag caacggccag 1140
cccgagaaca actacaagac caccccccccc gtgctggaca gcgacggcag cttcttcctg 1200
gtgagcaagc tgaccgtgga caagagccgc tggcagcagg gcaacgtgtt cagctgcagc 1260
gtgatgcacg aggccctgca caaccactac acccagaaga gcctgagcct gagccccggc 1320
aagtaa 1326

<210> SEQ ID NO 9
<211> LENGTH: 1329
<212> TYPE: DNA
<213> ORGANISM: Artificial Sequence
<220> FEATURE:
<223> OTHER INFORMATION: hIFNb-Fc-hole (coding nucleic acid sequence of hIFNb-Fc in heterodimer)

<400> SEQUENCE: 9
aagcttgccg ccaccatgga gacagacaca ctcctgctat gggtactgct gctctgggtt 60
ccaggttcca ctggttcgcg aatgagctac aacttgcttg gattcctaca aagaagcagc 120
aattttcagt gtcagaagct cctgtggcaa ttgaatggga ggcttgaata ctgcctcaag 180
gacaggatga actttgacat ccctgaggag attaagcagc tgcagcagtt ccagaaggag 240
gacgccgcat tgaccatcta tgagatgctc cagaacatct ttgctatttt cagacaagat 300
tcatctagca ctggctggaa tgagactatt gttgagaacc tcctggctaa tgtctatcat 360
cagataaacc atctgaagac agtcctggaa gaaaaactgg agaaagaaga tttcaccagg 420
ggaaaactca tgagcagtct gcacctgaaa agatattatg ggaggattct gcattacctg 480
aaggccaagg agtacagtca ctgtgcctgg accatagtca gagtggaaat cctaaggaac 540
ttttacttca ttaacagact tacaggttac ctccgaaaca gtggcggtgg tggctccggc 600

-continued ggtggtggct ccggcggtgg tggctccggc ggtggtggcc gtacggacaa gacccacacc 660 tgcccccct gccccgcccc cgagctgctg ggcggcccca gcgtgttcct gttcccccc 720 aagcccaagg acaccctgat gatcagccgc acccccgagg tgacctgcgt ggtggtggac 780
gtgagccacg aggaccccga ggtgaagttc aactggtacg tggacggcgt ggaggtgcac 840
aacgccaaga ccaagccccg cgaggagcag tacaacagca cctaccgcgt ggtgagcgtg 900
ctgaccgtgc tgcaccagga ctggctgaac ggcaaggagt acaagtgcaa ggtgagcaac 960
aaggccctgc ccgcccccat cgagaagacc atcagcaagg ccaagggcca gccccgcgag 1020
ccccaggtgt gcaccctgcc ccccagccgc gacgagctga ccaagaacca ggtgagcctg 1080
agctgcgccg tgaagggctt ctaccccagc gacatcgccg tggagtggga gagcaacggc 1140
cagcccgaga acaactacaa gaccaccccc cccgtgctgg acagcgacgg cagcttcttc 1200
ctggtgagca agctgaccgt ggacaagagc cgctggcagc agggcaacgt gttcagctgc 1260
agcgtgatgc acgaggccct gcacaaccac tacacccaga agagcctgag cctgagcccc 1320
ggcaagtaa 1329

<210> SEQ ID NO 10
<211> LENGTH: 1224
<212> TYPE: DNA
<213> ORGANISM: Artificial Sequence
<220> FEATURE:
<223> OTHER INFORMATION: mIFNg-Fc-hole (coding nucleic acid sequence of mIFNg-Fc-hole in heterodimer)

<400> SEQUENCE: 10
aagcttgccg ccaccatgga gacagacaca ctcctgctat gggtactgct gctctgggtt 60
ccaggttcca ctggttcgcg acacggcaca gtcattgaaa gcctagaaag tctgaataac 120
tattttaact caagtggcat agatgtggaa gaaaagagtc tcttcttgga tatctggagg 180
aactggcaaa aggatggtga catgaaaatc ctgcagagcc agattatctc tttctacctc 240
agactctttg aagtcttgaa agacaatcag gccatcagca acaacataag cgtcattgaa 300
tcacacctga ttactacctt cttcagcaac agcaaggcga aaaaggatgc attcatgagt 360
attgccaagt ttgaggtcaa caacccacag gtccagcgcc aagcattcaa tgagctcatc 420
cgagtggtcc accagctgtt gccggaatcc agcctcagga agcggaaaag gagtcgctgc 480
agtggcggtg gtggctccgg cggtggtggc tccggcggtg gtggctccgg cggtggtggc 540
gacaagaccc acacctgccc cccctgcccc gcccccgagc tgctgggcgg ccccagcgtg 600
ttcctgttcc cccccaagcc caaggacacc ctgatgatca gccgcacccc cgaggtgacc 660
tgcgtggtgg tggacgtgag ccacgaggac cccgaggtga agttcaactg gtacgtggac 720
ggcgtggagg tgcacaacgc caagaccaag ccccgcgagg agcagtacaa cagcacctac 780
cgcgtggtga gcgtgctgac cgtgctgcac caggactggc tgaacggcaa ggagtacaag 840
tgcaaggtga gcaacaaggc cctgcccgcc cccatcgaga agaccatcag caaggccaag 900
ggccagcccc gcgagcccca ggtgtgcacc ctgcccccca gccgcgacga gctgaccaag 960
aaccaggtga gcctgagctg cgccgtgaag ggcttctacc ccagcgacat cgccgtggag 1020
tgggagagca acggccagcc cgagaacaac tacaagacca cccccccgt gctggacagc 1080 gacggcagct tcttcctggt gagcaagctg accgtggaca agagccgctg gcagcagggc 1140
aacgtgttca gctgcagcgt gatgcacgag gccctgcaca accactacac ccagaagagc 1200
ctgagcctga gccccggcaa gtaa 1224

<210> SEQ ID NO 11
<211> LENGTH: 241
<212> TYPE: PRT
<213> ORGANISM: Artificial Sequence
<220> FEATURE:
<223> OTHER INFORMATION: Amino acid sequence of ScFv (PD-L1)

<400> SEQUENCE: 11

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Ser Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Leu Tyr His Pro Ala
                85                  90                  95

Thr Phe Gly Gln Gly Thr Lys Val Glu Ile Lys Arg Gly Gly Gly Gly
            100                 105                 110

Ser Gly Gly Gly Gly Ser Gly Gly Gly Gly Ser Glu Val Gln Leu Val
        115                 120                 125

Glu Ser Gly Gly Gly Leu Val Gln Pro Gly Gly Ser Leu Arg Leu Ser
    130                 135                 140

Cys Ala Ala Ser Gly Phe Thr Phe Ser Asp Ser Trp Ile His Trp Val
145                 150                 155                 160

Arg Gln Ala Pro Gly Lys Gly Leu Glu Trp Val Ala Trp Ile Ser Pro
                165                 170                 175

Tyr Gly Gly Ser Thr Tyr Tyr Ala Asp Ser Val Lys Gly Arg Phe Thr
            180                 185                 190

Ile Ser Ala Asp Thr Ser Lys Asn Thr Ala Tyr Leu Gln Met Asn Ser
        195                 200                 205

Leu Arg Ala Glu Asp Thr Ala Val Tyr Tyr Cys Ala Arg Arg His Trp
    210                 215                 220

Pro Gly Gly Phe Asp Tyr Trp Gly Gln Gly Thr Leu Val Thr Val Ser
225                 230                 235                 240

Ala
```

<210> SEQ ID NO 12
<211> LENGTH: 723
<212> TYPE: DNA
<213> ORGANISM: Artificial Sequence
<220> FEATURE:
<223> OTHER INFORMATION: Coding nucleic acid sequence of ScFv (PD-L1)

<400> SEQUENCE: 12

```
gacatccaga tgacccagag ccccagcagc ctgagcgcca gcgtgggcga cagagtgacc      60

atcacctgca gagccagcca ggacgtgagc accgccgtgg cctggtacca gcagaagccc     120

ggcaaggccc ccaagctgct gatctacagc gccagcttcc tgtacagcgg cgtgcccagc     180

agattcagcg gcagcggcag cggcaccgac ttcaccctga ccatcagcag cctgcagccc     240

gaggacttcg ccacctacta ctgccagcag tacctgtacc accccgccac cttcggccag     300

ggcaccaagg tggagatcaa gagaggcggc ggcggcagcg gcggcggcgg cagcggcggc     360
```

```
ggcggcagcg aggtgcagct ggtggagagc ggcggcggcc tggtgcagcc cggcggcagc    420

ctgagactga gctgcgccgc cagcggcttc accttcagcg acagctggat ccactgggtg    480

agacaggccc ccggcaaggg cctggagtgg gtggcctgga tcagccccta cggcggcagc    540

acctactacg ccgacagcgt gaagggcaga ttcaccatca gcgccgacac cagcaagaac    600

accgcctacc tgcagatgaa cagcctgaga gccgaggaca ccgccgtgta ctactgcgcc    660

agaagacact ggcccggcgg cttcgactac tggggccagg gcaccctggt gaccgtgagc    720

gcc                                                                   723
```

<210> SEQ ID NO 13
<211> LENGTH: 162
<212> TYPE: PRT
<213> ORGANISM: Artificial Sequence
<220> FEATURE:
<223> OTHER INFORMATION: Amino acid sequence of mIFN-a4

<400> SEQUENCE: 13

```
Cys Asp Leu Pro His Thr Tyr Asn Leu Gly Asn Lys Arg Ala Leu Thr
1               5                   10                  15

Val Leu Glu Glu Met Arg Arg Leu Pro Pro Leu Ser Cys Leu Lys Asp
            20                  25                  30

Arg Lys Asp Phe Gly Phe Pro Leu Glu Lys Val Asp Asn Gln Gln Ile
        35                  40                  45

Gln Lys Ala Gln Ala Ile Leu Val Leu Arg Asp Leu Thr Gln Gln Ile
    50                  55                  60

Leu Asn Leu Phe Thr Ser Lys Asp Leu Ser Ala Thr Trp Asn Ala Thr
65                  70                  75                  80

Leu Leu Asp Ser Phe Cys Asn Asp Leu His Gln Gln Leu Asn Asp Leu
                85                  90                  95

Lys Ala Cys Val Met Gln Glu Pro Pro Leu Thr Gln Glu Asp Ser Leu
            100                 105                 110

Leu Ala Val Arg Thr Tyr Phe His Arg Ile Thr Val Tyr Leu Arg Lys
        115                 120                 125

Lys Lys His Ser Leu Cys Ala Trp Glu Val Ile Arg Ala Glu Val Trp
    130                 135                 140

Arg Ala Leu Ser Ser Ser Thr Asn Leu Leu Ala Arg Leu Ser Glu Glu
145                 150                 155                 160

Lys Glu
```

<210> SEQ ID NO 14
<211> LENGTH: 486
<212> TYPE: DNA
<213> ORGANISM: Artificial Sequence
<220> FEATURE:
<223> OTHER INFORMATION: Coding nucleic acid sequence of mIFN-a4

<400> SEQUENCE: 14

```
tgtgacctgc ctcacactta taacctcggg aacaagaggg ccttgacagt cctggaagaa     60

atgagaagac tcccccctct ttcctgcctg aaggacagga aggattttgg attccccttg    120

gagaaggtgg ataaccaaca gatccagaag gctcaagcca tccttgtgct aagagatctt    180

acccagcaga ttttgaacct cttcacatca aaagacttgt ctgctacttg gaatgcaact    240

ctactagact cattctgcaa tgacctccat cagcagctca atgacctcaa agcctgtgtg    300

atgcaggaac ctcctctgac ccaggaagac tccctgctgg ctgtgaggac atacttccac    360

aggatcactg tgtacctgag aaagaagaaa cacagcctct gtgcctggga ggtgatcaga    420
```

gcagaagtct ggagagccct ctcttcctca accaacttgc tggcaagact gagtgaggag 480
aaggag 486

<210> SEQ ID NO 15
<211> LENGTH: 233
<212> TYPE: PRT
<213> ORGANISM: Artificial Sequence
<220> FEATURE:
<223> OTHER INFORMATION: Amino acid sequence of IgG1-Fc

<400> SEQUENCE: 15

Glu Pro Lys Ser Cys Asp Lys Thr His Thr Cys Pro Pro Cys Pro Ala
1 5 10 15

Pro Glu Leu Leu Gly Gly Pro Ser Val Phe Leu Phe Pro Pro Lys Pro
20 25 30

Lys Asp Gln Leu Met Ile Ser Arg Thr Pro Glu Val Thr Cys Val Val
35 40 45

Val Asp Val Ser His Glu Asp Pro Glu Val Lys Phe Asn Trp Tyr Val
50 55 60

Asp Gly Val Glu Val His Asn Ala Lys Thr Lys Pro Arg Glu Glu Gln
65 70 75 80

Tyr Asn Ser Thr Tyr Arg Val Val Ser Val Leu Thr Val Leu His Gln
85 90 95

Asp Trp Leu Asn Gly Lys Glu Tyr Lys Cys Lys Val Ser Asn Lys Ala
100 105 110

Leu Pro Ala Pro Ile Glu Lys Thr Ile Ser Lys Ala Lys Gly Gln Pro
115 120 125

Arg Glu Pro Gln Val Tyr Thr Leu Pro Pro Ser Arg Asp Glu Leu Thr
130 135 140

Lys Asn Gln Val Ser Leu Thr Cys Leu Val Lys Gly Phe Tyr Pro Ser
145 150 155 160

Asp Ile Ala Val Glu Trp Glu Ser Asn Gly Gln Pro Glu Asn Asn Tyr
165 170 175

Lys Thr Thr Pro Pro Val Leu Asp Ser Asp Gly Ser Phe Leu Tyr Ser
180 185 190

Lys Leu Thr Val Asp Lys Ser Arg Trp Gln Gln Gly Asn Val Phe Ser
195 200 205

Cys Ser Val Leu His Glu Ala Leu His Asn His Tyr Thr Gln Lys Ser
210 215 220

Leu Ser Leu Ser Pro Gly Lys His Val
225 230

<210> SEQ ID NO 16
<211> LENGTH: 699
<212> TYPE: DNA
<213> ORGANISM: Artificial Sequence
<220> FEATURE:
<223> OTHER INFORMATION: Coding nucleic acid sequence of IgG1- Fc

<400> SEQUENCE: 16
gagcccaaga gctgcgacaa gacccacacc tgtccccctt gtcctgcccc tgagctgctg 60
ggcggaccca gcgtgttcct gttcccccca aagcccaagg accagctgat gatcagccgg 120
acccccgaag tgacctgcgt ggtggtggac gtgtcccacg aggaccctga agtgaagttc 180
aattggtacg tggacggcgt ggaggtgcac aacgccaaga ccaagccccg ggaggaacag 240
tacaacagca cctaccgggt ggtgtccgtg ctgaccgtgc tgcaccagga ctggctgaac 300
ggcaaagagt acaagtgcaa ggtctccaac aaggccctgc ctgcccccat cgaaaagacc 360
atcagcaagg ccaagggcca gcccagagaa ccccaggtgt acaccctgcc ccccagcaga 420
gatgagctga ccaagaacca ggtgtccctg acctgcctgg tcaagggctt ctaccccagc 480
gatatcgccg tggagtggga gagcaacggc cagcctgaga acaactacaa gaccaccccc 540
cctgtgctgg acagcgatgg cagcttcctc tacagcaaac tgaccgtgga caagagccgg 600
tggcagcagg gcaacgtgtt cagctgcagc gtgttgcacg aggccctgca caaccactac 660
acccagaagt ccctgagcct gagccccggc aaacacgtg 699

<210> SEQ ID NO 17
<211> LENGTH: 161
<212> TYPE: PRT
<213> ORGANISM: Artificial Sequence
<220> FEATURE:
<223> OTHER INFORMATION: Amino acid sequence of mIFNb

<400> SEQUENCE: 17

Ile Asn Tyr Lys Gln Leu Gln Leu Gln Glu Arg Thr Asn Ile Arg Lys
1               5                   10                  15

Cys Gln Glu Leu Leu Glu Gln Leu Asn Gly Lys Ile Asn Leu Thr Tyr
            20                  25                  30

Arg Ala Asp Phe Lys Ile Pro Met Glu Met Thr Glu Lys Met Gln Lys
        35                  40                  45

Ser Tyr Thr Ala Phe Ala Ile Gln Glu Met Leu Gln Asn Val Phe Leu
    50                  55                  60

Val Phe Arg Asn Asn Phe Ser Ser Thr Gly Trp Asn Glu Thr Ile Val
65                  70                  75                  80

Val Arg Leu Leu Asp Glu Leu His Gln Gln Thr Val Phe Leu Lys Thr
                85                  90                  95

Val Leu Glu Glu Lys Gln Glu Glu Arg Leu Thr Trp Glu Met Ser Ser
            100                 105                 110

Thr Ala Leu His Leu Lys Ser Tyr Tyr Trp Arg Val Gln Arg Tyr Leu
        115                 120                 125

Lys Leu Met Lys Tyr Asn Ser Tyr Ala Trp Met Val Val Arg Ala Glu
    130                 135                 140

Ile Phe Arg Asn Phe Leu Ile Ile Arg Arg Leu Thr Arg Asn Phe Gln
145                 150                 155                 160

Asn

<210> SEQ ID NO 18
<211> LENGTH: 483
<212> TYPE: DNA
<213> ORGANISM: Artificial Sequence
<220> FEATURE:
<223> OTHER INFORMATION: Coding nucleic acid sequence of mIFNb

<400> SEQUENCE: 18
atcaactata agcagctcca gctccaagaa aggacgaaca ttcggaaatg tcaggagctc 60
ctggagcagc tgaatggaaa gatcaacctc acctacaggg cggacttcaa gatccctatg 120
gagatgacgg agaagatgca gaagagttac actgcctttg ccatccaaga gatgctccag 180
aatgtctttc ttgtcttcag aaacaatttc tccagcactg ggtggaatga gactattgtt 240
gtacgtctcc tggatgaact ccaccagcag acagtgtttc tgaagacagt actagaggaa 300
aagcaagagg aaagattgac gtgggagatg tcctcaactg ctctccactt gaagagctat 360

-continued tactggaggg tgcaaaggta ccttaaactc atgaagtaca acagctacgc ctggatggtg 420
gtccgagcag agatcttcag gaactttctc atcattcgaa gacttaccag aaacttccaa 480
aac 483

<210> SEQ ID NO 19
<211> LENGTH: 165
<212> TYPE: PRT
<213> ORGANISM: Artificial Sequence
<220> FEATURE:
<223> OTHER INFORMATION: Amino acid sequence of hIFNa2

<400> SEQUENCE: 19

Cys Asp Leu Pro Gln Thr His Ser Leu Gly Ser Arg Arg Thr Leu Met
1 5 10 15

Leu Leu Ala Gln Met Arg Arg Ile Ser Leu Phe Ser Cys Leu Lys Asp
20 25 30

Arg His Asp Phe Gly Phe Pro Gln Glu Glu Phe Gly Asn Gln Phe Gln
35 40 45

Lys Ala Glu Thr Ile Pro Val Leu His Glu Met Ile Gln Gln Ile Phe
50 55 60

Asn Leu Phe Ser Thr Lys Asp Ser Ser Ala Ala Trp Asp Glu Thr Leu
65 70 75 80

Leu Asp Lys Phe Tyr Thr Glu Leu Tyr Gln Gln Leu Asn Asp Leu Glu
85 90 95

Ala Cys Val Ile Gln Gly Val Gly Val Thr Glu Thr Pro Leu Met Lys
100 105 110

Glu Asp Ser Ile Leu Ala Val Arg Lys Tyr Phe Gln Arg Ile Thr Leu
115 120 125

Tyr Leu Lys Glu Lys Lys Tyr Ser Pro Cys Ala Trp Glu Val Val Arg
130 135 140

Ala Glu Ile Met Arg Ser Phe Ser Leu Ser Thr Asn Leu Gln Glu Ser
145 150 155 160

Leu Arg Ser Lys Glu
165

<210> SEQ ID NO 20
<211> LENGTH: 495
<212> TYPE: DNA
<213> ORGANISM: Artificial Sequence
<220> FEATURE:
<223> OTHER INFORMATION: Coding nucleic acid sequence of hIFNa2

<400> SEQUENCE: 20
tgtgatctgc ctcaaaccca cagcctgggt agcaggagga ccttgatgct cctggcacag 60
atgaggagaa tctctctttt ctcctgcttg aaggacagac atgactttgg atttccccag 120
gaggagtttg gcaaccagtt ccaaaaggct gaaaccatcc ctgtcctcca tgagatgatc 180
cagcagatct tcaatctctt cagcacaaag gactcatctg ctgcttggga tgagaccctc 240
ctagacaaat tctacactga actctaccag cagctgaatg acctggaagc ctgtgtgata 300
cagggggtgg gggtgacaga gactcccctg atgaaggagg actccattct ggctgtgagg 360
aaatacttcc aaagaatcac tctctatctg aaagagaaga aatacagccc ttgtgcctgg 420
gaggttgtca gagcagaaat catgagatct ttttctttgt caacaaactt gcaagaaagt 480
ttaagaagta aggaa 495

<210> SEQ ID NO 21

<211> LENGTH: 166
<212> TYPE: PRT
<213> ORGANISM: Artificial Sequence
<220> FEATURE:
<223> OTHER INFORMATION: Amino acid sequence of hIFNb

<400> SEQUENCE: 21

Met Ser Tyr Asn Leu Leu Gly Phe Leu Gln Arg Ser Ser Asn Phe Gln
1 5 10 15

Cys Gln Lys Leu Leu Trp Gln Leu Asn Gly Arg Leu Glu Tyr Cys Leu
20 25 30

Lys Asp Arg Met Asn Phe Asp Ile Pro Glu Glu Ile Lys Gln Leu Gln
35 40 45

Gln Phe Gln Lys Glu Asp Ala Ala Leu Thr Ile Tyr Glu Met Leu Gln
50 55 60

Asn Ile Phe Ala Ile Phe Arg Gln Asp Ser Ser Ser Thr Gly Trp Asn
65 70 75 80

Glu Thr Ile Val Glu Asn Leu Leu Ala Asn Val Tyr His Gln Ile Asn
85 90 95

His Leu Lys Thr Val Leu Glu Glu Lys Leu Glu Lys Glu Asp Phe Thr
100 105 110

Arg Gly Lys Leu Met Ser Ser Leu His Leu Lys Arg Tyr Tyr Gly Arg
115 120 125

Ile Leu His Tyr Leu Lys Ala Lys Glu Tyr Ser His Cys Ala Trp Thr
130 135 140

Ile Val Arg Val Glu Ile Leu Arg Asn Phe Tyr Phe Ile Asn Arg Leu
145 150 155 160

Thr Gly Tyr Leu Arg Asn
165

<210> SEQ ID NO 22
<211> LENGTH: 498
<212> TYPE: DNA
<213> ORGANISM: Artificial Sequence
<220> FEATURE:
<223> OTHER INFORMATION: Coding nucleic acid sequence of hIFNb

<400> SEQUENCE: 22
atgagctaca acttgcttgg attcctacaa agaagcagca attttcagtg tcagaagctc 60
ctgtggcaat tgaatgggag gcttgaatac tgcctcaagg acaggatgaa ctttgacatc 120
cctgaggaga ttaagcagct gcagcagttc cagaaggagg acgccgcatt gaccatctat 180
gagatgctcc agaacatctt tgctattttc agacaagatt catctagcac tggctggaat 240
gagactattg ttgagaacct cctggctaat gtctatcatc agataaacca tctgaagaca 300
gtcctggaag aaaaactgga gaaagaagat ttcaccaggg gaaaactcat gagcagtctg 360
cacctgaaaa gatattatgg gaggattctg cattacctga aggccaagga gtacagtcac 420
tgtgcctgga ccatagtcag agtggaaatc ctaaggaact tttacttcat taacagactt 480
acaggttacc tccgaaac 498

<210> SEQ ID NO 23
<211> LENGTH: 133
<212> TYPE: PRT
<213> ORGANISM: Artificial Sequence
<220> FEATURE:
<223> OTHER INFORMATION: Amino acid sequence of mIFNg

<400> SEQUENCE: 23

His Gly Thr Val Ile Glu Ser Leu Glu Ser Leu Asn Asn Tyr Phe Asn
1               5                   10                  15

Ser Ser Gly Ile Asp Val Glu Glu Lys Ser Leu Phe Leu Asp Ile Trp
            20                  25                  30

Arg Asn Trp Gln Lys Asp Gly Asp Met Lys Ile Leu Gln Ser Gln Ile
        35                  40                  45

Ile Ser Phe Tyr Leu Arg Leu Phe Glu Val Leu Lys Asp Asn Gln Ala
    50                  55                  60

Ile Ser Asn Asn Ile Ser Val Ile Glu Ser His Leu Ile Thr Thr Phe
65                  70                  75                  80

Phe Ser Asn Ser Lys Ala Lys Lys Asp Ala Phe Met Ser Ile Ala Lys
                85                  90                  95

Phe Glu Val Asn Asn Pro Gln Val Gln Arg Gln Ala Phe Asn Glu Leu
            100                 105                 110

Ile Arg Val Val His Gln Leu Leu Pro Glu Ser Ser Leu Arg Lys Arg
        115                 120                 125

Lys Arg Ser Arg Cys
    130

<210> SEQ ID NO 24
<211> LENGTH: 399
<212> TYPE: DNA
<213> ORGANISM: Artificial Sequence
<220> FEATURE:
<223> OTHER INFORMATION: Coding nucleic acid sequence of mIFNg

<400> SEQUENCE: 24
cacggcacag tcattgaaag cctagaaagt ctgaataact attttaactc aagtggcata 60
gatgtggaag aaaagagtct cttcttggat atctggagga actggcaaaa ggatggtgac 120
atgaaaatcc tgcagagcca gattatctct ttctacctca gactctttga agtcttgaaa 180
gacaatcagg ccatcagcaa caacataagc gtcattgaat cacacctgat tactaccttc 240
ttcagcaaca gcaaggcgaa aaaggatgca ttcatgagta ttgccaagtt tgaggtcaac 300
aacccacagg tccagcgcca agcattcaat gagctcatcc gagtggtcca ccagctgttg 360
ccggaatcca gcctcaggaa gcggaaaagg agtcgctgc 399

<210> SEQ ID NO 25
<211> LENGTH: 162
<212> TYPE: PRT
<213> ORGANISM: Artificial Sequence
<220> FEATURE:
<223> OTHER INFORMATION: Amino acid sequence of Mouse IFNa4(L30A)

<400> SEQUENCE: 25

Cys Asp Leu Pro His Thr Tyr Asn Leu Gly Asn Lys Arg Ala Leu Thr
1               5                   10                  15

Val Leu Glu Glu Met Arg Arg Leu Pro Pro Leu Ser Cys Ala Lys Asp
            20                  25                  30

Arg Lys Asp Phe Gly Phe Pro Leu Glu Lys Val Asp Asn Gln Gln Ile
        35                  40                  45

Gln Lys Ala Gln Ala Ile Leu Val Leu Arg Asp Leu Thr Gln Gln Ile
    50                  55                  60

Leu Asn Leu Phe Thr Ser Lys Asp Leu Ser Ala Thr Trp Asn Ala Thr
65                  70                  75                  80

-continued

```
Leu Leu Asp Ser Phe Cys Asn Asp Leu His Gln Gln Leu Asn Asp Leu
                85                  90                  95

Lys Ala Cys Val Met Gln Glu Pro Pro Leu Thr Gln Glu Asp Ser Leu
            100                 105                 110

Leu Ala Val Arg Thr Tyr Phe His Arg Ile Thr Val Tyr Leu Arg Lys
        115                 120                 125

Lys Lys His Ser Leu Cys Ala Trp Glu Val Ile Arg Ala Glu Val Trp
    130                 135                 140

Arg Ala Leu Ser Ser Ser Thr Asn Leu Leu Ala Arg Leu Ser Glu Glu
145                 150                 155                 160

Lys Glu


<210> SEQ ID NO 26
<211> LENGTH: 486
<212> TYPE: DNA
<213> ORGANISM: Artificial Sequence
<220> FEATURE:
<223> OTHER INFORMATION: Coding nucleic acid sequence of Mouse
      IFNa4(L30A)

<400> SEQUENCE: 26

tgtgacctgc ctcacactta taacctcggg aacaagaggg ccttgacagt cctggaagaa      60

atgagaagac tccccctct ttcctgcgcg aaggacagga aggattttgg attcccttg    120

gagaaggtgg ataaccaaca gatccagaag gctcaagcca tccttgtgct aagagatctt    180

acccagcaga ttttgaacct cttcacatca aaagacttgt ctgctacttg gaatgcaact    240

ctcctagact cattctgcaa tgacctccat cagcagctca atgatctcaa agcctgtgtg    300

atgcaggaac ctcctctgac ccaggaagac tccctgctgg ctgtgaggac atacttccac    360

aggatcactg tgtacctgag aaagaagaaa cacagcctct gtgcctggga ggtgatcaga    420

gcagaagtct ggagagccct ctcttcctca accaacttgc tggcaagact gagtgaggag    480

aaggag                                                                486


<210> SEQ ID NO 27
<211> LENGTH: 162
<212> TYPE: PRT
<213> ORGANISM: Artificial Sequence
<220> FEATURE:
<223> OTHER INFORMATION: Amino acid sequence of Mouse IFNa4(R144A)

<400> SEQUENCE: 27

Cys Asp Leu Pro His Thr Tyr Asn Leu Gly Asn Lys Arg Ala Leu Thr
1               5                   10                  15

Val Leu Glu Glu Met Arg Arg Leu Pro Pro Leu Ser Cys Leu Lys Asp
            20                  25                  30

Arg Lys Asp Phe Gly Phe Pro Leu Glu Lys Val Asp Asn Gln Gln Ile
        35                  40                  45

Gln Lys Ala Gln Ala Ile Leu Val Leu Arg Asp Leu Thr Gln Gln Ile
    50                  55                  60

Leu Asn Leu Phe Thr Ser Lys Asp Leu Ser Ala Thr Trp Asn Ala Thr
65                  70                  75                  80

Leu Leu Asp Ser Phe Cys Asn Asp Leu His Gln Gln Leu Asn Asp Leu
                85                  90                  95

Lys Ala Cys Val Met Gln Glu Pro Pro Leu Thr Gln Glu Asp Ser Leu
            100                 105                 110

Leu Ala Val Arg Thr Tyr Phe His Arg Ile Thr Val Tyr Leu Arg Lys
        115                 120                 125
```

```
Lys Lys His Ser Leu Cys Ala Trp Glu Val Ile Ala Ala Glu Val Trp
    130                 135                 140

Arg Ala Leu Ser Ser Ser Thr Asn Leu Leu Ala Arg Leu Ser Glu Glu
145                 150                 155                 160

Lys Glu


<210> SEQ ID NO 28
<211> LENGTH: 486
<212> TYPE: DNA
<213> ORGANISM: Artificial Sequence
<220> FEATURE:
<223> OTHER INFORMATION: Coding nucleic acid sequence of Mouse
      IFNa4(R144A)

<400> SEQUENCE: 28

tgtgacctgc ctcacactta taacctcggg aacaagaggg ccttgacagt cctggaagaa     60

atgagaagac tcccccctct ttcctgcctg aaggacagga aggattttgg attccccttg    120

gagaaggtgg ataaccaaca gatccagaag gctcaagcca tccttgtgct aagagatctt    180

acccagcaga ttttgaacct cttcacatca aaagacttgt ctgctacttg gaatgcaact    240

ctcctagact cattctgcaa tgacctccat cagcagctca atgatctcaa agcctgtgtg    300

atgcaggaac ctcctctgac ccaggaagac tccctgctgg ctgtgaggac atacttccac    360

aggatcactg tgtacctgag aaagaagaaa cacagcctct gtgcctggga ggtgatcgca    420

gcagaagtct ggagagccct ctcttcctca accaacttgc tggcaagact gagtgaggag    480

aaggag                                                               486


<210> SEQ ID NO 29
<211> LENGTH: 162
<212> TYPE: PRT
<213> ORGANISM: Artificial Sequence
<220> FEATURE:
<223> OTHER INFORMATION: Amino acid sequence of Mouse IFNa4(A145G)

<400> SEQUENCE: 29

Cys Asp Leu Pro His Thr Tyr Asn Leu Gly Asn Lys Arg Ala Leu Thr
1               5                   10                  15

Val Leu Glu Glu Met Arg Arg Leu Pro Pro Leu Ser Cys Leu Lys Asp
            20                  25                  30

Arg Lys Asp Phe Gly Phe Pro Leu Glu Lys Val Asp Asn Gln Gln Ile
        35                  40                  45

Gln Lys Ala Gln Ala Ile Leu Val Leu Arg Asp Leu Thr Gln Gln Ile
    50                  55                  60

Leu Asn Leu Phe Thr Ser Lys Asp Leu Ser Ala Thr Trp Asn Ala Thr
65                  70                  75                  80

Leu Leu Asp Ser Phe Cys Asn Asp Leu His Gln Gln Leu Asn Asp Leu
                85                  90                  95

Lys Ala Cys Val Met Gln Glu Pro Pro Leu Thr Gln Glu Asp Ser Leu
            100                 105                 110

Leu Ala Val Arg Thr Tyr Phe His Arg Ile Thr Val Tyr Leu Arg Lys
        115                 120                 125

Lys Lys His Ser Leu Cys Ala Trp Glu Val Ile Arg Gly Glu Val Trp
    130                 135                 140

Arg Ala Leu Ser Ser Ser Thr Asn Leu Leu Ala Arg Leu Ser Glu Glu
145                 150                 155                 160

Lys Glu
```

<210> SEQ ID NO 30
<211> LENGTH: 486
<212> TYPE: DNA
<213> ORGANISM: Artificial Sequence
<220> FEATURE:
<223> OTHER INFORMATION: Coding nucleic acid sequence of Mouse
IFNa4(A145G)

<400> SEQUENCE: 30
tgtgacctgc ctcacactta taacctcggg aacaagaggg ccttgacagt cctggaagaa 60
atgagaagac tcccccctct ttcctgcctg aaggacagga aggattttgg attccccttg 120
gagaaggtgg ataaccaaca gatccagaag gctcaagcca tccttgtgct aagagatctt 180
acccagcaga ttttgaacct cttcacatca aaagacttgt ctgctacttg gaatgcaact 240
ctcctagact cattctgcaa tgacctccat cagcagctca atgatctcaa agcctgtgtg 300
atgcaggaac ctcctctgac ccaggaagac tccctgctgg ctgtgaggac atacttccac 360
aggatcactg tgtacctgag aaagaagaaa cacagcctct gtgcctggga ggtgatcaga 420
ggagaagtct ggagagccct ctcttcctca accaacttgc tggcaagact gagtgaggag 480
aaggag 486

<210> SEQ ID NO 31
<211> LENGTH: 162
<212> TYPE: PRT
<213> ORGANISM: Artificial Sequence
<220> FEATURE:
<223> OTHER INFORMATION: Amino acid sequence of Mouse IFNa4(R149A)

<400> SEQUENCE: 31

Cys Asp Leu Pro His Thr Tyr Asn Leu Gly Asn Lys Arg Ala Leu Thr
1 5 10 15

Val Leu Glu Glu Met Arg Arg Leu Pro Pro Leu Ser Cys Leu Lys Asp
20 25 30

Arg Lys Asp Phe Gly Phe Pro Leu Glu Lys Val Asp Asn Gln Gln Ile
35 40 45

Gln Lys Ala Gln Ala Ile Leu Val Leu Arg Asp Leu Thr Gln Gln Ile
50 55 60

Leu Asn Leu Phe Thr Ser Lys Asp Leu Ser Ala Thr Trp Asn Ala Thr
65 70 75 80

Leu Leu Asp Ser Phe Cys Asn Asp Leu His Gln Gln Leu Asn Asp Leu
85 90 95

Lys Ala Cys Val Met Gln Glu Pro Pro Leu Thr Gln Glu Asp Ser Leu
100 105 110

Leu Ala Val Arg Thr Tyr Phe His Arg Ile Thr Val Tyr Leu Arg Lys
115 120 125

Lys Lys His Ser Leu Cys Ala Trp Glu Val Ile Arg Ala Glu Val Trp
130 135 140

Ala Ala Leu Ser Ser Ser Thr Asn Leu Leu Ala Arg Leu Ser Glu Glu
145 150 155 160

Lys Glu

<210> SEQ ID NO 32
<211> LENGTH: 486
<212> TYPE: DNA

<213> ORGANISM: Artificial Sequence
<220> FEATURE:
<223> OTHER INFORMATION: Coding nucleic acid sequence of Mouse IFNa4(R149A)

<400> SEQUENCE: 32
tgtgacctgc ctcacactta taacctcggg aacaagaggg ccttgacagt cctggaagaa 60
atgagaagac tcccccctct ttcctgcctg aaggacagga aggattttgg attccccttg 120
gagaaggtgg ataaccaaca gatccagaag gctcaagcca tccttgtgct aagagatctt 180
acccagcaga ttttgaacct cttcacatca aaagacttgt ctgctacttg gaatgcaact 240
ctcctagact cattctgcaa tgacctccat cagcagctca atgatctcaa agcctgtgtg 300
atgcaggaac ctcctctgac ccaggaagac tccctgctgg ctgtgaggac atacttccac 360
aggatcactg tgtacctgag aaagaagaaa cacagcctct gtgcctggga ggtgatcaga 420
gcagaagtct gggcagccct ctcttcctca accaacttgc tggcaagact gagtgaggag 480
aaggag 486

<210> SEQ ID NO 33
<211> LENGTH: 162
<212> TYPE: PRT
<213> ORGANISM: Artificial Sequence
<220> FEATURE:
<223> OTHER INFORMATION: Amino acid sequence of Mouse IFNa4(S152A)

<400> SEQUENCE: 33

Cys Asp Leu Pro His Thr Tyr Asn Leu Gly Asn Lys Arg Ala Leu Thr
1 5 10 15

Val Leu Glu Glu Met Arg Arg Leu Pro Pro Leu Ser Cys Leu Lys Asp
20 25 30

Arg Lys Asp Phe Gly Phe Pro Leu Glu Lys Val Asp Asn Gln Gln Ile
35 40 45

Gln Lys Ala Gln Ala Ile Leu Val Leu Arg Asp Leu Thr Gln Gln Ile
50 55 60

Leu Asn Leu Phe Thr Ser Lys Asp Leu Ser Ala Thr Trp Asn Ala Thr
65 70 75 80

Leu Leu Asp Ser Phe Cys Asn Asp Leu His Gln Gln Leu Asn Asp Leu
85 90 95

Lys Ala Cys Val Met Gln Glu Pro Pro Leu Thr Gln Glu Asp Ser Leu
100 105 110

Leu Ala Val Arg Thr Tyr Phe His Arg Ile Thr Val Tyr Leu Arg Lys
115 120 125

Lys Lys His Ser Leu Cys Ala Trp Glu Val Ile Arg Ala Glu Val Trp
130 135 140

Arg Ala Leu Ala Ser Ser Thr Asn Leu Leu Ala Arg Leu Ser Glu Glu
145 150 155 160

Lys Glu

<210> SEQ ID NO 34
<211> LENGTH: 486
<212> TYPE: DNA
<213> ORGANISM: Artificial Sequence
<220> FEATURE:
<223> OTHER INFORMATION: Coding nucleic acid sequence of Mouse IFNa4(S152A)

<400> SEQUENCE: 34
tgtgacctgc ctcacactta taacctcggg aacaagaggg ccttgacagt cctggaagaa 60
atgagaagac tcccccctct ttcctgcctg aaggacagga aggattttgg attccccttg 120
gagaaggtgg ataaccaaca gatccagaag gctcaagcca tccttgtgct aagagatctt 180
acccagcaga ttttgaacct cttcacatca aaagacttgt ctgctacttg gaatgcaact 240
ctcctagact cattctgcaa tgacctccat cagcagctca atgatctcaa agcctgtgtg 300
atgcaggaac ctcctctgac ccaggaagac tccctgctgg ctgtgaggac atacttccac 360
aggatcactg tgtacctgag aaagaagaaa cacagcctct gtgcctggga ggtgatcaga 420
gcagaagtct ggagagccct cgcatcctca accaacttgc tggcaagact gagtgaggag 480
aaggag 486

<210> SEQ ID NO 35
<211> LENGTH: 165
<212> TYPE: PRT
<213> ORGANISM: Artificial Sequence
<220> FEATURE:
<223> OTHER INFORMATION: Amino acid sequence of Human IFNa2(Q124R)

<400> SEQUENCE: 35

Cys Asp Leu Pro Gln Thr His Ser Leu Gly Ser Arg Arg Thr Leu Met
1 5 10 15

Leu Leu Ala Gln Met Arg Arg Ile Ser Leu Phe Ser Cys Leu Lys Asp
20 25 30

Arg His Asp Phe Gly Phe Pro Gln Glu Glu Phe Gly Asn Gln Phe Gln
35 40 45

Lys Ala Glu Thr Ile Pro Val Leu His Glu Met Ile Gln Gln Ile Phe
50 55 60

Asn Leu Phe Ser Thr Lys Asp Ser Ser Ala Ala Trp Asp Glu Thr Leu
65 70 75 80

Leu Asp Lys Phe Tyr Thr Glu Leu Tyr Gln Gln Leu Asn Asp Leu Glu
85 90 95

Ala Cys Val Ile Gln Gly Val Gly Val Thr Glu Thr Pro Leu Met Lys
100 105 110

Glu Asp Ser Ile Leu Ala Val Arg Lys Tyr Phe Arg Arg Ile Thr Leu
115 120 125

Tyr Leu Lys Glu Lys Lys Tyr Ser Pro Cys Ala Trp Glu Val Val Arg
130 135 140

Ala Glu Ile Met Arg Ser Phe Ser Leu Ser Thr Asn Leu Gln Glu Ser
145 150 155 160

Leu Arg Ser Lys Glu
165

<210> SEQ ID NO 36
<211> LENGTH: 495
<212> TYPE: DNA
<213> ORGANISM: Artificial Sequence
<220> FEATURE:
<223> OTHER INFORMATION: Coding nucleic acid sequence of Human
IFNa2(Q124R)

<400> SEQUENCE: 36
tgcgatttac cccagacaca ctctttaggc tctcgtagga ccctcatgct gctggcccag 60
atgaggagga tctctttatt ctcttgttta aaggacagac acgacttcgg cttcccccaa 120

-continued gaagagttcg gcaaccagtt ccagaaggct gagaccatcc ccgtgctgca cgagatgatc 180
cagcagatct tcaatttatt tagcaccaag gactccagcg ccgcttggga tgagacttta 240
ctggacaagt tctacaccga actgtaccag cagctgaacg atttagaggc ttgtgtgatc 300
caaggtgtgg gagtgaccga gacccctctg atgaaggagg actccatttt agccgtgagg 360
aagtactttc gtaggatcac cctctacctc aaggagaaga agtacagccc ttgcgcttgg 420
gaggtggtga gggctgagat tatgaggagc ttctctttat ccaccaatct gcaagaatct 480
ttaaggtcca aggaa 495

<210> SEQ ID NO 37
<211> LENGTH: 435
<212> TYPE: PRT
<213> ORGANISM: Artificial Sequence
<220> FEATURE:
<223> OTHER INFORMATION: Amino acid sequence of mIFNa4(L30A)-Fc-hole in heterodimer

<400> SEQUENCE: 37

Met Glu Thr Asp Thr Leu Leu Leu Trp Val Leu Leu Leu Trp Val Pro
1 5 10 15

Gly Ser Thr Gly Ser Arg Cys Asp Leu Pro His Thr Tyr Asn Leu Gly
20 25 30

Asn Lys Arg Ala Leu Thr Val Leu Glu Glu Met Arg Arg Leu Pro Pro
35 40 45

Leu Ser Cys Ala Lys Asp Arg Lys Asp Phe Gly Phe Pro Leu Glu Lys
50 55 60

Val Asp Asn Gln Gln Ile Gln Lys Ala Gln Ala Ile Leu Val Leu Arg
65 70 75 80

Asp Leu Thr Gln Gln Ile Leu Asn Leu Phe Thr Ser Lys Asp Leu Ser
85 90 95

Ala Thr Trp Asn Ala Thr Leu Leu Asp Ser Phe Cys Asn Asp Leu His
100 105 110

Gln Gln Leu Asn Asp Leu Lys Ala Cys Val Met Gln Glu Pro Pro Leu
115 120 125

Thr Gln Glu Asp Ser Leu Leu Ala Val Arg Thr Tyr Phe His Arg Ile
130 135 140

Thr Val Tyr Leu Arg Lys Lys Lys His Ser Leu Cys Ala Trp Glu Val
145 150 155 160

Ile Arg Ala Glu Val Trp Arg Ala Leu Ser Ser Ser Thr Asn Leu Leu
165 170 175

Ala Arg Leu Ser Glu Glu Lys Glu Ser Gly Gly Gly Gly Ser Gly Gly
180 185 190

Gly Gly Ser Gly Gly Gly Gly Ser Gly Gly Gly Gly Arg Thr Asp Lys
195 200 205

Thr His Thr Cys Pro Pro Cys Pro Ala Pro Glu Leu Leu Gly Gly Pro
210 215 220

Ser Val Phe Leu Phe Pro Pro Lys Pro Lys Asp Thr Leu Met Ile Ser
225 230 235 240

Arg Thr Pro Glu Val Thr Cys Val Val Val Asp Val Ser His Glu Asp
245 250 255

Pro Glu Val Lys Phe Asn Trp Tyr Val Asp Gly Val Glu Val His Asn
260 265 270

Ala Lys Thr Lys Pro Arg Glu Glu Gln Tyr Asn Ser Thr Tyr Arg Val
275 280 285

-continued

Val Ser Val Leu Thr Val Leu His Gln Asp Trp Leu Asn Gly Lys Glu
    290                 295                 300

Tyr Lys Cys Lys Val Ser Asn Lys Ala Leu Pro Ala Pro Ile Glu Lys
305                 310                 315                 320

Thr Ile Ser Lys Ala Lys Gly Gln Pro Arg Glu Pro Gln Val Cys Thr
                325                 330                 335

Leu Pro Pro Ser Arg Asp Glu Leu Thr Lys Asn Gln Val Ser Leu Ser
            340                 345                 350

Cys Ala Val Lys Gly Phe Tyr Pro Ser Asp Ile Ala Val Glu Trp Glu
        355                 360                 365

Ser Asn Gly Gln Pro Glu Asn Asn Tyr Lys Thr Thr Pro Pro Val Leu
    370                 375                 380

Asp Ser Asp Gly Ser Phe Phe Leu Val Ser Lys Leu Thr Val Asp Lys
385                 390                 395                 400

Ser Arg Trp Gln Gln Gly Asn Val Phe Ser Cys Ser Val Met His Glu
                405                 410                 415

Ala Leu His Asn His Tyr Thr Gln Lys Ser Leu Ser Leu Ser Pro Gly
            420                 425                 430

Lys His Val
        435

<210> SEQ ID NO 38
<211> LENGTH: 1311
<212> TYPE: DNA
<213> ORGANISM: Artificial Sequence
<220> FEATURE:
<223> OTHER INFORMATION: Coding nucleic acid sequence of mIFNa4(L30A)-
      Fc-hole in heterodimer

<400> SEQUENCE: 38
gccgccacca tggagacaga cacactcctg ctatgggtac tgctgctctg ggttccaggt     60
tccactggtt cgcgatgtga cctgcctcac acttataacc tcgggaacaa gagggccttg    120
acagtcctgg aagaaatgag aagactcccc cctctttcct gcgcgaagga caggaaggat    180
tttggattcc ccttggagaa ggtggataac caacagatcc agaaggctca agccatcctt    240
gtgctaagag atcttaccca gcagattttg aacctcttca catcaaaaga cttgtctgct    300
acttggaatg caactctcct agactcattc tgcaatgacc tccatcagca gctcaatgat    360
ctcaaagcct gtgtgatgca ggaacctcct ctgacccagg aagactccct gctggctgtg    420
aggacatact tccacaggat cactgtgtac ctgagaaaga agaaacacag cctctgtgcc    480
tgggaggtga tcagagcaga agtctggaga gccctctctt cctcaaccaa cttgctggca    540
agactgagtg aggagaagga gagtggcggt ggtggctccg gcggtggtgg ctccggcggt    600
ggtggctccg gcggtggtgg ccgtacggac aagacccaca cctgcccccc ctgccccgcc    660
cccgagctgc tgggcggccc cagcgtgttc ctgttccccc ccaagcccaa ggacaccctg    720
atgatcagcc gcacccccga ggtgacctgc gtggtggtgg acgtgagcca cgaggacccc    780
gaggtgaagt tcaactggta cgtggacggc gtggaggtgc acaacgccaa gaccaagccc    840
cgcgaggagc agtacaacag cacctaccgc gtggtgagcg tgctgaccgt gctgcaccag    900
gactggctga acggcaagga gtacaagtgc aaggtgagca acaaggccct gcccgccccc    960
atcgagaaga ccatcagcaa ggccaagggc cagccccgcg agccccaggt gtgcaccctg   1020
ccccccagcc gcgacgagct gaccaagaac caggtgagcc tgagctgcgc cgtgaagggc   1080
ttctacccca gcgacatcgc cgtggagtgg gagagcaacg gccagcccga gaacaactac   1140

-continued

```
aagaccaccc cccccgtgct ggacagcgac ggcagcttct tcctggtgag caagctgacc   1200

gtggacaaga gccgctggca gcagggcaac gtgttcagct gcagcgtgat gcacgaggcc   1260

ctgcacaacc actacaccca gaagagcctg agcctgagcc ccggcaagta a            1311


<210> SEQ ID NO 39
<211> LENGTH: 435
<212> TYPE: PRT
<213> ORGANISM: Artificial Sequence
<220> FEATURE:
<223> OTHER INFORMATION: Amino acid sequence of mIFNa4 (R144A)-Fc-hole
      in heterodimer

<400> SEQUENCE: 39

Met Glu Thr Asp Thr Leu Leu Leu Trp Val Leu Leu Leu Trp Val Pro
1               5                   10                  15

Gly Ser Thr Gly Ser Arg Cys Asp Leu Pro His Thr Tyr Asn Leu Gly
            20                  25                  30

Asn Lys Arg Ala Leu Thr Val Leu Glu Glu Met Arg Arg Leu Pro Pro
        35                  40                  45

Leu Ser Cys Leu Lys Asp Arg Lys Asp Phe Gly Phe Pro Leu Glu Lys
    50                  55                  60

Val Asp Asn Gln Gln Ile Gln Lys Ala Gln Ala Ile Leu Val Leu Arg
65                  70                  75                  80

Asp Leu Thr Gln Gln Ile Leu Asn Leu Phe Thr Ser Lys Asp Leu Ser
                85                  90                  95

Ala Thr Trp Asn Ala Thr Leu Leu Asp Ser Phe Cys Asn Asp Leu His
            100                 105                 110

Gln Gln Leu Asn Asp Leu Lys Ala Cys Val Met Gln Glu Pro Pro Leu
        115                 120                 125

Thr Gln Glu Asp Ser Leu Leu Ala Val Arg Thr Tyr Phe His Arg Ile
    130                 135                 140

Thr Val Tyr Leu Arg Lys Lys Lys His Ser Leu Cys Ala Trp Glu Val
145                 150                 155                 160

Ile Ala Ala Glu Val Trp Arg Ala Leu Ser Ser Ser Thr Asn Leu Leu
                165                 170                 175

Ala Arg Leu Ser Glu Glu Lys Glu Ser Gly Gly Gly Gly Ser Gly Gly
            180                 185                 190

Gly Gly Ser Gly Gly Gly Gly Ser Gly Gly Gly Gly Arg Thr Asp Lys
        195                 200                 205

Thr His Thr Cys Pro Pro Cys Pro Ala Pro Glu Leu Leu Gly Gly Pro
    210                 215                 220

Ser Val Phe Leu Phe Pro Pro Lys Pro Lys Asp Thr Leu Met Ile Ser
225                 230                 235                 240

Arg Thr Pro Glu Val Thr Cys Val Val Val Asp Val Ser His Glu Asp
                245                 250                 255

Pro Glu Val Lys Phe Asn Trp Tyr Val Asp Gly Val Glu Val His Asn
            260                 265                 270

Ala Lys Thr Lys Pro Arg Glu Glu Gln Tyr Asn Ser Thr Tyr Arg Val
        275                 280                 285

Val Ser Val Leu Thr Val Leu His Gln Asp Trp Leu Asn Gly Lys Glu
    290                 295                 300

Tyr Lys Cys Lys Val Ser Asn Lys Ala Leu Pro Ala Pro Ile Glu Lys
305                 310                 315                 320

Thr Ile Ser Lys Ala Lys Gly Gln Pro Arg Glu Pro Gln Val Cys Thr
                325                 330                 335
```

```
Leu Pro Pro Ser Arg Asp Glu Leu Thr Lys Asn Gln Val Ser Leu Ser
            340                 345                 350

Cys Ala Val Lys Gly Phe Tyr Pro Ser Asp Ile Ala Val Glu Trp Glu
        355                 360                 365

Ser Asn Gly Gln Pro Glu Asn Asn Tyr Lys Thr Thr Pro Pro Val Leu
    370                 375                 380

Asp Ser Asp Gly Ser Phe Phe Leu Val Ser Lys Leu Thr Val Asp Lys
385                 390                 395                 400

Ser Arg Trp Gln Gln Gly Asn Val Phe Ser Cys Ser Val Met His Glu
                405                 410                 415

Ala Leu His Asn His Tyr Thr Gln Lys Ser Leu Ser Leu Ser Pro Gly
            420                 425                 430

Lys His Val
        435
```

<210> SEQ ID NO 40
<211> LENGTH: 1311
<212> TYPE: DNA
<213> ORGANISM: Artificial Sequence
<220> FEATURE:
<223> OTHER INFORMATION: Coding nucleic acid sequence of mIFNa4(R144A)-
Fc-hole in heterodimer

<400> SEQUENCE: 40

```
gccgccacca tggagacaga cacactcctg ctatgggtac tgctgctctg ggttccaggt      60

tccactggtt cgcgatgtga cctgcctcac acttataacc tcgggaacaa gagggccttg     120

acagtcctgg aagaaatgag aagactcccc cctctttcct gcctgaagga caggaaggat     180

tttggattcc ccttggagaa ggtggataac caacagatcc agaaggctca agccatcctt     240

gtgctaagag atcttaccca gcagattttg aacctcttca catcaaaaga cttgtctgct     300

acttggaatg caactctcct agactcattc tgcaatgacc tccatcagca gctcaatgat     360

ctcaaagcct gtgtgatgca ggaacctcct ctgacccagg aagactccct gctggctgtg     420

aggacatact tccacaggat cactgtgtac ctgagaaaga agaaacacag cctctgtgcc     480

tgggaggtga tcgcagcaga agtctggaga gccctctctt cctcaaccaa cttgctggca     540

agactgagtg aggagaagga gagtggcggt ggtggctccg gcggtggtgg ctccggcggt     600

ggtggctccg gcggtggtgg ccgtacggac aagacccaca cctgcccccc ctgccccgcc     660

cccgagctgc tgggcggccc cagcgtgttc ctgttccccc ccaagcccaa ggacaccctg     720

atgatcagcc gcacccccga ggtgacctgc gtggtggtgg acgtgagcca cgaggacccc     780

gaggtgaagt tcaactggta cgtggacggc gtggaggtgc acaacgccaa gaccaagccc     840

cgcgaggagc agtacaacag cacctaccgc gtggtgagcg tgctgaccgt gctgcaccag     900

gactggctga acggcaagga gtacaagtgc aaggtgagca acaaggccct gcccgccccc     960

atcgagaaga ccatcagcaa ggccaagggc cagccccgcg agccccaggt gtgcaccctg    1020

ccccccagcc gcgacgagct gaccaagaac caggtgagcc tgagctgcgc cgtgaagggc    1080

ttctacccca gcgacatcgc cgtggagtgg gagagcaacg gccagcccga gaacaactac    1140

aagaccaccc cccccgtgct ggacagcgac ggcagcttct tcctggtgag caagctgacc    1200

gtggacaaga gccgctggca gcagggcaac gtgttcagct gcagcgtgat gcacgaggcc    1260

ctgcacaacc actacaccca gaagagcctg agcctgagcc ccggcaagta a             1311
```

<210> SEQ ID NO 41

<211> LENGTH: 435
<212> TYPE: PRT
<213> ORGANISM: Artificial Sequence
<220> FEATURE:
<223> OTHER INFORMATION: Amino acid sequence of mIFNa4(A145G)-Fc-hole in heterodimer

<400> SEQUENCE: 41

```
Met Glu Thr Asp Thr Leu Leu Leu Trp Val Leu Leu Leu Trp Val Pro
1               5                   10                  15

Gly Ser Thr Gly Ser Arg Cys Asp Leu Pro His Thr Tyr Asn Leu Gly
            20                  25                  30

Asn Lys Arg Ala Leu Thr Val Leu Glu Glu Met Arg Arg Leu Pro Pro
        35                  40                  45

Leu Ser Cys Leu Lys Asp Arg Lys Asp Phe Gly Phe Pro Leu Glu Lys
    50                  55                  60

Val Asp Asn Gln Gln Ile Gln Lys Ala Gln Ala Ile Leu Val Leu Arg
65                  70                  75                  80

Asp Leu Thr Gln Gln Ile Leu Asn Leu Phe Thr Ser Lys Asp Leu Ser
                85                  90                  95

Ala Thr Trp Asn Ala Thr Leu Leu Asp Ser Phe Cys Asn Asp Leu His
            100                 105                 110

Gln Gln Leu Asn Asp Leu Lys Ala Cys Val Met Gln Glu Pro Pro Leu
        115                 120                 125

Thr Gln Glu Asp Ser Leu Leu Ala Val Arg Thr Tyr Phe His Arg Ile
    130                 135                 140

Thr Val Tyr Leu Arg Lys Lys Lys His Ser Leu Cys Ala Trp Glu Val
145                 150                 155                 160

Ile Arg Gly Glu Val Trp Arg Ala Leu Ser Ser Ser Thr Asn Leu Leu
                165                 170                 175

Ala Arg Leu Ser Glu Glu Lys Glu Ser Gly Gly Gly Gly Ser Gly Gly
            180                 185                 190

Gly Gly Ser Gly Gly Gly Gly Ser Gly Gly Gly Gly Arg Thr Asp Lys
        195                 200                 205

Thr His Thr Cys Pro Pro Cys Pro Ala Pro Glu Leu Leu Gly Gly Pro
    210                 215                 220

Ser Val Phe Leu Phe Pro Pro Lys Pro Lys Asp Thr Leu Met Ile Ser
225                 230                 235                 240

Arg Thr Pro Glu Val Thr Cys Val Val Val Asp Val Ser His Glu Asp
                245                 250                 255

Pro Glu Val Lys Phe Asn Trp Tyr Val Asp Gly Val Glu Val His Asn
            260                 265                 270

Ala Lys Thr Lys Pro Arg Glu Glu Gln Tyr Asn Ser Thr Tyr Arg Val
        275                 280                 285

Val Ser Val Leu Thr Val Leu His Gln Asp Trp Leu Asn Gly Lys Glu
    290                 295                 300

Tyr Lys Cys Lys Val Ser Asn Lys Ala Leu Pro Ala Pro Ile Glu Lys
305                 310                 315                 320

Thr Ile Ser Lys Ala Lys Gly Gln Pro Arg Glu Pro Gln Val Cys Thr
                325                 330                 335

Leu Pro Pro Ser Arg Asp Glu Leu Thr Lys Asn Gln Val Ser Leu Ser
            340                 345                 350

Cys Ala Val Lys Gly Phe Tyr Pro Ser Asp Ile Ala Val Glu Trp Glu
        355                 360                 365
```

```
Ser Asn Gly Gln Pro Glu Asn Asn Tyr Lys Thr Thr Pro Pro Val Leu
    370                 375                 380

Asp Ser Asp Gly Ser Phe Phe Leu Val Ser Lys Leu Thr Val Asp Lys
385                 390                 395                 400

Ser Arg Trp Gln Gln Gly Asn Val Phe Ser Cys Ser Val Met His Glu
                405                 410                 415

Ala Leu His Asn His Tyr Thr Gln Lys Ser Leu Ser Leu Ser Pro Gly
            420                 425                 430

Lys His Val
        435


<210> SEQ ID NO 42
<211> LENGTH: 1311
<212> TYPE: DNA
<213> ORGANISM: Artificial Sequence
<220> FEATURE:
<223> OTHER INFORMATION: Coding nucleic acid sequence of mIFNa4(A145G)-
      Fc-hole in heterodimer

<400> SEQUENCE: 42

gccgccacca tggagacaga cacactcctg ctatgggtac tgctgctctg ggttccaggt     60

tccactggtt cgcgatgtga cctgcctcac acttataacc tcgggaacaa gagggccttg    120

acagtcctgg aagaaatgag aagactcccc cctctttcct gcctgaagga caggaaggat    180

tttggattcc ccttggagaa ggtggataac caacagatcc agaaggctca agccatcctt    240

gtgctaagag atcttaccca gcagattttg aacctcttca catcaaaaga cttgtctgct    300

acttggaatg caactctcct agactcattc tgcaatgacc tccatcagca gctcaatgat    360

ctcaaagcct gtgtgatgca ggaacctcct ctgacccagg aagactccct gctggctgtg    420

aggacatact tccacaggat cactgtgtac ctgagaaaga agaaacacag cctctgtgcc    480

tgggaggtga tcagaggaga agtctggaga gccctctctt cctcaaccaa cttgctggca    540

agactgagtg aggagaagga gagtggcggt ggtggctccg gcggtggtgg ctccggcggt    600

ggtggctccg gcggtggtgg ccgtacggac aagacccaca cctgcccccc ctgccccgcc    660

cccgagctgc tgggcggccc cagcgtgttc ctgttccccc ccaagcccaa ggacaccctg    720

atgatcagcc gcacccccga ggtgacctgc gtggtggtgg acgtgagcca cgaggacccc    780

gaggtgaagt tcaactggta cgtggacggc gtggaggtgc acaacgccaa gaccaagccc    840

cgcgaggagc agtacaacag cacctaccgc gtggtgagcg tgctgaccgt gctgcaccag    900

gactggctga acggcaagga gtacaagtgc aaggtgagca acaaggccct gcccgccccc    960

atcgagaaga ccatcagcaa ggccaagggc cagccccgcg agccccaggt gtgcaccctg   1020

ccccccagcc gcgacgagct gaccaagaac caggtgagcc tgagctgcgc cgtgaagggc   1080

ttctacccca gcgacatcgc cgtggagtgg gagagcaacg gccagcccga gaacaactac   1140

aagaccaccc cccccgtgct ggacagcgac ggcagcttct tcctggtgag caagctgacc   1200

gtggacaaga gccgctggca gcagggcaac gtgttcagct gcagcgtgat gcacgaggcc   1260

ctgcacaacc actacaccca gaagagcctg agcctgagcc ccggcaagta a            1311


<210> SEQ ID NO 43
<211> LENGTH: 436
<212> TYPE: PRT
<213> ORGANISM: Artificial Sequence
<220> FEATURE:
<223> OTHER INFORMATION: Amino acid sequence of mIFNa4 (R149A)-Fc-hole
      in heterodimer
```

<400> SEQUENCE: 43

Met Glu Thr Asp Thr Leu Leu Leu Trp Val Leu Leu Leu Trp Val Pro
1               5                   10                  15

Gly Ser Thr Gly Ser Arg Cys Asp Leu Pro His Thr Tyr Asn Leu Gly
            20                  25                  30

Asn Lys Arg Ala Leu Thr Val Leu Glu Glu Met Arg Arg Leu Pro Pro
        35                  40                  45

Leu Ser Cys Leu Lys Asp Arg Lys Asp Phe Gly Phe Pro Leu Glu Lys
    50                  55                  60

Val Asp Asn Gln Gln Ile Gln Lys Ala Gln Ala Ile Leu Val Leu Arg
65                  70                  75                  80

Asp Leu Thr Gln Gln Ile Leu Asn Leu Phe Thr Ser Lys Asp Leu Ser
                85                  90                  95

Ala Thr Trp Asn Ala Thr Leu Leu Asp Ser Phe Cys Asn Asp Leu His
            100                 105                 110

Gln Gln Leu Asn Asp Leu Lys Ala Cys Val Met Gln Glu Pro Pro Leu
        115                 120                 125

Thr Gln Glu Asp Ser Leu Leu Ala Val Arg Thr Tyr Phe His Arg Ile
    130                 135                 140

Thr Val Tyr Leu Arg Lys Lys Lys His Ser Leu Cys Ala Trp Glu Val
145                 150                 155                 160

Ile Arg Ala Glu Val Trp Ala Ala Leu Ser Ser Ser Thr Asn Leu Leu
                165                 170                 175

Ala Arg Leu Ser Glu Glu Lys Glu Ser Ser Gly Gly Gly Gly Ser Gly
            180                 185                 190

Gly Gly Gly Ser Gly Gly Gly Gly Ser Gly Gly Gly Gly Arg Thr Asp
        195                 200                 205

Lys Thr His Thr Cys Pro Pro Cys Pro Ala Pro Glu Leu Leu Gly Gly
    210                 215                 220

Pro Ser Val Phe Leu Phe Pro Pro Lys Pro Lys Asp Thr Leu Met Ile
225                 230                 235                 240

Ser Arg Thr Pro Glu Val Thr Cys Val Val Val Asp Val Ser His Glu
                245                 250                 255

Asp Pro Glu Val Lys Phe Asn Trp Tyr Val Asp Gly Val Glu Val His
            260                 265                 270

Asn Ala Lys Thr Lys Pro Arg Glu Glu Gln Tyr Asn Ser Thr Tyr Arg
        275                 280                 285

Val Val Ser Val Leu Thr Val Leu His Gln Asp Trp Leu Asn Gly Lys
    290                 295                 300

Glu Tyr Lys Cys Lys Val Ser Asn Lys Ala Leu Pro Ala Pro Ile Glu
305                 310                 315                 320

Lys Thr Ile Ser Lys Ala Lys Gly Gln Pro Arg Glu Pro Gln Val Cys
                325                 330                 335

Thr Leu Pro Pro Ser Arg Asp Glu Leu Thr Lys Asn Gln Val Ser Leu
            340                 345                 350

Ser Cys Ala Val Lys Gly Phe Tyr Pro Ser Asp Ile Ala Val Glu Trp
        355                 360                 365

Glu Ser Asn Gly Gln Pro Glu Asn Asn Tyr Lys Thr Thr Pro Pro Val
    370                 375                 380

Leu Asp Ser Asp Gly Ser Phe Phe Leu Val Ser Lys Leu Thr Val Asp
385                 390                 395                 400

Lys Ser Arg Trp Gln Gln Gly Asn Val Phe Ser Cys Ser Val Met His
405 410 415

Glu Ala Leu His Asn His Tyr Thr Gln Lys Ser Leu Ser Leu Ser Pro
420 425 430

Gly Lys His Val
435

<210> SEQ ID NO 44
<211> LENGTH: 1311
<212> TYPE: DNA
<213> ORGANISM: Artificial Sequence
<220> FEATURE:
<223> OTHER INFORMATION: Coding nucleic acid sequence of mIFNa4(R149A)-Fc-hole in heterodimer

<400> SEQUENCE: 44
gccgccacca tggagacaga cacactcctg ctatgggtac tgctgctctg ggttccaggt 60
tccactggtt cgcgatgtga cctgcctcac acttataacc tcgggaacaa gagggccttg 120
acagtcctgg aagaaatgag aagactcccc cctctttcct gcctgaagga caggaaggat 180
tttggattcc ccttggagaa ggtggataac caacagatcc agaaggctca agccatcctt 240
gtgctaagag atcttaccca gcagattttg aacctcttca catcaaaaga cttgtctgct 300
acttggaatg caactctcct agactcattc tgcaatgacc tccatcagca gctcaatgat 360
ctcaaagcct gtgtgatgca ggaacctcct ctgacccagg aagactccct gctggctgtg 420
aggacatact tccacaggat cactgtgtac ctgagaaaga agaaacacag cctctgtgcc 480
tgggaggtga tcagagcaga agtctgggca gccctctctt cctcaaccaa cttgctggca 540
agactgagtg aggagaagga gagtggcggt ggtggctccg gcggtggtgg ctccggcggt 600
ggtggctccg gcggtggtgg ccgtacggac aagacccaca cctgcccccc ctgccccgcc 660
cccgagctgc tgggcggccc cagcgtgttc ctgttccccc ccaagcccaa ggacaccctg 720
atgatcagcc gcacccccga ggtgacctgc gtggtggtgg acgtgagcca cgaggacccc 780
gaggtgaagt tcaactggta cgtggacggc gtggaggtgc acaacgccaa gaccaagccc 840
cgcgaggagc agtacaacag cacctaccgc gtggtgagcg tgctgaccgt gctgcaccag 900
gactggctga acggcaagga gtacaagtgc aaggtgagca acaaggccct gcccgccccc 960
atcgagaaga ccatcagcaa ggccaagggc cagccccgcg agccccaggt gtgcaccctg 1020
ccccccagcc gcgacgagct gaccaagaac caggtgagcc tgagctgcgc cgtgaagggc 1080
ttctacccca gcgacatcgc cgtggagtgg gagagcaacg gccagcccga gaacaactac 1140
aagaccaccc cccccgtgct ggacagcgac ggcagcttct tcctggtgag caagctgacc 1200
gtggacaaga gccgctggca gcagggcaac gtgttcagct gcagcgtgat gcacgaggcc 1260
ctgcacaacc actacaccca gaagagcctg agcctgagcc ccggcaagta a 1311

<210> SEQ ID NO 45
<211> LENGTH: 435
<212> TYPE: PRT
<213> ORGANISM: Artificial Sequence
<220> FEATURE:
<223> OTHER INFORMATION: Amino acid sequence of mIFNa4(S152A)-Fc-hole in heterodimer

<400> SEQUENCE: 45

Met Glu Thr Asp Thr Leu Leu Leu Trp Val Leu Leu Leu Trp Val Pro
1 5 10 15

-continued

```
Gly Ser Thr Gly Ser Arg Cys Asp Leu Pro His Thr Tyr Asn Leu Gly
            20                  25                  30

Asn Lys Arg Ala Leu Thr Val Leu Glu Glu Met Arg Arg Leu Pro Pro
        35                  40                  45

Leu Ser Cys Leu Lys Asp Arg Lys Asp Phe Gly Phe Pro Leu Glu Lys
    50                  55                  60

Val Asp Asn Gln Gln Ile Gln Lys Ala Gln Ala Ile Leu Val Leu Arg
65                  70                  75                  80

Asp Leu Thr Gln Gln Ile Leu Asn Leu Phe Thr Ser Lys Asp Leu Ser
                85                  90                  95

Ala Thr Trp Asn Ala Thr Leu Leu Asp Ser Phe Cys Asn Asp Leu His
            100                 105                 110

Gln Gln Leu Asn Asp Leu Lys Ala Cys Val Met Gln Glu Pro Pro Leu
        115                 120                 125

Thr Gln Glu Asp Ser Leu Leu Ala Val Arg Thr Tyr Phe His Arg Ile
    130                 135                 140

Thr Val Tyr Leu Arg Lys Lys Lys His Ser Leu Cys Ala Trp Glu Val
145                 150                 155                 160

Ile Arg Ala Glu Val Trp Ala Ala Leu Ser Ser Ser Thr Asn Leu Leu
                165                 170                 175

Ala Arg Leu Ser Glu Glu Lys Glu Ser Gly Gly Gly Gly Ser Gly Gly
            180                 185                 190

Gly Gly Ser Gly Gly Gly Gly Ser Gly Gly Gly Gly Arg Thr Asp Lys
        195                 200                 205

Thr His Thr Cys Pro Pro Cys Pro Ala Pro Glu Leu Leu Gly Gly Pro
    210                 215                 220

Ser Val Phe Leu Phe Pro Pro Lys Pro Lys Asp Thr Leu Met Ile Ser
225                 230                 235                 240

Arg Thr Pro Glu Val Thr Cys Val Val Val Asp Val Ser His Glu Asp
                245                 250                 255

Pro Glu Val Lys Phe Asn Trp Tyr Val Asp Gly Val Glu Val His Asn
            260                 265                 270

Ala Lys Thr Lys Pro Arg Glu Glu Gln Tyr Asn Ser Thr Tyr Arg Val
        275                 280                 285

Val Ser Val Leu Thr Val Leu His Gln Asp Trp Leu Asn Gly Lys Glu
    290                 295                 300

Tyr Lys Cys Lys Val Ser Asn Lys Ala Leu Pro Ala Pro Ile Glu Lys
305                 310                 315                 320

Thr Ile Ser Lys Ala Lys Gly Gln Pro Arg Glu Pro Gln Val Cys Thr
                325                 330                 335

Leu Pro Pro Ser Arg Asp Glu Leu Thr Lys Asn Gln Val Ser Leu Ser
            340                 345                 350

Cys Ala Val Lys Gly Phe Tyr Pro Ser Asp Ile Ala Val Glu Trp Glu
        355                 360                 365

Ser Asn Gly Gln Pro Glu Asn Asn Tyr Lys Thr Thr Pro Pro Val Leu
    370                 375                 380

Asp Ser Asp Gly Ser Phe Phe Leu Val Ser Lys Leu Thr Val Asp Lys
385                 390                 395                 400

Ser Arg Trp Gln Gln Gly Asn Val Phe Ser Cys Ser Val Met His Glu
                405                 410                 415
```

Ala Leu His Asn His Tyr Thr Gln Lys Ser Leu Ser Leu Ser Pro Gly
420 425 430

Lys His Val
435

<210> SEQ ID NO 46
<211> LENGTH: 1311
<212> TYPE: DNA
<213> ORGANISM: Artificial Sequence
<220> FEATURE:
<223> OTHER INFORMATION: Coding nucleic acid sequence of mIFNa4(S152A)-Fc-hole in heterodimer

<400> SEQUENCE: 46
gccgccacca tggagacaga cacactcctg ctatgggtac tgctgctctg ggttccaggt 60
tccactggtt cgcgatgtga cctgcctcac acttataacc tcgggaacaa gagggccttg 120
acagtcctgg aagaaatgag aagactcccc cctctttcct gcctgaagga caggaaggat 180
tttggattcc ccttggagaa ggtggataac caacagatcc agaaggctca agccatcctt 240
gtgctaagag atcttaccca gcagattttg aacctcttca catcaaaaga cttgtctgct 300
acttggaatg caactctcct agactcattc tgcaatgacc tccatcagca gctcaatgat 360
ctcaaagcct gtgtgatgca ggaacctcct ctgacccagg aagactccct gctggctgtg 420
aggacatact tccacaggat cactgtgtac ctgagaaaga agaaacacag cctctgtgcc 480
tgggaggtga tcagagcaga agtctgggca gccctctctt cctcaaccaa cttgctggca 540
agactgagtg aggagaagga gagtggcggt ggtggctccg gcggtggtgg ctccggcggt 600
ggtggctccg gcggtggtgg ccgtacggac aagacccaca cctgcccccc ctgccccgcc 660
cccgagctgc tgggcggccc cagcgtgttc ctgttccccc ccaagcccaa ggacaccctg 720
atgatcagcc gcacccccga ggtgacctgc gtggtggtgg acgtgagcca cgaggacccc 780
gaggtgaagt tcaactggta cgtggacggc gtggaggtgc acaacgccaa gaccaagccc 840
cgcgaggagc agtacaacag cacctaccgc gtggtgagcg tgctgaccgt gctgcaccag 900
gactggctga acggcaagga gtacaagtgc aaggtgagca acaaggccct gcccgccccc 960
atcgagaaga ccatcagcaa ggccaagggc cagccccgcg agccccaggt gtgcaccctg 1020
ccccccagcc gcgacgagct gaccaagaac caggtgagcc tgagctgcgc cgtgaagggc 1080
ttctacccca gcgacatcgc cgtggagtgg gagagcaacg gccagcccga gaacaactac 1140
aagaccaccc cccccgtgct ggacagcgac ggcagcttct tcctggtgag caagctgacc 1200
gtggacaaga gccgctggca gcagggcaac gtgttcagct gcagcgtgat gcacgaggcc 1260
ctgcacaacc actacaccca gaagagcctg agcctgagcc ccggcaagta a 1311

<210> SEQ ID NO 47
<211> LENGTH: 438
<212> TYPE: PRT
<213> ORGANISM: Artificial Sequence
<220> FEATURE:
<223> OTHER INFORMATION: Amino acid sequence of hIFNa2(Q124R)-Fc-hole in heterodimer

<400> SEQUENCE: 47

Met Glu Thr Asp Thr Leu Leu Leu Trp Val Leu Leu Leu Trp Val Pro
1 5 10 15

Gly Ser Thr Gly Ser Arg Cys Asp Leu Pro Gln Thr His Ser Leu Gly
20 25 30

-continued

```
Ser Arg Arg Thr Leu Met Leu Leu Ala Gln Met Arg Arg Ile Ser Leu
        35                  40                  45

Phe Ser Cys Leu Lys Asp Arg His Asp Phe Gly Phe Pro Gln Glu Glu
    50                  55                  60

Phe Gly Asn Gln Phe Gln Lys Ala Glu Thr Ile Pro Val Leu His Glu
65                  70                  75                  80

Met Ile Gln Gln Ile Phe Asn Leu Phe Ser Thr Lys Asp Ser Ser Ala
                85                  90                  95

Ala Trp Asp Glu Thr Leu Leu Asp Lys Phe Tyr Thr Glu Leu Tyr Gln
            100                 105                 110

Gln Leu Asn Asp Leu Glu Ala Cys Val Ile Gln Gly Val Gly Val Thr
        115                 120                 125

Glu Thr Pro Leu Met Lys Glu Asp Ser Ile Leu Ala Val Arg Lys Tyr
    130                 135                 140

Phe Arg Arg Ile Thr Leu Tyr Leu Lys Glu Lys Lys Tyr Ser Pro Cys
145                 150                 155                 160

Ala Trp Glu Val Val Arg Ala Glu Ile Met Arg Ser Phe Ser Leu Ser
                165                 170                 175

Thr Asn Leu Gln Glu Ser Leu Arg Ser Lys Glu Ser Gly Gly Gly Gly
            180                 185                 190

Ser Gly Gly Gly Gly Ser Gly Gly Gly Gly Ser Gly Gly Gly Gly Arg
        195                 200                 205

Thr Asp Lys Thr His Thr Cys Pro Pro Cys Pro Ala Pro Glu Leu Leu
    210                 215                 220

Gly Gly Pro Ser Val Phe Leu Phe Pro Pro Lys Pro Lys Asp Thr Leu
225                 230                 235                 240

Met Ile Ser Arg Thr Pro Glu Val Thr Cys Val Val Val Asp Val Ser
                245                 250                 255

His Glu Asp Pro Glu Val Lys Phe Asn Trp Tyr Val Asp Gly Val Glu
            260                 265                 270

Val His Asn Ala Lys Thr Lys Pro Arg Glu Glu Gln Tyr Asn Ser Thr
        275                 280                 285

Tyr Arg Val Val Ser Val Leu Thr Val Leu His Gln Asp Trp Leu Asn
    290                 295                 300

Gly Lys Glu Tyr Lys Cys Lys Val Ser Asn Lys Ala Leu Pro Ala Pro
305                 310                 315                 320

Ile Glu Lys Thr Ile Ser Lys Ala Lys Gly Gln Pro Arg Glu Pro Gln
                325                 330                 335

Val Cys Thr Leu Pro Pro Ser Arg Asp Glu Leu Thr Lys Asn Gln Val
            340                 345                 350

Ser Leu Ser Cys Ala Val Lys Gly Phe Tyr Pro Ser Asp Ile Ala Val
        355                 360                 365

Glu Trp Glu Ser Asn Gly Gln Pro Glu Asn Asn Tyr Lys Thr Thr Pro
    370                 375                 380

Pro Val Leu Asp Ser Asp Gly Ser Phe Phe Leu Val Ser Lys Leu Thr
385                 390                 395                 400

Val Asp Lys Ser Arg Trp Gln Gln Gly Asn Val Phe Ser Cys Ser Val
                405                 410                 415

Met His Glu Ala Leu His Asn His Tyr Thr Gln Lys Ser Leu Ser Leu
            420                 425                 430

Ser Pro Gly Lys His Val
        435
```

-continued

```
<210> SEQ ID NO 48
<211> LENGTH: 1320
<212> TYPE: DNA
<213> ORGANISM: Artificial Sequence
<220> FEATURE:
<223> OTHER INFORMATION: Coding nucleic acid sequence of hIFNa2(Q124R)-
      Fc-hole in heterodimer

<400> SEQUENCE: 48

gccgccacca tggagacaga cacactcctg ctatgggtac tgctgctctg ggttccaggt     60

tccactggtt cgcgatgcga tttaccccag acacactctt taggctctcg taggaccctc    120

atgctgctgg cccagatgag gaggatctct ttattctctt gtttaaagga cagacacgac    180

ttcggcttcc cccaagaaga gttcggcaac cagttccaga aggctgagac catccccgtg    240

ctgcacgaga tgatccagca gatcttcaat ttatttagca ccaaggactc cagcgccgct    300

tgggatgaga ctttactgga caagttctac accgaactgt accagcagct gaacgattta    360

gaggcttgtg tgatccaagg tgtgggagtg accgagaccc ctctgatgaa ggaggactcc    420

attttagccg tgaggaagta ctttcgtagg atcaccctct acctcaagga gaagaagtac    480

agcccttgcg cttgggaggt ggtgagggct gagattatga ggagcttctc tttatccacc    540

aatctgcaag aatctttaag gtccaaggaa agtggcggtg gtggctccgg cggtggtggc    600

tccggcggtg gtggctccgg cggtggtggc cgtacggaca agacccacac ctgccccccc    660

tgccccgccc ccgagctgct gggcggcccc agcgtgttcc tgttcccccc caagcccaag    720

gacaccctga tgatcagccg cacccccgag gtgacctgcg tggtggtgga cgtgagccac    780

gaggaccccg aggtgaagtt caactggtac gtggacggcg tggaggtgca caacgccaag    840

accaagcccc gcgaggagca gtacaacagc acctaccgcg tggtgagcgt gctgaccgtg    900

ctgcaccagg actggctgaa cggcaaggag tacaagtgca aggtgagcaa caaggccctg    960

cccgccccca tcgagaagac catcagcaag gccaagggcc agccccgcga gccccaggtg   1020

tgcaccctgc cccccagccg cgacgagctg accaagaacc aggtgagcct gagctgcgcc   1080

gtgaagggct tctaccccag cgacatcgcc gtggagtggg agagcaacgg ccagcccgag   1140

aacaactaca agaccacccc ccccgtgctg gacagcgacg gcagcttctt cctggtgagc   1200

aagctgaccg tggacaagag ccgctggcag cagggcaacg tgttcagctg cagcgtgatg   1260

cacgaggccc tgcacaacca ctacacccag aagagcctga gcctgagccc cggcaagtaa   1320
```

FUSION PROTEIN OF INTERFERON (IFN) AND ANTI-PD-L1 ANTIBODY AND USE THEREOF

CROSS REFERENCE TO THE RELATED APPLICATIONS

This application is the national phase entry of International Application No. PCT/CN2019/082360, filed on Apr. 12, 2019, which is based upon and claims priority to Chinese Patent Application No. 201810336178.1, filed on Apr. 16, 2018, the entire contents of which are incorporated herein by reference.

SEQUENCE LISTING

The instant application contains a Sequence Listing which has been submitted in ASCII format via EFS-Web and is hereby incorporated by reference in its entirety. Said ASCII copy is named "GBCHTN001-PKG-Sequence Listing.txt", created on Oct. 22, 2020 and is 95,232 bytes in size.

TECHNICAL FIELD

The present invention belongs to the technical field of genetic engineering and biomedical medicine, and in particular, relates to a fusion protein of an interferon (IFN) and an anti-PD-L1 antibody, a pharmaceutical composition and a kit containing the same, and use thereof in the treatment of tumor diseases.

BACKGROUND

Programmed cell death protein 1 (PD-1) is a key immune checkpoint molecule. It can inhibit the TCR signal activation of T cells, which reduces the strength and duration of the immune response. A ligand of PD-1, PD-L1, is generally up-regulated in tumor cells, which is one of the immune evasion mechanisms of tumors. PD-1/PD-L1 blocking therapy (PD therapy) can induce a variety of cancer patients to produce a lasting immune response to tumor cells. In practice, however, objective and effective immune responses are only observed in a small number of patients undergoing PD therapy. In addition, drug resistance occurring in acquired PD therapy is also receiving wider attention, while its mechanism is still unclear. Therefore, it has become the top priority of PD therapy-related research to study and analyze why certain tumors cannot respond to or become resistant to PD therapy.

Some scholars have proposed that PD therapy can effectively control tumors because T cells release immunosuppressive signals. It is reported that the excellent efficacy of PD therapy is related to a sufficient number of tumor infiltrating lymphocytes (TILs). Even in the case of a large number of TILs, however, PD therapy alone may not be effective in (re)activating tumor-specific T cells. In these cases, it may need to block other negative synergistic inhibitors or up-regulate stimulus signals to induce the (re)activation of T cells. There are still many unanswered questions about the signaling molecules that can effectively promote cell immunity.

Type I IFNs include IFNα and IFNβ, which activate T cells by promoting the maturation of dendritic cells (DCs) that process and present antigens, thereby acting as a bridge between natural immunity and adaptive immunity. Early studies have found that type I IFNs have the effect of inhibiting tumor cell proliferation and promoting apoptosis.

Therefore, type I IFNs are approved for treating clinically specific tumors, including lymphoma, melanoma, renal cell carcinoma (RCC), etc. Recent studies have shown that antigen-presenting cell (APC) and T cell activation mediated by the type I IFN signaling pathway plays a vital role in tumor radiotherapy and chemotherapy. The expression of type I IFNs in tumor tissues, however, is very low. Exogenous type I IFN treatment can not only inhibit the proliferation and survival of tumors, but also activate the anti-tumor immune response, which has thus become an important research focus.

Clinically, high-dose type I IFN treatment will bring better tumor control effects. However, because IFNARs are widely expressed in normal tissues, high-dose type I IFN can induce severe side effects in patients, including flu-like symptoms (fever, headache, etc.), vomit, leukopenia, anemia, thrombocytopenia or the like. In addition, type I IFNs can up-regulate the expression of the immunosuppressive molecule PD-L1, which in turn inhibits the anti-tumor immune response and reduces the therapeutic effect. How to overcome the systemic toxicity and immunosuppression caused by type I IFNs is an important problem to be solved.

SUMMARY

Despite the presence of TILs, most patients still do not respond to intensive PD-1/PD-L1 therapy. The inventors believe that the defective activation of innate immune APCs may limit the complete activation of tumor-specific T cells after PD-1/PD-L1 blockade. Local delivery of type I IFNs restores the antigen presentation, but also up-regulates PD-L1, which inhibits the subsequent activation of T cells. In order to overcome the limitations and deficiencies existing in the prior art, the present invention provides a fusion protein of IFN-anti-PD-L1 antibody (IFN-anti-PD-L1), which can target both PD-L1 and IFN receptors. It is observed in experiments that the IFN-anti-PD-L1 fusion protein can accumulate in tumor tissues, significantly increase the antigen cross-presentation and overcome the PD-L1-mediated immune suppression. The IFN-anti-PD-L1 fusion protein can simultaneously release immunosuppressive signals and provide costimulatory signals to (re)activate T cells, and can be used as a new generation of anti-PD-L1 antibodies for treating neoplastic diseases.

The objectives of the present invention are achieved by the following technical solutions.

The present invention provides a fusion protein, which is IFN-anti-PD-L1 formed by fusion of IFN and a PD-L1 binding protein. The fusion protein is a homodimer protein or a heterodimer protein.

In the present invention, the homodimer protein includes a first polypeptide and a second polypeptide that are the same, and the first polypeptide and the second polypeptide include an IFN, a PD-L1 binding protein, and an immunoglobulin (Ig) Fc region in sequence from N-terminus to C-terminus.

In the present invention, the heterodimer protein includes a first polypeptide and a second polypeptide that are different, the first polypeptide includes a PD-L1 binding protein, and the second polypeptide includes an Ig Fc region and an IFN located at the N-terminus of the Fc region. An Fc region in the first polypeptide and the Fc region in the second polypeptide are derived from Igs of the same or different subtypes.

In the present invention, the IFN can be selected from a type I IFN, a type I IFN mutant, a type II IFN and/or a type III IFN, such as IFN-α, IFN-β, IFN-γ, IFN-λ1 (IL-29), IFN-λ2 (IL-28a), IFN-λ (IL-28b) and IFN-ω; preferably a type I IFN; more preferably IFN-α4; and further more preferably an IFN-α4 mutant. The IFN can be derived from human or mice. The IFN is preferably IFN-α4 (SEQ ID NO: 13), more preferably an IFN-α4 mutant, and further more preferably mutants mIFN-α4 (L30A) (SEQ ID NO: 25), mIFN-α4 (R-144A) (SEQ ID NO: 27), mIFN-α4 (A145G) (SEQ ID NO: 29), mIFN-α4 (R149A) (SEQ ID NO: 31), mIFN-α4 (S152A) (SEQ ID NO: 33), and hIFN-α2 (Q124R) (SEQ ID NO: 35).

In the present invention, the Ig Fc region can be selected from amino acid sequences of constant regions of IgG1, IgG2, IgG3 and/or IgG4, and preferably of IgG1. IgG1 has a stronger ability to induce antibody-dependent cellular cytotoxicity (ADCC) and complement-dependent cytotoxicity (CDC) effects and a longer serum half-life, which is the most common antibody subtype in antibody drugs; and IgG2 and IgG4 have a weaker ability to induce ADCC and CDC effects, but exhibit a longer serum half-life.

In the present invention, the PD-L1 binding protein can be selected from an anti-PD-L1 antibody (an intact antibody), a single-chain variable fragment (ScFv), an Fab fragment, and an $F(ab')_2$ fragment; and the anti-PD-L1 antibody is selected from: preferably Tecentriq, Bavencio, Imfinzi, KN035, CS1001 KL-A167, SHR-1316 and/or YW243.55.S70, more preferably ScFv that binds to PD-L1, and further more preferably YW243.55.S70.

In the present invention, the first polypeptide and the second polypeptide of the homodimer preferably include an amino acid sequence shown in SEQ ID NO: 3; and the first polypeptide of the heterodimer preferably includes an amino acid sequence shown in SEQ ID NO: 1, and the second polypeptide includes an amino acid sequence shown in SEQ ID NOS: 2, 37, 39, 41, 43, 45, or 47.

The present invention also provides use of the fusion protein, where the IFN-anti-PD-L1 is applied to tumor cells, which can inhibit the growth and/or migration of tumor cells.

The present invention provides use of the IFN-anti-PD-L1 fusion protein in treating neoplastic diseases and use of the IFN-anti-PD-L1 fusion protein in the preparation of drugs or kits. The tumor is preferably a tumor or an advanced tumor against which PD-1/PD-L1 blockade alone is ineffective, and more preferably a tumor that is resistant or irresponsive to an anti-PD-1/PD-L1 antibody alone; and the above tumor is preferably B-cell lymphoma, colon cancer and melanoma.

The present invention provides a pharmaceutical preparation or a pharmaceutical composition, and the active ingredient of the pharmaceutical preparation includes the fusion protein IFN-anti-PD1 of the present invention.

The present invention provides a kit including the fusion protein IFN-anti-PD-L1 of the present invention.

The present invention provides nucleic acid molecules encoding the fusion protein IFN-anti-PD-L1 of the present invention.

Among the nucleic acid molecules: 1) nucleic acid molecules encoding the homodimer preferably have nucleotide sequences shown in SEQ ID NO: 6; and 2) nucleic acid molecules encoding the heterodimer can have nucleotide sequences selected from SEQ ID NOS: 4, 5, 7, 8, 9, 10, 38, 40, 42, 44, 45, and 48, and preferably shown in SEQ ID NOS: 4 and SEQ ID NO: 5, SEQ ID NOS: 4 and SEQ ID NO: 40, or SEQ ID NO: 4 and SEQ ID NO: 42.

The present invention provides a vector including the above nucleic acid molecules.

The present invention provides a cell including the fusion protein IFN-anti-PD-L1 of the present invention or nucleic acid molecules encoding the fusion protein, which is used for producing the fusion protein. The cell is selected from non-human mammalian cells, and preferably from CHO and HEK293 cells.

The present invention provides a method for treating tumors, including administering an effective amount of the fusion protein IFN-anti-PD-L1 to a cancer patient. The tumor is preferably a tumor against which PD-1/PD-L1 blockade alone is ineffective.

The present invention provides a method for treating a tumor or an advanced tumor against which PD-1/PD-1 blockade alone is ineffective, including administering effective amounts of IFN-α and an anti-PD-L1 antibody to a patient. Moreover, the present invention provides use of IFN-α and an anti-PD-L1 antibody together in the preparation of a pharmaceutical composition, a pharmaceutical preparation or a kit. The present invention also provides a pharmaceutical composition, a pharmaceutical preparation or a kit including IFN-α and an anti-PD-L1 antibody. The IFN-α needs to be intratumorally administered.

On this basis, the present invention provides a combination therapy of an anti-PD-1/PD-L1 antibody and IFN-anti-PD-L1, and a pharmaceutical composition or a kit including the anti-PD-1/PD-L1 antibody and IFN-anti-PD-L1 fusion protein. The therapy includes administering effective amounts of an anti-PD-1/PD-L1 antibody and IFN-anti-PD-L1 to a patient sequentially or simultaneously. The tumor is a tumor or an advanced tumor that is resistant or irresponsive to PD-1/PD-L1 blockade alone; and preferably, a tumor that is resistant or irresponsive to an anti-PD-1/PD-L1 antibody alone. Or, a patient with the tumor suffers from diseases related to defects/disorders in transport of peripheral lymphocytes, and the peripheral lymphocytes of the patient cannot migrate to tumor tissues.

The present invention provides use of the fusion protein IFN-anti-PD-L1 and an anti-PD-1/PD-L1 antibody together in the preparation of a pharmaceutical composition or a kit for treating tumors. The tumor is a tumor or an advanced tumor against which PD-1/PD-L1 blockade alone is ineffective; and preferably, a tumor that is resistant or irresponsive to an anti-PD-1/PD-L1 antibody alone. Or, a patient with the tumor suffers from diseases related to defects/disorders in transport of peripheral lymphocytes, and the peripheral lymphocytes of the patient cannot migrate to tumor tissues.

The present invention provides use of IFN-α and an anti-PD-L1 antibody together in the preparation of a pharmaceutical composition, a pharmaceutical preparation or a kit for treating a tumor or an advanced tumor against which PD-1/PD-L1 blockade alone is ineffective, and the IFN-α needs to be intratumorally administered.

The present invention provides a pharmaceutical composition, a pharmaceutical preparation or a kit including IFN-α and an anti-PD-L1 antibody, and the IFN-α needs to be intratumorally administered.

The present invention provides use of the fusion protein IFN-anti-PD-L1 in up-regulating the expression of IFN receptors in leukocytes; the leukocytes are preferably CD45+ cells; and the IFN receptors are preferably IFNARs. Moreover, the present invention provides use of the fusion protein IFN-anti-PD-L1 in the preparation of a composition for up-regulating the expression of IFN receptors in leukocytes.

The present invention provides use of the fusion protein IFN-anti-PD-L1 in activating DC cells or TIL cells. Moreover, the present invention provides use of the fusion protein IFN-anti-PD-L1 in the preparation of a composition for activating DC cells or TIL cells.

The present invention provides use of the fusion protein IFN-anti-PD-L1 in activating tumor-resident T cells. Moreover, the present invention provides use of the fusion protein IFN-anti-PD-L1 in the preparation of a composition for activating tumor-resident T cells.

The above "use" can mean use for a therapeutic purpose or use for a non-therapeutic purpose.

The present invention provides an IFN-α4 mutant involving mutation that weakens the affinity with a receptor, including mIFN-α4 (L30A) (SEQ ID NO: 25), mIFN-α4 (R144A) (SEQ ID NO: 27), mIFN-α4 (A145G) (SEQ ID NO: 29), mIFN-α4 (R149A) (SEQ ID NO: 31), mIFN-α4 (S152A) (SEQ ID NO: 33), and/or hIFN-α2 (Q124R) (SEQ ID NO: 35).

The present invention provides isolated nucleic acid molecules encoding the IFN-α4 mutant, and the nucleic acid molecules have nucleotide sequences shown in SEQ ID NOS: 26, 28, 30, 32, 34, or 36.

The present invention provides use of the IFN-α4 mutant in the preparation of a fusion protein or drug for treating tumors.

Terms and Definitions

Unless otherwise specified, the terms and definitions used in this application have meanings commonly used in the art and are known to those skilled in the art.

As used in this application, the term "tumor site" refers to an in vivo or in vitro location that includes or is suspected to include tumor cells. The tumor site includes a solid tumor and a location close to or adjacent to where a tumor grows.

As used in this application, the term "administration" refers to systemic and/or topical administration. The term "systemic administration" refers to non-topical administration, so that the administered substance may affect several organs or tissues in the entire body, or the administered substance may traverse several organs or tissues in the entire body to reach a target site. For example, administration to the circulatory system of a subject can cause the expression of a therapeutic product by the administered vector in more than one tissues or organs, or can cause the expression of a therapeutic product by the administered vector at a specific site. For example, this is attributed to natural tropism or operable connection with tissue-specific promoter elements. Those skilled in the art will understand that the systemic administration encompasses various forms of administration, including but not limited to: parenteral administration, intravenous administration, intramuscular administration, subcutaneous administration, transdermal administration, intratumoral administration, oral administration, etc.

The term "topical administration" refers to administration at or around a specific site. Those skilled in the art will understand that topical administration encompasses various forms of administration, such as injection directly into a specific site or injection around the specific site (e.g., intratumoral administration).

As used herein, the term "therapeutically effective amount" refers to an amount of the IFN of the present invention or a component in the kit of the present invention required to achieve the purpose of treating a target disease or condition (e.g., tumor/cancer, for example, for causing the tumor regression or reducing the tumor size). The effective amount can be determined for a specific purpose through practice and in a conventional manner. In particular, the therapeutically effective amount may be an amount required to achieve the following purposes: reducing the number of cancer cells; reducing the tumor size; inhibiting (i.e., slowing or stopping) the infiltration of cancer cells into peripheral organs; inhibiting (i.e., slowing or stopping) the tumor metastasis; and inhibiting the tumor growth; and/or alleviating one or more symptoms related to cancer.

The term "antibody" encompasses, for example, monoclonal antibodies, polyclonal antibodies, ScFv, and antibody fragments (which exhibit the desired biological or immunological activity). In this application, the terms "immunoglobulin" (Ig) and antibody can be used interchangeably. The antibody can specifically target tumor antigens, for example, surface tumor antigens, such as EGFR, CD4, CD8, and Neu.

The "tumor" of the present invention can be selected from B-cell lymphoma, lung cancer, bronchial cancer, colorectal cancer, prostate cancer, breast cancer, pancreatic cancer, gastric cancer, ovarian cancer, bladder cancer, brain or central nervous system (CNS) cancers, peripheral nerves system (PNS) cancers, esophageal cancer, cervical cancer, melanoma, uterine or endometrial cancer, oral or laryngeal cancer, liver cancer, kidney cancer, cholangiocarcinoma, small intestine cancer or appendix cancer, salivary gland cancer, thymic cancer, adrenal cancer, osteosarcoma, chondrosarcoma, lipoma, testicular cancer, and malignant fibrous histiocytoma (MFH).

The "tumor cell" of the present invention can be selected from cells produced by B-cell lymphoma, lung cancer, bronchial cancer, colorectal cancer, prostate cancer, breast cancer, pancreatic cancer, gastric cancer, ovarian cancer, bladder cancer, brain or CNS cancers, PNS cancers, esophageal cancer, cervical cancer, melanoma, uterine or endometrial cancer, oral or laryngeal cancer, liver cancer, kidney cancer, cholangiocarcinoma, small intestine cancer or appendix cancer, salivary gland cancer, thymic cancer, adrenal cancer, osteosarcoma, chondrosarcoma, lipoma, testicular cancer, and MFH.

The "application" or "use" in the present invention can mean use for a purpose of disease treatment or use for a non-therapeutic purpose, such as scientific research.

The present invention has the following beneficial effects:

1. The IFN-anti-PD-L1 fusion protein provided in the present invention targets both PD-L1 and IFN receptors, and data show that the activation of IFN signals in a tumor microenvironment (TME) can enhance the PD-1/PD-L1 therapy against advanced tumors by inducing stronger T cell activation.
2. Data show that, in the IFN-anti-PD-L1 fusion protein provided in the present invention, the anti-PD-L1 antibody (PD-L1 binding protein) can be used to specifically deliver immunomodulatory molecules to tumor tissues with minimal toxicity. The present invention lays a foundation for the development of a novel anti-PD-L1 antibody targeting tumors.
3. The IFN-anti-PD-L1 fusion protein provided in the present invention can lead to multiple feedforward responses targeting PD-L1 blockade and IFN-α receptor (IFNAR) activation in TME, which increases the targeting effect and enhances the response to IFN therapy, thereby realizing the synergistic effect of anti-PD-L1 and IFN to overcome PD-1/PD-L1 therapy and IFN resistance. Experimental data show that IFN-anti-PD-L1 can simultaneously target tumor tissues to activate APCs and block PD-L1 inhibitory signals, and can be used as a new generation of anti-PD-L1 antibodies for treating tumor diseases.

4. The IFN-anti-PD-L1 fusion protein provided in the present invention, when used in combination with PD-1/PD-L1 blockade, completely eliminates most of the PD-1/PD-L1-resistant tumors and also induces the memory T cell immune response.
5. The fusion protein provided by the present invention has two structures: homodimer and heterodimer, which exhibits high binding affinity to IFN receptors, more effective antiviral activity and excellent tumor targeting in vivo and in vitro, long serum half-life and prominent tumor control in vivo.
6. The fusion protein provided by the present invention includes a mutant IFNα with reduced affinity, which has more specific binding ability to target cells, avoiding the peripheral off-target effect of IFN.

BRIEF DESCRIPTION OF THE DRAWINGS

In FIG. 1A, Balb/c mice (n=3) are subcutaneously inoculated with $3\times10^6$ A20 cells; and mice carrying early-stage tumors (<50 $mm^3$) are intraperitoneally (i.p.) administered with 200 μg of anti-PD-L1 antibody on days 11 and 15. In FIG. 1B, mice (n=4) carrying advanced A20 tumors (>100 $mm^3$) are treated with 200 μg of anti-PD-L1 antibody on days 15 and 19. The tumor growth is measured twice a week. In FIG. 1C, mice are treated according to the conditions in FIGS. 1A and 1B. Three days after the treatment, lymph node (LN)-draining cells are isolated, and then co-cultivated with irradiated or unirradiated A20 cells for two days. The IFNγELISPOT assay is conducted. In FIG. 1D, A20 tumor-bearing mice (n=5) are treated with 200 μg of anti-PD-L1 antibody on days 11 and 15 (i.p.), and/or intratumorally injected with 25 μg of IFNα-Fc on day 11 (i.t.). In FIG. 1E, C57BL/6 mice (n=5) are inoculated with $5\times10^5$ MC38 cells. The mice are treated with 200 μg of anti-PD-L1 antibody (i.p.) on days 9, 12 and 15, and/or treated with 25 μg of IFNα-Fc on day 9. Survival curves are shown. In FIG. 1F, A20 tumor-bearing mice (n=5) are treated with 25 μg of IFNα-Fc on day 11 (i.t. or i.v.). The black arrow indicates treatment with IFNα-Fc. Data are shown as mean±SEM, and involve at least two independent experiments. *, $p<0.05$; **, $p<0.01$; and n.s., not significant.

FIG. 2A is a schematic diagram for the IFN-anti-PD-L1 fusion protein in the form of homodimer or heterodimer. ScFv represents a single-chain variable fragment. FIG. 2B is a flow cytogram illustrating the binding of proteins in IFNAR1$^{-/-}$ A20 cells. FIG. 2C is a flow cytogram illustrating the binding of proteins in PD-L1$^{-/-}$ A20 cells. The numbers indicate the mean fluorescence intensity (MFI). In FIG. 2D, the biological activity of the IFN-anti-PD-L1 protein is determined by the antiviral infection bioassay. Before infected with vesicular stomatitis virus (VSV)-GFP viruses, L929 cells are mixed with each protein and then cultivated overnight. After the cells are further cultivated for 30 h, the percentage of virus-infected cells is determined by flow cytometry (FCM). In FIGS. 2E and 2F, Balb/c mice (n=5) are inoculated with $3\times10^6$ A20 cells. After tumors are established, 20 μg of the corresponding protein is intratumorally injected (FIG. 2E, treating on days 18 and 22) or intravenously injected (FIG. 2F, treating on days 11 and 15), and the tumor size is measured twice a week. In FIG. 2G, C57BL/6 mice (n=4 to 8) are inoculated with $5\times10^5$ MC38 cells. On days 14 and 18, 25 μg of the control or fusion protein is injected intravenously. In FIGS. 2H and 2I, mice are injected intravenously with 25 μg of the indicated protein. The protein concentration in tumor tissue (FIG. 2H) or serum (FIG. 2I) is measured by ELISA at different time points. Data are shown as mean±SEM, and involve at least two independent experiments. *, $p<0.05$; and **, $p<0.01$.

In FIGS. 3A and 3B, 100 μg of IFN-anti-PD-L1 heterodimer or IFN-anti-HBs protein is injected intravenously into tumor-bearing mice on days 0 and 4. Survival curve and body weight change are shown in FIGS. 3A and 3B, respectively. In FIGS. 3C and 3H, 100 μg of IFN-anti-PD-L1 heterodimer or IFN-anti-HBs protein is injected intravenously into MC38 tumor-bearing mice. Serum is collected 6 h or 24 h after the injection. The cytokine cytometric bead array (CBA) technology is used to determine cytokine levels in serum. In FIG. 3D, on days 11 and 15, IFNα-Fc (12.5 μg), anti-PD-L1 antibody (12.5 μg), a mixture of IFNα-Fc and anti-PD-L1 antibody (12.5 μg+12.5 μg), or IFN-anti-PD-L1 fusion protein heterodimer (25 μg) is injected intravenously into A20 tumor-bearing mice (n=5). The tumor size is measured twice a week. In FIGS. 3E and 3I, MC38 tumor-bearing mice are treated with 25 μg of the control protein or IFN-anti-PD-L1 heterodimer. Two days later, tumor tissues are collected, and the PD-L1 level is determined by FCM. FMO represents fluorescence minus one. In FIGS. 3F-3G, mice are treated according to the conditions in FIGS. 3E and 3I. Tumor tissues are harvested two days later. The IFNAR levels in CD45-negative and cD45-positive cells are determined by FCM. Data are shown as mean±SEM, and involve at least two independent experiments. *, $p<0.05$; , $p<0.01$; *, $p<0.001$; n.d., not detectable; and n.s., not significant.

In FIG. 4A, PD-L1 expression in WT A20, PD-L1$^{-/-}$ A20, WT MC38, and PD-L1$^{-/-}$ MC38 cells is determined by FCM. In FIG. 4B, 30 μg of IFN-anti-PD-1 heterodimer is injected intravenously into WT or PD-L1$^{-/-}$ tumor-bearing mice. Tumor tissues are collected at different time points after the injection. The concentration of the fusion protein is measured by ELISA. In FIG. 4C, WT or PD-L1$^{-/-}$ A20 tumor-bearing mice (n=4 to 5) are treated with the control Ig or IFN-anti-PD-L1 on days 11 and 15. The tumor growth is measured twice a week. In FIG. 4D, WT or PD-L$^{-/-}$ MC38 tumor-bearing mice (n=5 to 6) are treated with the control Ig or IFN-anti-PD-L1 on days 8 and 12. In FIGS. 4E and 4G, MC38 tumor-bearing mice are treated with IFN-anti-PD-L1. Tumor tissues are collected two days later. The PD-L1 levels in CAD45-negative and CD45-positive cells are assessed by FCM. In FIG. 4F, PD-L1$^{-/-}$ mice (n=4 to 5) are inoculated with MC38 cells. Mice are treated with 25 μg of the control Ig or IFN-anti-PD-L1 on days 14 and 18. The tumor growth is measured twice a week. Data are shown as mean±SEM, and involve at least two independent experiments. *, $p<0.05$; , $p<0.01$; *, $p<0.001$; and n.s., not significant.

In FIG. 5A, A20 tumor-hearing mice (n=5) are treated with IFN-anti-PD-L1 on day 11. To block the IFNAR signaling pathway, mice are intratumorally (i.t.) injected with 100 μg of anti-IFNAR blocking antibody on days 11 and 14. In FIG. 5B, the expression of IFNAR in (B220+) WT or IFNAR$^{-/-}$ A20 tumor cells in vivo is evaluated by FCM. In FIG. 5C, IFNAR$^{-/-}$ A20 tumor-bearing mice (n=6) are treated with IFN-anti-PD-L1 on days 16 and 19. The tumor growth is measured twice a week. In FIG. 5D, WT or IFNAR1$^{-/-}$ mice are inoculated with $5\times10^5$ MC38 cells. Mice (n=4 to 5) are treated with 25 μg of IFN-anti-PD-L1 on days 10 and 13. In FIG. 5E, tumor-bearing mice (n=5 to 6) are treated with IFN-anti-PD-L1 on days 11 and 14. An anti-CD8 antibody for deletion is administered on days 9, 12 and 16. In FIGS. 5F and 5G, two days after the IFN-anti-PD-L1 treatment, MC38 tumor tissues are isolated. The expression of CD86 in tumor-infiltrating DCs (CD11c+MHCII+) is determined by FCM. FIG. 5F is a representative pattern, and FIG. 5G shows MFI. Data are shown as mean±SEM, and involve at least two independent experiments. *, p<0.05; , p<0.01; *, p<0.001; and n.s., not significant.

In FIG. 6A, A2.0 tumor-bearing Balb/c mice (n=4 to 5) are treated with 20 μg of IFN-anti-PD-L1 on day 15 and/or with 100 μg of anti-PD-1 antibody on days 14 and 17. The tumor growth is measured twice a week. In FIG. 6B, B16 tumor-bearing C57BL/6 mice (n=3 to 5) are treated with 25 μg of IFN-anti-PD-L1 on days 11 and 14 and/or with 100 μg of anti-PD-1 antibody on days 12 and 15. In FIG. 6C, mice (n=4) whose tumors completely regress after the combination therapy in (a) are re-inoculated with $2.5\times10^7$ A20 cells. Naive mice inoculated with A20 cells are adopted as the control. In FIG. 6D, Mice (n=4) are treated with the same IFN-anti-PD-L1 and anti-PD-1 in (a). To deplete the cells, mice are injected with 200 μg of anti-CD8 antibody one day before the anti-PD-1 antibody treatment. In FIG. 6E, mice are treated with IFN-anti-PD-L1 and/or anti-PD-1 as described in (a). 12 days after the treatment, tumor-draining lymph nodes (TDLNs) are isolated to prepare single cell suspensions. The cells are co-cultivated with irradiated or unirradiated A20. The IFNγELISPOT assay is conducted. In FIG. 6F, tumor-infiltrating DC (CD11c+) and T (CD8+) cells are isolated from A20 tumor-bearing mice, and co-cultivated in the presence of irradiated A20 cells. IFNα or anti-PD-L1 antibody is added to the medium. Three days later, the supernatant is collected, and the IFNγ level is determined by CBA. In FIG. 6G, A20 tumor-bearing mice (n=5 to 6) are treated with IFN-anti-PD-L1 and/or anti-PD-1 as described in FIG. 6A. FTY720 is administered once every other day from day 14. In order to delete CD8$^+$ T cells in the tumor, 30 μg of anti-CD8 antibody is injected into the tumor on days 14 and 17. The black and blue arrows indicate treatment with anti-PD-1 and treatment with IFN-anti-PD-L1, respectively. Data are shown as mean±SEM, and involve at least two independent experiments. *, p<0.05; , p<0.01; and *, p<0.001.

In FIG. 7A, 30 μg of IFN-anti-PD-L1 is injected intravenously into MC38 tumor-bearing mice. Tissues are collected on days 1, 3, and 5 after the injection. The concentration of the fusion protein is determined by ELISA. In FIGS. 7B-7D, MC38 tumor-hearing mice are treated as described in FIG. 3C, and serum is collected 6 h or 24 h after the injection. The cytokine levels in serum are determined by CBA. Data are shown as mean±SEM and involve two experimental replicates.

In FIG. 9A, in order to delete NK cells, 20 μg of anti-asialo GM1 antibody is injected intraperitoneally twice a week from day 13. In FIG. 9B, In order to delete CD4$^+$ T cells, 200 μg of anti-CD4 antibody is injected intraperitoneally twice a week from day 13. The tumor growth is measured twice a week. Data are shown as mean±SEM and involve two experimental replicates. The black and blue arrows indicate treatment with anti-PD-1 and treatment with IFN-anti-PD-L1, respectively. In FIG. 9C, mice are treated as described in FIG. 6E, and spleens are isolated to prepare single cell suspensions. The cells are co-cultivated with irradiated or unirradiated A20. The IFNγELISPOT assay is conducted.

FIG. 11 illustrates the construction of IFNα mutants with reduced affinity. Single site-directed selective mutations are conducted for key sites of type I IFN that interact with the receptors.

FIGS. 12A-12B illustrates the activity assay for IFNα-Fc mutants. The biological activity is assayed for IFNα-Fc mutants by the antiviral infection bioassay. Before infected with VSV-GFP viruses, L929 cells are mixed with each protein and then cultivated overnight. After the cells are further cultivated for 30 h, the percentage of virus-infected cells is determined by FCM, and the inhibition rates and $EC_{50}$ values of different concentrations of protein on cell infection are calculated. The two mutants R144A and A145G have the weakest activity and are potential preferred targets.

FIGS. 13A-13D illustrate the in vitro targeting test of mutant IFN-anti-PD-L1 WT PD-L1$^+$ A20 cells and PD-L1$^{-/-}$ A20 cells previously subjected to knockout by the CRISPR-Cas9 technology in the laboratory are adopted, different concentrations of bispecific protein are added, and resulting mixtures are incubated for 72 h. The proliferation is detected by a CCK8 kit for cells treated with different concentrations of protein. The ratio of $EC_{50}$ in PD-L1$^-$ A20 cells to $EC_{50}$ in PD-L1$^+$ A20 cells can reflect the targetability of this bispecific protein. It can be found from the normalization of the ratio with the data of wt-mIFNa4-Fc that R144A and A145G are the two with the optimal targetability.

DETAILED DESCRIPTION OF THE EMBODIMENTS

Figure 1A:
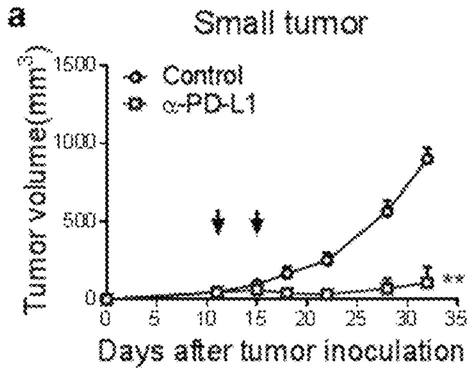
FIGS. 1A-1F illustrate that topical administration of type I IFN overcomes the resistance of advanced tumor to PD-1/PD-L1 blockade.

The present invention is further described in detail through the following examples, but it should be understood that the present invention is not limited by the following content.

Materials and Methods

Mice:

Female (6 to 8 weeks old) BALB/c mice and C57BL/6 mice were purchased from Beijing Vital River Laboratory Animal Technology Co., Ltd. (Beijing, China). All mice were kept under specific pathogen-free (SPF) conditions in the animal room of the Institute of Biophysics, Chinese Academy of Sciences. Animal care and experiments were conducted in accordance with the guidelines of the Institute of Biophysics, Chinese Academy of Sciences, which followed the protocol approved by Institutional Laboratory Animal Care and Use Committee (IACUC). PD-L1$^{-/-}$ and IFNAR1$^{-/-}$ mice were kept under SPF conditions at UT Southwestern Medical Center. The animal protocol complied with NIH guidelines. The study was approved by the Animal Care and Use Committee of UT Southwestern Medical Center.

Cell Lines and Reagents:

293F cells were provided by Dr. Xu Ting (Alphamab Oncology, Suzhou, Jiangsu Province, China) and were cultivated in SMM 293-TI medium (M293 TI, Sino Biological). A20, MC38 and L929 cell lines were purchased from the American Type Culture Collection (ATCC) (Manassas, VA). The anti-PD-1 blocking antibody (4H2) was purchased from Bristol-Myers Squibb (Redwood City, CA). The anti-PD-L1 antibody (10F.9G2) and anti-IFNAR1 antibody (MAR1-5A3) were purchased from BioXCell (West Lebanon, NH). The anti-CD8 (TIB210) and anti-CD4 (GK1.5) antibodies for deletion were prepared by the laboratory itself. The anti-asialo GM1 antibody was purchased from Biolegend (San Diego, CA).

Construction of IFN-Anti-PD-L1 Fusion Protein:

Heterodimer: The light-chain and heavy-chain variable regions of the PD-L1 binding protein (YW243.55.S70) sequence were synthesized according to U.S. Pat. No. 8,217,149B2. The light-chain and the heavy-chain sequences were linked via the GGGGSGGGGSGGGGS linker (for example, amino acids 111-125 of SEQ ID NO: 1), and human IgG1Fc (SEQ ID NO: 15) was inserted into the C-terminus of the heavy chain to give a first polypeptide of the heterodimer, named ScFv(PD-L1)-Fc (SEQ ID NO: 1). Then the coding nucleic acid sequence (SEQ ID NO: 4) of ScFv(PD-L1)-Fc was cloned into a pEE12.4 vector (Lonza). The cDNA sequence (SEQ ID NO: 14) of murine IFN-α4 (SEQ ID NO: 13) was cloned and inserted into the N-terminus of human IgG1Fc through the $(G4S)_4$ linker to give a second polypeptide of the heterodimer, mIFNα4-Fc (SEQ ID NO: 2). The nucleotide sequence (SEQ ID NO: 5) encoding mIFNα4-Fc was cloned into a pEE6.4 vector (Lonza). The heterodimerization of PD-L1 binding protein and IFNα was conducted using the knob-to-holes technique previously reported. Plasmids were transiently transfected into 293F cells at a ratio of 1:2. The supernatant was collected on day 7 after the transfection. The fusion protein was purified using a Protein A-Sepharose column according to the operational manual (Repligen).

During the preparation of the heterodimer, different type I IFNs were also used to prepare the second polypeptides mIFNb-Fc (with an encoding nucleic acid sequence shown in SEQ ID NO: 7), hIFNα2-Fc (with an encoding nucleic acid sequence shown in SEQ ID NO: 8), hIFNb-Fc (with an encoding nucleic acid sequence shown in SEQ ID NO: 9), and mIFNγ-Fc (with an encoding nucleic acid sequence shown in SEQ ID NO: 10), and the obtained heterodimers showed a relatively-high inhibitory activity on tumor cell proliferation. In the above-mentioned heterodimer fusion proteins, IFNα-Fc exhibited a better effect. Moreover, the heterodimer fusion protein composed of mIFNα4-Fc and Anti-PD-L1 exhibited the optimal effect, and relevant comparative data are not described here in detail.

Homodimer: The C-terminus of murine IFN-α4 was linked to the N-terminus of ScFv(PD-L1)-Fc to give a first and second polypeptides of the homodimer fusion protein (SEQ ID NO: 3). The nucleotide sequences (SEQ ID NO: 6) of the polypeptides were cloned into a pEE12.4 vector, and after transfection, the homodimer protein was formed spontaneously through Fc dimerization.

Flow Cytometry (FCM)

The binding of the fusion protein was detected using PE-anti-human IgG Fc (eBioscience). Specific antibodies: anti-PD-L1 antibody (10F.9G2), anti-IFNAR1 antibody (MAR1-5A3), anti-CD45 antibody (30-F11), anti-CD80 antibody (16-10A1), and anti-CD86 antibody (GL1) were from BioLegend or eBioscience. Cells were suspended in FACS buffer (1% bovine serum albumin (BSA) and 0.05% $NaN_3$), blocked with an anti-CD16/32 antibody (anti-FcγIII/II receptor, clone 2.4 G2) for 30 min, and then stained with a specific antibody for 30 min on ice. The samples were assayed on FACSCalibur oar Fortessa flowcytometer (BD Biosciences). Data were analyzed using FlowJo software (TreeStar).

Antiviral Activity of IFNα

L929 mouse fibroblasts sensitive to VSV infection were used to quantify the biological activity of IFN. The cells were incubated with serially-diluted IFNα-Fc or IFN-anti-PD-L1 at 37° C. overnight. The next day, the cells were infected with VSV-GFP with MOI=5, and then further cultivated for 30 h. The cells were then collected and fixed with 4% PFA. Data were acquired using FACSFotassa flow cytometer (BD Biosciences) and analyzed using FlowJo software (TreeStar). GFP-positive cells were defined as virus-infected cells.

Quantitative Study of Protein Distribution in Vivo

A20 cells ($3\times10^6$) were injected subcutaneously (s.c.) into the right side of Balb/c mice. On day 15, mice were injected intravenously with 30 μg of IFNα-Fc or IFN-anti-PD-L1. 3 days after perfusion, different mouse tissues were collected, and the levels of human Fc in the homogenate extracts of different organs and tissues were determined by ELISA.

Growth and Treatment of Tumors

A20 cells ($3\times10^6$) were injected subcutaneously into the right side of Balb/c mice. 20 μg of IFN-anti-PD-L1 was then injected intravenously. In order to block PD-1 signaling, one day before IFN-anti-PD-L1 treatment, mice were treated intravenously with 100 μg of anti-PD-1 antibody (4H2) once every two weeks. In order to delete CD8+ T cells, one day before IFN-anti-PD-L1 treatment, 200 μg of anti-CD8 antibody (TIB210) was injected intraperitoneally. In order to block type I IFN signaling, one day before IFN-anti-PD-L1 treatment, 100 μg of anti-IFNAR1 antibody (MAR1-5A3) was injected. C57BL/6 mice were injected subcutaneously with $5\times10^5$ MC38 cells at the right side. Mice were then injected intravenously with 25 μg of IFN-anti-PD-L1 twice. The tumor volume was measured twice a week and calculated by (length×width×height/2). In order to block lymphocyte transport, mice were injected intraperitoneally with 25 μg of FTY720 and then 20 μg of FTY720 was given every other day to maintain the blocking.

Detection of Tumor Antigen-Specific T Cells by ELISPOT

Lymph nodes (LNs) or spleens were isolated from tumor-bearing mice to prepare single cell suspensions. A single dose of 60 Gys (10 Gys/min, 6 min) was used to irradiate A20 tumor cells. Spleen cells or LN cells were co-cultivated with irradiated tumor cells for 48 h at a ratio of 4:1. According to the operational plan of the manufacturer (BD Biosciences), IFN-γ production was measured with an IFN-γELISPOT assay kit. Cytokine spots were assayed with an immunospot analyzer (CTL).

In Vitro Cultivation and Functional Analysis

A tumor tissue was collected, cut into small pieces, and suspended in a digestion buffer (RPMI-1640 medium with 1 mg/mL collagenase IV and 100 μg/mL DNase I). After digestion at 37° C. for 45 min, a single cell suspension was prepared by a 70 μm cell strainer, and CD8+ T cells and DCs (MHCII+CD11c+) were sorted by FACS. T cells, DCs and irradiated tumor cells were co-cultivated in the presence of IFNα (2 ng/mL) or anti-PD-L1 antibody (10 μg/mL) at a ratio of 10:1:2.5. Three days later, the supernatant was collected, and the IFN-γ level was determined by CBA.

Statistical Analysis

Data were shown as mean±SEM. Unpaired Student's two-tailed t test was used for comparative statistical analysis. GraphPad Prism version 5.0 (GraphPad Software) was used for analysis. *,  and * were used to indicate the statistically significant differences of $p<0.05$, $p<0.01$ and $p<0.001$, respectively.

Figure 1B:
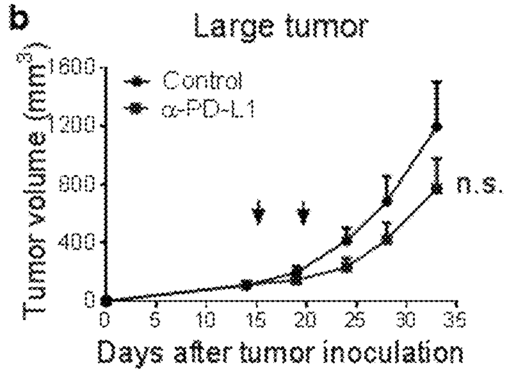
Figure 1C:
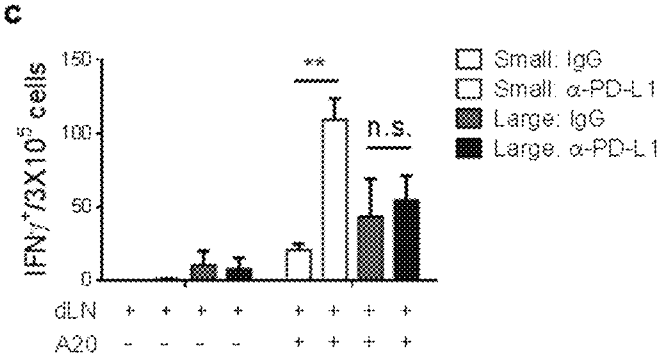

Example 1: Topical Administration of Type I IFN Overcomes the Resistance of Tumor to PD-1/PD-L1 Blockade Therapy A recent study showed that the clinical response of a patient to immune checkpoint blockade was related to the T cell activation and tumor burden. Consistent with that, the present invention found that the anti-PD-L1 antibody exhibited effective tumor control in small A20 tumors (<50 $mm^3$) (FIG. 1A). On the contrary, when the tumor became larger (>100 $mm^3$), the anti-tumor effect was significantly reduced (FIG. 1B). Advanced tumors may have formed a variety of mechanisms to suppress the anti-tumor immune response. In fact, when comparing the T cell activation in small tumors with the T cell activation in large tumors, it was observed that PD-L1 blockade induced strong T cell activation in small tumors, and the same treatment resulted in limited effect on T cells in advanced tumors (FIG. 1C). The data implied that the insufficient T cell activation may be caused by ineffective response of advanced tumors to immune checkpoint blockade.

Figure 1D:
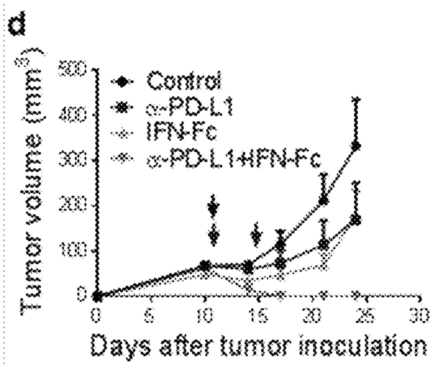
Figure 1E:
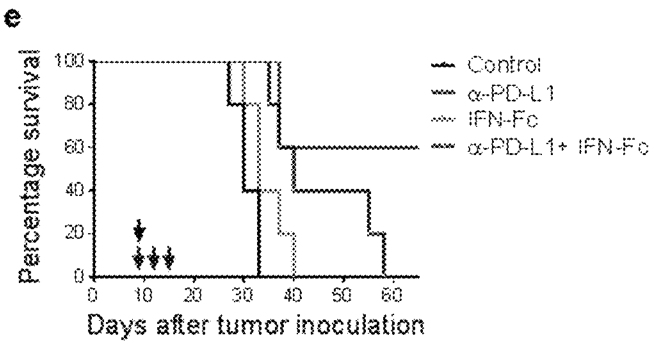
Figure 1F:
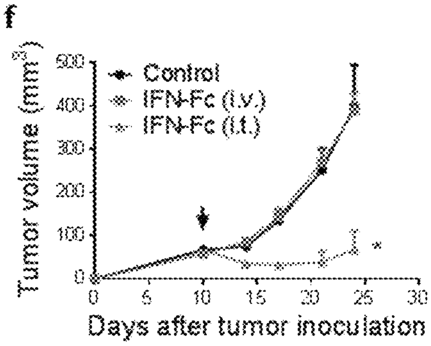

In order to verify this hypothesis, experiments were designed to explore whether providing type I IFN (a powerful cytokine that enhances cross-presentation to cytotoxic T cells) can improve the PD-1/PD-L1 blockade therapy. Advanced tumors were treated with the combination therapy of PD-L1 blockade and IFNα. Neither anti-PD-L1 antibody nor IFNα (IFNα4) alone was unable to control tumors, and all tumors eventually progressed (FIG. 1D). Impressively, the combination therapy induced a stronger anti-tumor effect, leading to complete tumor elimination in all treated mice (FIG. 1D). A similar synergistic effect was found in another tumor model MC38 (FIG. 1E). Type I IFN signals acted locally in TME, because intratumoral delivery of IFNα effectively controlled the tumor growth (FIG. 1F). In contrast, when IFN was delivered systemically, these effects disappeared completely.

In summary, the above data indicate that type I IFN and PD-1/PD-L1 blockade have a synergistic effect and can control advanced tumors. This also indicates that IFN needs to target TME to achieve optimized anti-tumor effects.

Example 2: Construction of IFN-Anti-PD-L1 Fusion Protein for Specific Delivery of IFN to Tumor Tissues Topical administration of IFN to tumors cannot be implemented for most patients. In addition, systemic delivery of type I IFN usually leads to limited anti-tumor activity and severe side effects. Targeting antibodies with cytokines have proven to be an effective strategy for topical delivery of immunomodulatory molecules. However, it is quite difficult to identify tumor-specific molecules for therapeutic targeting. It has been reported that PD-L1 is highly expressed in tumor tissues. Recent studies have shown that anti-PD-L1 antibodies specifically accumulate in PD-L1-positive tumor tissues. Moreover, in addition to the anti-tumor function, IFNs can powerfully induce the expression of PD-L1, thus inhibiting the response of T cells to tumors. In order to overcome this counteracting effect and realize the mutual promotion for immune (re)activation is TME, the present invention proposes to use an IFN and anti-PD-L1 antibody to construct a fusion protein IFN-anti-PD-L1, which can further up-regulate the expression of PD-L1 in tumor tissues, thereby leading to increased accumulation of antibodies.

Figure 2A:
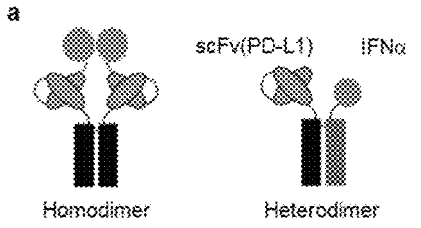
FIGS. 2A-2I illustrate the construction and properties of the IFN-anti-PD-L1 fusion protein.
Figure 2B:
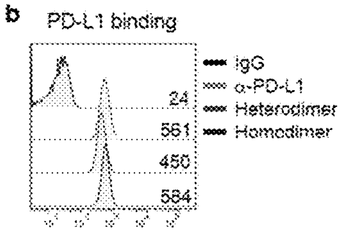
Figure 2C:
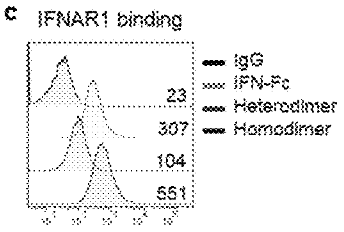

In the present invention, in order to verify this hypothesis, a fusion protein with anti-PD-L1 antibody scFv [scFv (PD-L1)] and IFNα was produced in the form of homodimer or heterodimer (FIG. 2A). In order to evaluate the obtained IFN-anti-PD-L1 fusion protein (using IFN-α4), its affinity with PD-L1 or IFN-α receptor 1 (IFNAR1) was determined. A20 cells were positive for both PD-L1 and IFN receptors. Therefore, one receptor was knocked out from A20 cells, and the binding of the fusion protein to another receptor was determined. In $IFNAR1^{-/-}$ A20 cells expressing PD-L1, the fusion protein exhibited similar affinity to anti-PD-L1 antibodies (FIG. 2B). In $PD\text{-}L1^{-/-}$ A20 cells expressing IFNAR, the heterodimer exhibited reduced binding compared with IFN-Fc or the homodimer (FIG. 2C).

TABLE 1

Protein binding data of the Example 2.

| Group | IgG (control) | Anti-PD-L1 | IFN-Fc | IFN-anti-PD-L1 heterodimer | IFN-anti-PD-L1 homodimer |
|---|---|---|---|---|---|
| $IFNAR1^{-/-}$ A20 | – | ++ | – | ++ | ++ |
| $PD\text{-}L1^{-/-}$ A20 | – | – | ++ | + | ++ |

Notes:
"+" means binding strength,
"–" means no binding,
and blank space means no experiment.

Figure 2D:
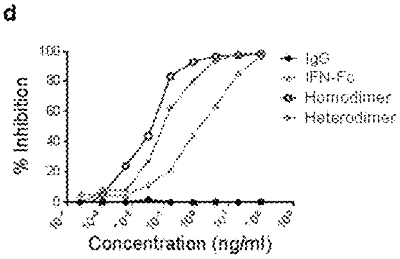

The fusion protein effectively protected L929 cells from VSV infection, indicating that the antiviral activity of IFN remained unchanged (FIG. 2D).

In summary, these data indicate that the fusion protein IFN-anti-PD-L1 in the form of homodimer or heterodimer can bind to PD-L1 while remaining the effective biological activity of IFN.

Figure 2E:
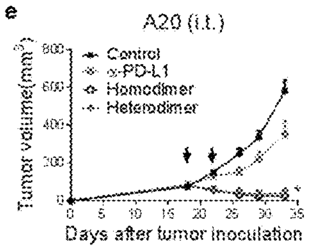

Example 3: Targeted Delivery of IFN Through Anti-PD-L1 to Control Advanced Tumors In view of the potent activity of IFN-anti-PD-L1 (IFN-α4) fusion protein in vitro, further studies were conducted to explore whether the fusion protein can control the tumor growth in vivo. Mice with advanced A20 tumors were treated with the fusion protein (i.t). Although anti-PD-L1 antibodies failed to control the tumor growth, the IFN-anti-PD-L1 fusion protein in the form of homodimer or heterodimer overcame the anti-PD-L1 resistance and induced complete tumor regression (FIG. 2E) in most treated mice.

Figure 2F:
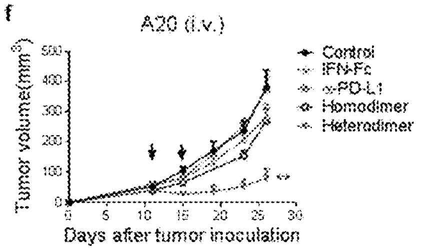
Figure 2G:
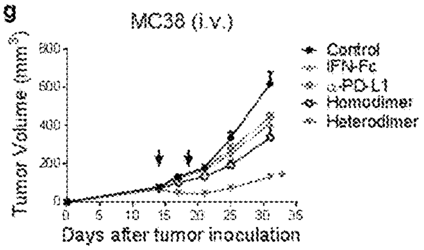
Figure 2H:
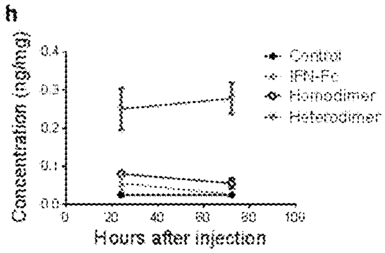
Figure 2I:
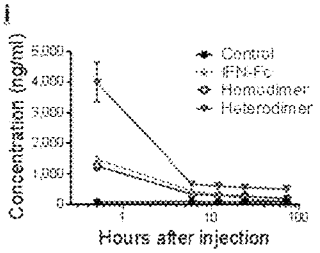

In order to test the targeting effect of the fusion protein, A20 tumor-bearing mice were systematically treated with the fusion protein. Surprisingly, although the homodimer exhibited a higher binding affinity to IFN receptors and a higher antiviral activity in vitro (FIG. 2C and FIG. 2D), only the heterodimer instead of the homodimer could effectively inhibit the tumor growth (FIG. 2F) when delivered in vivo. A similar effect was observed in the MC38 model (FIG. 2G). We want to know whether this difference is due to the different dynamics in vivo. Further experimental results showed that compared with the homodimer, the heterodimer had a higher accumulation level in tumor tissues (FIG. 2H). In addition, the serum half-life of the heterodimer increased significantly (FIG. 2I). These data also indicate that the heterodimer has a better anti-tumor effect, and also mean that the heterodimer is a preferred candidate for in vivo studies.

In summary, these data show that targeted delivery of IFN by anti-PD-L1 antibodies can induce effective anti-tumor effects, resulting in improved tumor control.

Figure 3A:
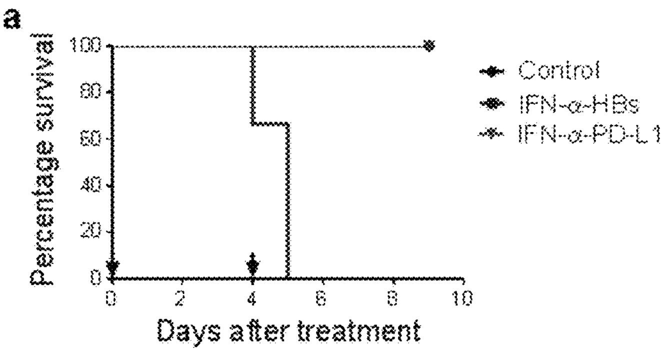
FIGS. 3A-3I illustrates that the IFN-anti-PD-L1 fusion protein has less toxic and side effects and excellent anti-tumor effect in vivo.
Figure 3B:
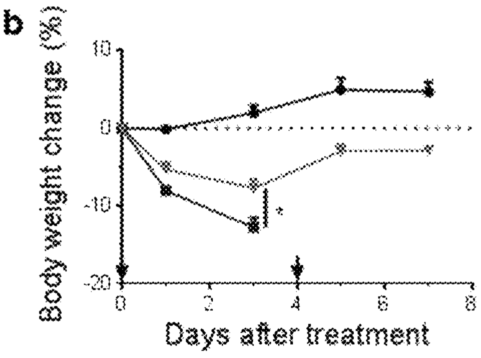
Figure 3C:
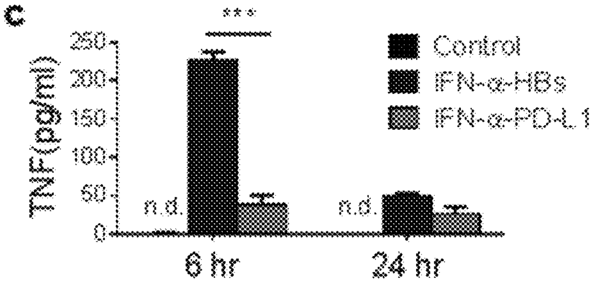
Figure 7A:
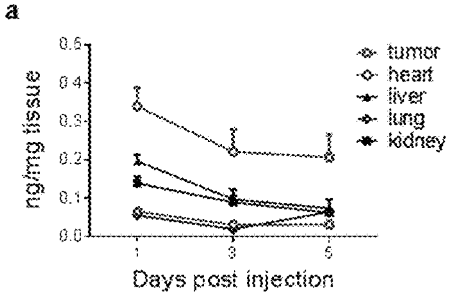
FIGS. 7A-7D illustrate that the IFN-anti-PD-L1 heterodimer specifically targets tumor tissues and induces less toxicity.
Figure 7B:
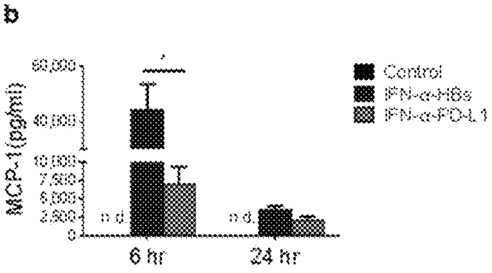
Figure 7C:
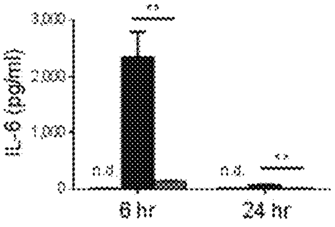
Figure 7D:
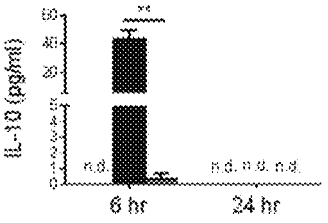
Figure 8A:
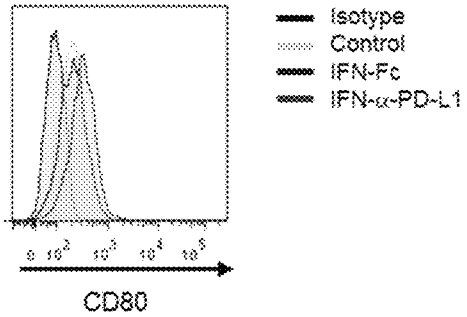
FIGS. 8A-8B illustrate that IFN-anti-PD-L1 up-regulates the expression of CD80 in tumor-infiltrating DCs. 2 days after the IFN-anti-PD-L1 treatment, MC38 tumor tissues are isolated. FCM is used to detect the expression of CD80 in tumor-infiltrating DCs (CD11c+MHCII+).
Figure 8B:
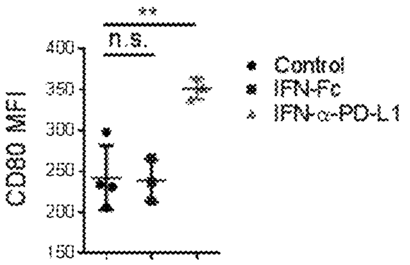

Example 4: Tumor-Targeted IFN-Anti-PD-L1 Shows Less Toxicity and Strong Anti-Tumor Activity The application of type I IFN is limited due to severe side effects during systemic delivery. In order to test the in vivo toxicity of anti-PD-L1 antibodies with IFN (IFN-α4), the heterodimer (IFN-anti-PD-L1) or non-targeting control IFN-anti-HBs (anti-Hepatitis B virus (HBV) surface protein) fusion protein was adopted at a high dose. After the second injection of IFN-anti-HBs, tumor-bearing mice experienced severe weight loss, activity reduction and fur wrinkling, and all died within one day (FIG. 3A). In contrast, none of the mice treated with IFN-anti-PD-L1 died, and these mice recovered after mild weight loss (FIG. 3A and FIG. 3B). The IFN-anti-PD-L1 fusion protein accumulated in tumors but not in normal tissues (FIG. 7A).

In order to better evaluate the side effects, the cytokine level in serum was determined after the first injection. Impressively, non-targeting IFN-anti-HBs induced high expression of inflammatory cytokines TNF, IFN, MCP-1, IL-6, IL-10 and the like (FIGS. 3C and 3H, and FIGS. 7B-7D).

Figure 3D:
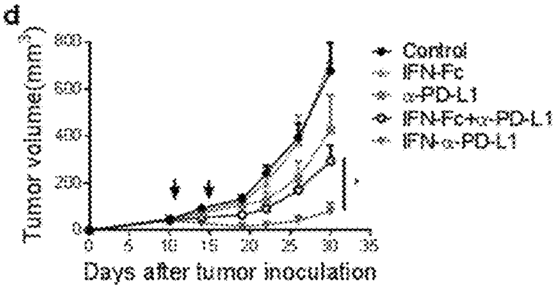
Figure 3H:
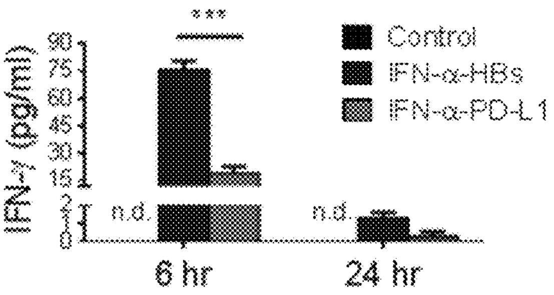

Tumor-specific targeting is essential for the anti-tumor effect of the fusion protein because a simple mixture of IFN-Fc and an anti-PD-L1 antibody does not produce a synergistic effect like that generated by the IFN-anti-PD-L1 fusion protein (FIG. 3D).

In summary, these data show that IFN-anti-PD-L1 can target tumor tissues to inhibit the tumor growth, and has less toxicity and side effects.

Example 5: IFN-Anti-PD-L1 Up-Regulates PD-L1 and IFNAR Receptors in TME

Figure 3E:
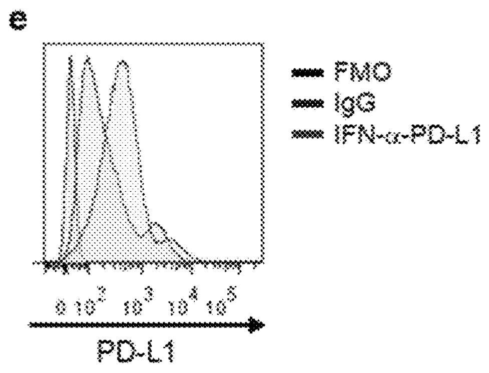
Figure 3I:
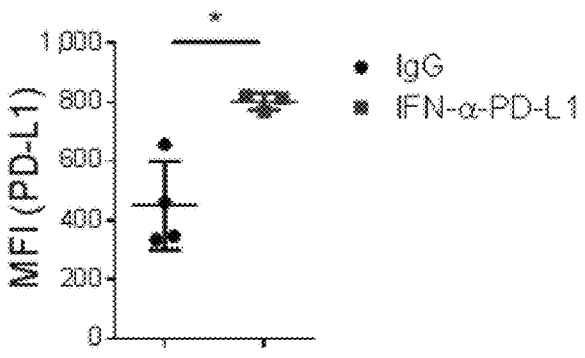
Figure 3F:
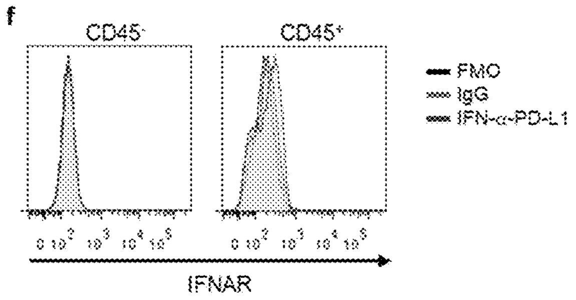
Figure 3G:
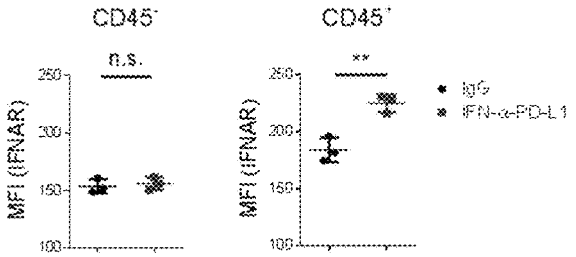

Since type I IFN is the most effective cytokine for inducing PD-L1 expression, the PD-L1 level in TME was determined after systemic treatment with IFN-anti-PD-L1 (IFN-α4 heterodimer). IFN-anti-PD-L1 significantly increased the expression of PD-L1 in tumor tissues (FIGS. 3E and 3I). Increased PD-L1 expression could enhance the tumor-specific accumulation of the fusion protein. Interestingly, the level of IFN receptors in $CD45^+$ cells (leukocytes) also increased (FIGS. 3F-3G), making the cells more sensitive to IFN treatment. In summary, data show that IFN-anti-PD-L1 leads to multiple feedforward responses, which may further enhance tumor-targeted and anti-tumor effects.

Figure 4A:
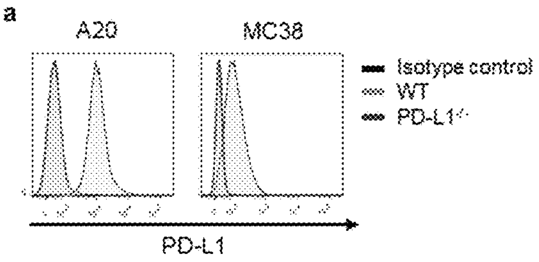
FIGS. 4A-4G illustrate that PD-L1 expressed in the host or tumor cells can effectively mediate the anti-tumor effect of the IFN-anti-PD-L1 fusion protein.

Example 6: PD-L1 in Tumor Cells is not Necessary for the Anti-Tumor Effect of the IFN Fusion Protein Many tumor cells overexpress PD-L1 as a strategy to evade immune response. PD-L1 can be further induced by inflammatory cytokines in many cells outside tumors. Whether PD-1/PD-L1 blockade acts on PD-L1 expressed by tumor cells or acts on PD-L1 expressed by non-tumor cells has not yet been settled. In order to determine whether PD-L1 in tumor cells is necessary for anti-PD-L1 antibodies with IFN, the present invention used the CRISPR/Cas9 technology to knock out PD-L1 from tumor cells. PD-L1 expression was completely eliminated in the A20 and MC38 tumor cells subjected to knockout (FIG. 4A). IFNs could induce the expression of PD-L1 When stimulated by IFNα, PD-L1 was up-regulated in wild-type (WT) cells, but the cells subjected to knockout still did not express PD-L1 (data were not shown).

Figure 4B:
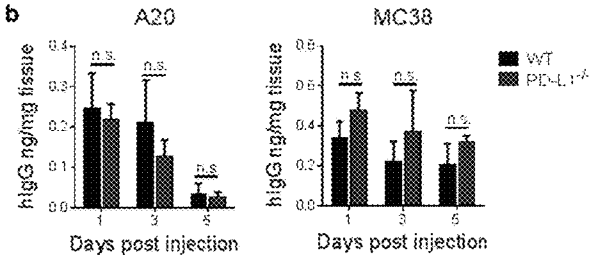
Figure 4C:
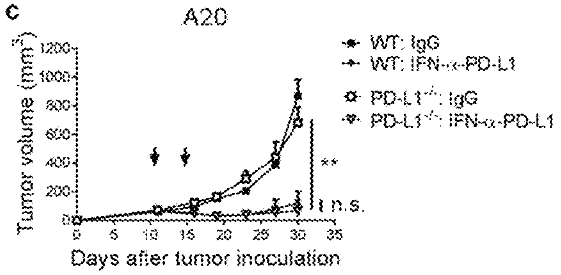
Figure 4D:
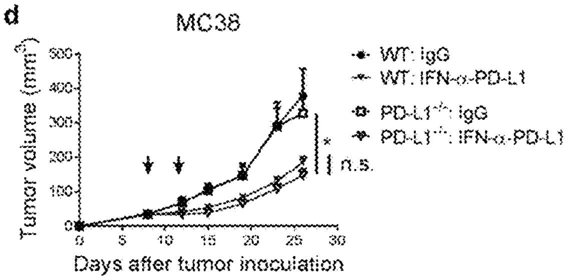

To test whether PD-L1 on tumor cells is necessary for targeting, the fusion protein IFN-anti-PD-L1 (IFN-α4 heterodimer) was used to treat WT or PD-L1-knockout (PD-$L1^{-/-}$) tumor-bearing mice. Protein levels in tumor tissues were measured. To our surprise, the fusion protein accumulated in tumor tissues regardless of whether the tumor cells express PD-L1 (FIG. 4B). When using IFN-anti-PD-L1 to treat tumors, both PD-1-knockout tumors and WT tumors were able to be effectively controlled (FIG. 4C and FIG. 4D). These data indicated that PD-L1 in tumor cells was not necessary for the anti-tumor effect.

Figure 4E:
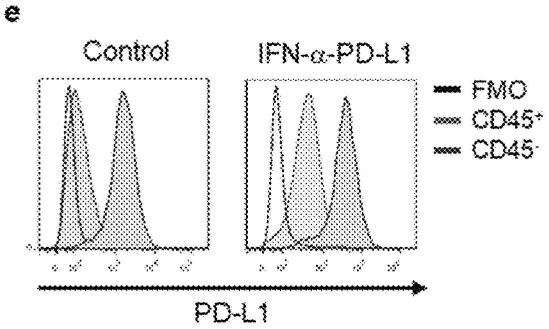
Figure 4G:
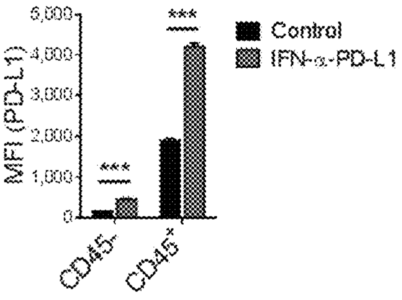
Figure 4F:
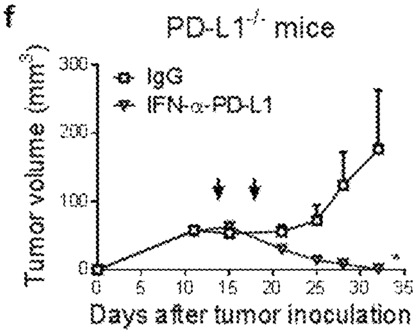

The previous data showed that IFN-anti-PD-L1 created a feedforward loop to up-regulate the expression of PD-L1 in TME (FIGS. 3E and 3I). Since both tumor and stromal cells can express PD-L1, the expression levels of PD-L1 in different cell subgroups in tumor tissues were detected. IFN-anti-PD-L1 treatment significantly up-regulated PD-L1 expression in tumor and stromal cells (FIGS. 4E and 4G). Since PD-L1 in tumor cells is not necessary, we want to know whether PD-L1 is necessary in host cells. Interestingly, IFN-anti-PD-L1 well controlled the tumor growth in PD-L1-deficient mice (FIG. 4F). In summary, these data indicate that PD-L1 expressed in host cells or tumor cells is sufficient to mediate the tumor-targeted and anti-tumor effects of the fusion protein.

Example 7: IFN-Anti-PD-L1 Fusion Protein Promotes the Activation of APC and T Cells TME Next, it was investigated whether type I IFN signaling is necessary for anti-tumor effects. Mice were treated with an anti-IFNAR blocking antibody during treatment with the IFN-anti-PD-L1 fusion protein (heterodimer). The anti-IFNAR antibody completely eliminated the anti-tumor effect of the fusion protein, suggesting the important role of type I IFN signaling (FIG. 5).

Figure 5A:
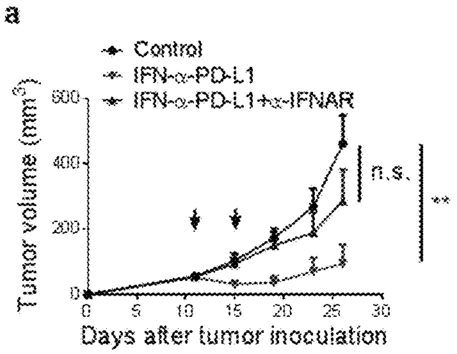
FIGS. 5A-5G illustrate that IFNAR expressed by host cells is essential for tumor control.
Figure 5B:
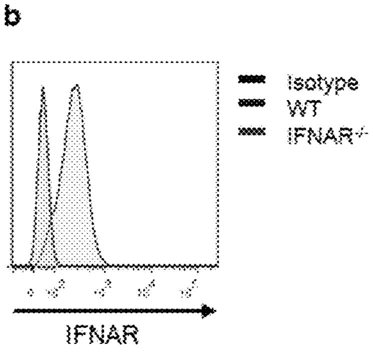
Figure 5C:
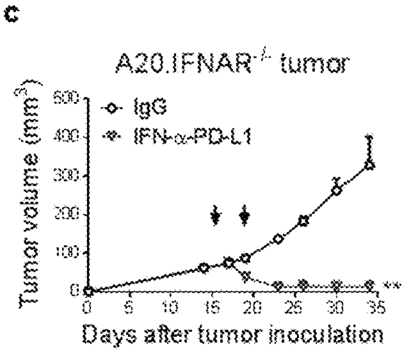

IFNAR was expressed in both tumor and host cells. To detect whether IFN receptors in tumor cells are necessary. IFNAR1 was knocked out from tumor cells (FIG. 5B). Interestingly, IFN-anti-PD-L1 effectively controlled the tumor growth in mice carrying A20.$IFNAR1^{-/-}$ tumors (FIG. 5C).

Figure 5D:
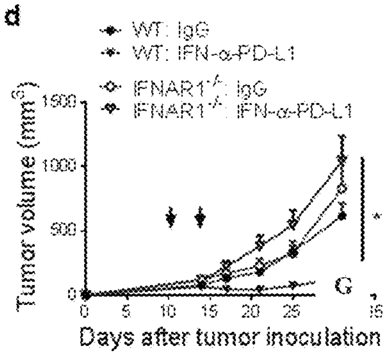

Since IFN receptors in tumor cells are not necessary, we investigated whether the receptors expressed on host cells are necessary. MC38 tumors were inoculated into WT or IFNAR$^{-/-}$ mice, and then the mice were treated with the fusion protein. It was observed in the experiment that the anti-tumor effect disappeared in deficient mice, suggesting that IFN receptors played a more important role in the host (FIG. 5D).

Figure 5E:
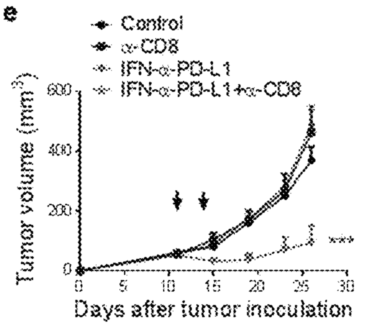
Figure 5F:
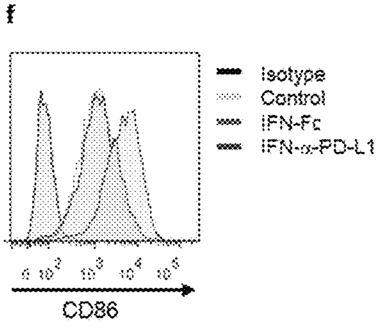
Figure 5G:
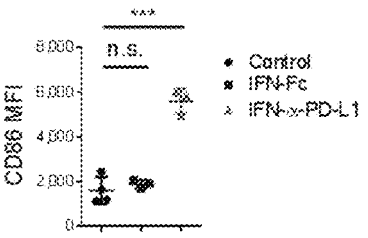

CD8+ T cells are necessary for anti-tumor effects. When CD8+ T cells are blocked with an anti-CD8 antibody, the anti-tumor effect is completely eliminated (FIG. 5E). Previous studies have shown that type I IFN can enhance DC cross-presentation in TME, leading to better T cell activation. In fact, IFN-anti-PD-L1 treatment increased the expression of CD86 and CD80, which are marker molecules for DC activation (FIGS. 5F-5G and FIGS. 8A-8B). As a control, no significant activation of DC was observed in tumors treated with IFN-Fc, indicating the important role of tumor-specific targeting.

In summary, these data indicate that the IFN fusion protein mediates the anti-tumor effect mainly through IFN signaling in host cells.

Figure 6A:
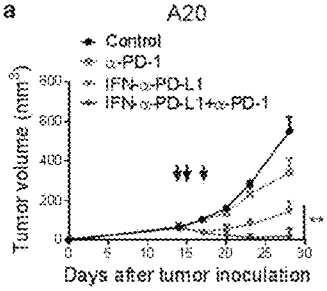
FIGS. 6A-6G illustrate that PD-1 blockade further ensures that IFN-anti-PD-L1 induces a feedforward anti-tumor response.

Example 8: Targeted Delivery of IFN Through an Anti-PD-L1 Antibody Overcomes the Resistance of Tumors to PD-1 Blocking Therapy Advanced tumors were often resistant to PD-1/PD-L1 blocking therapy. In fact, neither anti-PD-1 antibody therapy nor anti-PD-L1 antibody therapy could control the growth of advanced A20 tumors (FIG. 6A). Compared with PD-1/PD-L1 blockade, the IFN-anti-PD-L1 fusion protein (IFN-α4 heterodimer) showed a better anti-tumor effect. However, some tumors eventually relapsed after being initially controlled (FIG. 2F to FIG. 2G). The overexpression of PD-L1 after immunotherapy may further limit the T cell-mediated tumor control. Therefore, it was assumed that the combination therapy of anti-PD-1 antibody and IFN-anti-PD-L1 can overcome the resistance of tumors to IFN or PD-1/PD-L1 blocking therapy. In fact, the combination therapy resulted in better tumor control, and advanced tumors almost completely regressed (FIG. 6A).

Figure 6B:
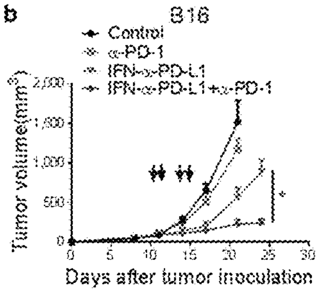

B16F10 melanoma is a well-known mouse tumor model that is resistant to PD-1/PD-L1 blocking therapy. Consistent with previous reports, PD-1/PD-L1 blockade exhibited no effect on tumor growth in the B16F10 model (FIG. 6B). IFN-anti-PD-L1 treatment only partially controlled the tumor. Interestingly, the combination therapy of IFN-anti-PD-L1 and PD-1 blockade significantly improved the anti-tumor effect.

Figure 6C:
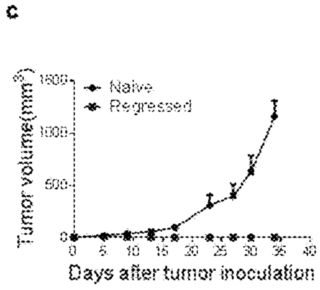

To test whether the anti-tumor response mediated by IFN-anti-PD-L1 leads to prolonged protective T cell immunity, a lethal dose of A20 cells was again inoculated into mice that experienced complete tumor regression after the combination therapy. All mice resisted the re-attack of tumor cells, confirming that the fusion protein induced a memory adaptive immune response (FIG. 6C).

Figure 6D:
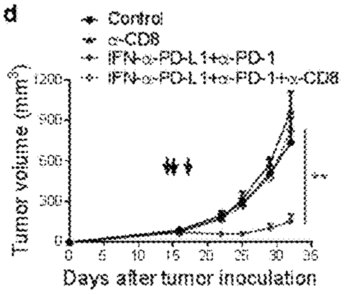
Figure 6E:
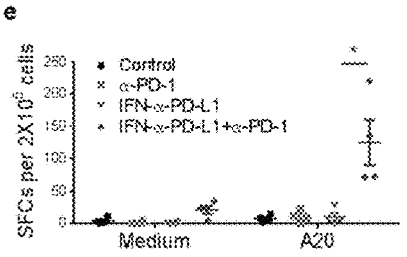
Figure 9A:
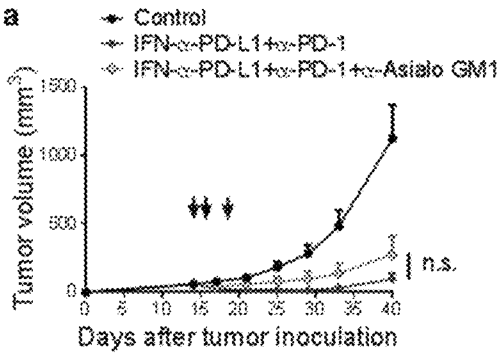
FIGS. 9A-9C illustrate that NK and CD4+ T cells exhibit no significant effect in the anti-tumor response mediated by the combination therapy of anti-PD-1 antibody and IFN-anti-PD-L1. A20 tumor-bearing mice (n=4 to 5) are treated as described in FIG. 6A.
Figure 9B:
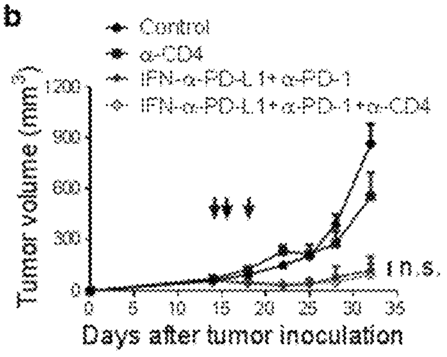
Figure 9C:
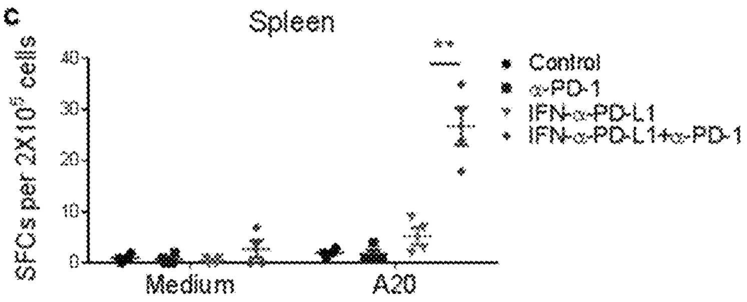
Figure 10:
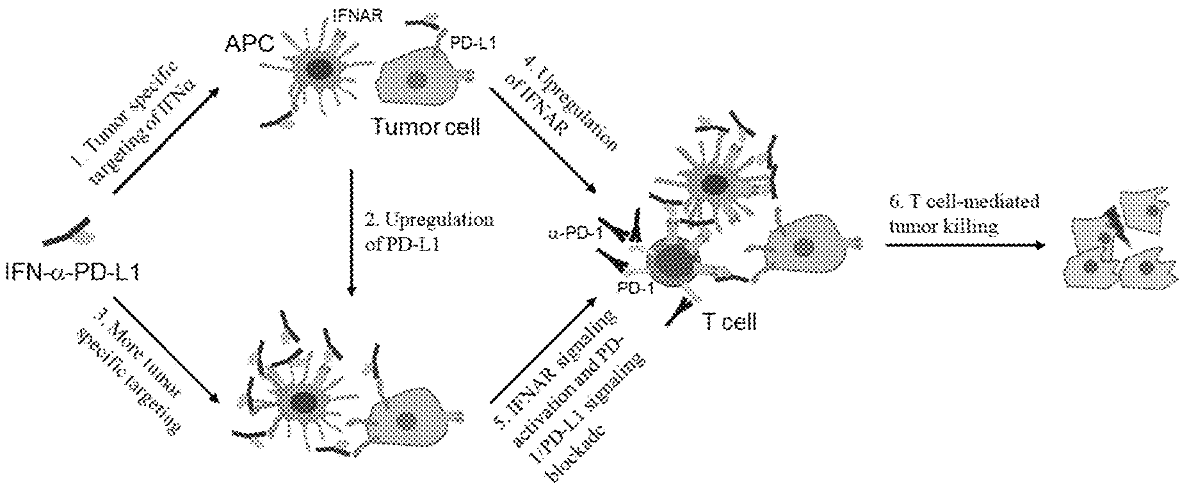
FIG. 10 illustrates a schematic mode of the anti-tumor effect mediated by an anti-PD-L1 antibody with IFN (IFN-anti-PD-L1). Anti-PD-L1 specifically delivers IFN to tumor tissues (1). IFN-mediated up-regulation of PD-L1 enhances the tumor-specific targeting (2 and 3). The antibody blocks the PD-L1/PD-1 signaling pathway to release immune braking signals (3). In addition, IFN-anti-PD-L1 up-regulates the expression of IFNAR (4), which makes tumors more sensitive to treatment (5). In summary, these factors lead to the (re)activation T of cell responses to control the tumor growth (6).

To determine which cell population or populations are required for the combination therapy, mice that experienced the combination therapy were treated with an anti-NK, CD4+ or CD8+ T cell antibody for deletion. In the absence of CD8+ T cells, the anti-tumor effect disappeared completely (FIG. 6D). In contrast, the deletion of NK or CD4+ T cells resulted in a limited effect (FIG. 9A and FIG. 9B). In order to detect whether tumor-specific T cells are produced after the treatment, cells were isolated from LN or spleen tissues and then co-cultivated with irradiated A20 tumor cells. The IFN-αELISPOT assay was conducted to assess the tumor-specific T cell response. PD-1/PD-L1 blockade alone showed a limited effect on T cell activation (FIG. 6E and FIG. 9C). In contrast, IFN-anti-PD-L1 (IFN-α4 heterodimer) induced a better response. Importantly, the combination therapy of IFN-anti-PD-L1 and PD-1 blockade significantly increased the number of tumor-specific T cells (FIG. 6E and FIG. 9C).

Figure 6F:
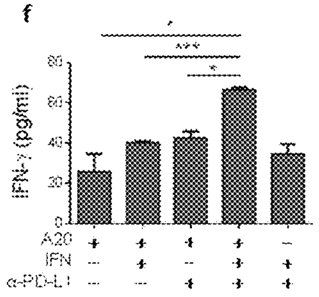

To test IFN, PD-L1 and tumor cells in an established in vitro system, TME could be better reproduced, and DC and T cells were isolated from tumors established in vivo. Cells were cultivated for three days in the presence of IFN, anti-PD-L1 antibody, or a combination of the two. Although monotherapy showed a limited effect, the combination therapy of IFN and anti-PD-L1 antibody significantly increased the production of IFNγ by T cells (FIG. 6F).

In summary, these data indicate that the combination of IFN and PD-1/PD-L1 blockade coordinately induces a strong tumor-specific T cell response, which can overcome the resistance of tumors to immune checkpoint blockade in advanced tumors.

Figure 6G:
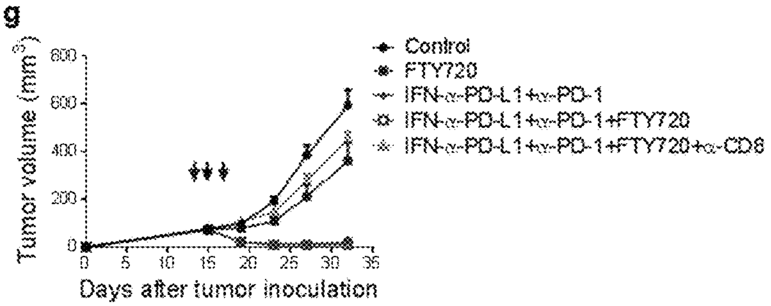

Example 9: Targeted Delivery of IFN Activates Tumor-Resident T Cells for Tumor Control Data show that tumor-specific T cells play an important role in the anti-tumor immune response. These T cells may mainly come from two sources. Some are T cells that are already present in the tumor tissue, while others are newly-activated T cells that migrate from the periphery to the tumor tissue. IFN can not only stimulate DC to activate TIL, but also increase chemokines that attract T cells. To test which T cell populations are necessary, FTY720 was used to block the transport of peripheral lymphocytes to tumor tissues. Interestingly, even when lymphocyte transport was blocked, similar to the control group, the combination treatment with IFN and PD-1/PD-L1 blockade could also control tumors (FIG. 6G). These data showed that reactivation of pre-existing T cells by IFN-anti-PD-L1 (IFN-α4 heterodimer) was sufficient for tumor control. Consistently, the topical deletion of CD8$^{+}$ T cells reduced all anti-tumor effects (FIG. 6G). In summary, these data indicate that PD-L1 blockade can reverse the T-cell depletion state, and IFN effectively reactivates the partially-recovered resident T cells for tumor control.

Example 10: Construction of IFNα Mutants with Reduced Affinity

Site-directed mutations were conducted at the known key amino acid sites of IFNα that bind to the receptor IFNAR. Specific mutation sites were shown in FIG. 11. IFNα mutants with reduced affinity were screened. The amino acid sequences and coding nucleic acid sequences of the IFNα mutants were shown in SEQ ID NOS: 25 to 36 in the sequence list of the specification (as summarized in Table 2).

TABLE 2

| Name | Amino acid sequence | Coding nucleic acid sequence |
|---|---|---|
| Mouse IFNα4 (L30A) | SEQ ID NO: 25 | SEQ ID NO: 26 |
| Mouse IFNα4 (R144 A) | SEQ ID NO: 27 | SEQ ID NO: 28 |
| Mouse IFNα4 (A1456) | SEQ ID NO: 29 | SEQ ID NO: 30 |
| Mouse IFNα4 (R149A) | SEQ ID NO: 31 | SEQ ID NO: 32 |
| Mouse IFNα4 (S152A) | SEQ ID NO: 33 | SEQ ID NO: 34 |
| human IFNα2 (Q124R) | SEQ ID NO: 35 | SEQ ID NO: 36 |

Example 11: Activity Assay for IFNα-Fc Mutants

The biological activity was assayed for IFNα-Fc mutants by the antiviral infection bioassays. Before infected with VSV-GFP viruses, L929 cells were mixed with each protein and then cultivated overnight. After the cells were cultivated for 30 h, the percentage of virus-infected cells was determined by FCM, and the inhibition rates and $EC_{50}$ values of different concentrations of protein on cell infection were calculated (FIGS. 12A-12B). Results show that the constructed mutants all exhibit a certain decrease in activity, and the two mutants R144A and A145G have the weakest activity and are potential preferred targets.

Example 12: In Vitro Targeting Test of Mutant IFN-Anti-PD-L1

WT PD-L1$^+$ A20 cells and PD-L1$^{-/-}$ A20 cells were adopted, and the proliferation was detected by a CCK8 kit for cells treated with different concentrations of protein. The results showed that, compared with the WT fusion protein, the mutant IFN-anti-PD-L1 exhibited a lower $EC_{50}$ value for inhibiting the proliferation of targeting-deficient PD-L1$^{-/-}$ A20 cells. On PD-L1$^{+/+}$ A20 cells with targetability, the mutant IFN-anti-PD-L1 and WT fusion protein exhibited no significant difference in terms of $EC_{50}$ for the inhibition on cell proliferation (FIGS. 13A-3D). In the mutant IFN-anti-PD-L1 fusion protein, the first polypeptide, Anti-PD-L1 (ScFv(PD-L1)-Fc), had an amino acid sequence shown in SEQ ID NO: 1, and the second polypeptide, mutant mIFNα4-Fc, had an amino acid sequence shown in Table 3 below.

TABLE 3

| Name | Amino acid sequence | Coding nucleic acid sequence |
|---|---|---|
| mIFN-α4 (L30A)-Fc | SEQ ID NO: 37 | SEQ ID NO: 38 |
| mIFN-α4 (R144A)-Fc | SEQ ID NO: 39 | SEQ ID NO: 40 |
| mIFN-α4 (A145G)-Fc | SEQ ID NO: 41 | SEQ ID NO: 42 |
| mIFN-α4 (R149A)-Fc | SEQ ID NO: 43 | SEQ ID NO: 44 |
| mIFN-α4 (S152A)-Fc | SEQ ID NO: 45 | SEQ ID NO: 46 |
| mIFN-α2 (Q124R)-Fc | SEQ ID NO: 47 | SEQ ID NO: 48 |

The ratio of $EC_{50}$ in PD-L1$^{-/-}$ A20 cells to $EC_{50}$ in PD-L1$^{+/+}$ A20 cells can reflect the targetability of this bispecific protein. It can be found from the normalization of the ratio with the data of wt-mIFNa4-Fc that R144A and A145G are the two with the optimal targetability, suggesting that these two mutant fusion proteins can more specifically target PD-L1-positive target cells, while avoiding the induction of IFNAR signaling pathway activation on other cells.

After being fused with the targeting protein, the IFNα mutant with reduced activity can induce IFNAR activation only on target cells. Peripheral off-target is avoided when IFN is used. The mutant IFN-anti-PD-L1 constructed in the present invention has greater potential for treating tumors.

The above descriptions are merely preferred examples of the present invention, and are not intended to limit the present invention. Any modifications, equivalent replacements, improvements, and the like made within the spirit and principle of the present invention shall be all included in the protection scope of the present invention.

What is claimed is:

1. A fusion protein, wherein, the fusion protein is IFN-anti-PD-L1 formed by fusion of an interferon (IFN) and a PD-L1 binding protein and the fusion protein is a heterodimer protein, the fusion protein comprises a first polypeptide and a second polypeptide, wherein the first polypeptide and the second polypeptide are different, and the first polypeptide comprises the amino acid sequence as set forth in SEQ ID NO: 1, and the second polypeptide comprises an Ig Fc region and an IFN located at a N-terminus of the Ig Fc region, wherein, an Fc region in the first polypeptide and the Ig Fc region in the second polypeptide are Igs of the same subtype and, wherein the IFN is selected from the group consisting of a type I IFN, a type I IFN mutant, a type II IFN and a type III IFN, wherein the type III IFN is IFN-α, IFN-β, IFN-γ, IFN-λ1 (IL-29), IFN-λ2 (IL-28a), IFN-λ (IL-28b) or IFN-ω; and the IFN is derived from human or mice.

2. The fusion protein according to claim 1, wherein the type I IFN is IFN-α4 comprising the amino acid sequence set forth in SEQ ID NO: 13, or an IFN-α4 mutant, wherein the IFN-α4 mutant is mIFN-α4 (L30A) comprising the amino acid sequence set forth in SEQ ID NO: 25, mIFN-α4 (R144A) comprising the amino acid sequence set forth in SEQ ID NO: 27, mIFN-α4 (A145G) comprising the amino acid sequence set forth in SEQ ID NO: 29, mIFN-α4 (R149A) comprising the amino acid sequence set forth in SEQ ID NO: 31, mIFN-α4 (S152A) comprising the amino acid sequence set forth in SEQ ID NO: 33, or hIFN-α2 (Q124R) comprising the amino acid sequence set forth in SEQ ID NO: 35.

3. The fusion protein according to claim 1, wherein the second polypeptide of the heterodimer protein comprises an amino acid sequence selected from the group consisting of SEQ ID NO: 2, SEQ ID NO: 37, SEQ ID NO: 39, SEQ ID NO: 41, SEQ ID NO: 43, SEQ ID NO: 45, and SEQ ID NO: 47.

4. A method for preparing a pharmaceutical composition or a kit, comprising the step of providing the fusion protein according to claim 1 in the pharmaceutical composition or the kit, wherein, the pharmaceutical composition or the kit is for treating tumor, and PD-1/PD-L1 blockade alone is ineffective against the tumor.

5. A pharmaceutical preparation, a pharmaceutical composition or a kit, wherein the pharmaceutical preparation, the pharmaceutical composition or the kit comprises the fusion protein according to claim 1.

6. A method for treating a tumor, comprising the step of administering to a patient with a tumor the fusion protein according to claim 1 and an anti-PD-1/PD-L1 antibody together.

7. The method according to claim 6, wherein the tumor is a tumor or an advanced tumor and PD-1/PD-L1 blockade alone is ineffective against the tumor.

8. The method according to claim 6, wherein a patient with the tumor suffers from diseases related to defects or disorders in transport of peripheral lymphocytes, and the peripheral lymphocytes of the patient cannot migrate to tumor tissues.

9. The method according to claim 4, wherein the type I IFN is IFN-α4 comprising the amino acid sequence set forth in SEQ ID NO: 13, or an IFN-α4 mutant, wherein the IFN-α4 mutants is mIFN-α4 (L30A) comprising the amino acid sequence set forth in SEQ ID NO: 25, mIFN-α4 (R144A) comprising the amino acid sequence set forth in SEQ ID NO: 27, mIFN-α4 (A145G) comprising the amino acid sequence set forth in SEQ ID NO: 29, mIFN-α4 (R149A) comprising the amino acid sequence set forth in SEQ ID NO: 31, mIFN-α4 (S152A) comprising the amino acid sequence set forth in SEQ ID NO: 33, or hIFN-α2 (Q124R) comprising the amino acid sequence set forth in SEQ ID NO: 35.

10. The method according to claim 4, wherein the second polypeptide of the heterodimer protein comprises an amino acid sequence selected from the group consisting of SEQ ID NO: 2, SEQ ID NO: 37, SEQ ID NO: 39, SEQ ID NO: 41, SEQ ID NO: 43, SEQ ID NO: 45, and SEQ ID NO: 47.

11. The pharmaceutical preparation, the pharmaceutical composition or the kit according to claim 5, wherein the type I IFN is IFN-α4 comprising the amino acid sequence set forth in SEQ ID NO: 13, or an IFN-α4 mutant, wherein the IFN-α4 mutants is mIFN-α4 (L30A) comprising the amino acid sequence set forth in SEQ ID NO: 25, mIFN-α4 (R144A) comprising the amino acid sequence set forth in SEQ ID NO: 27, mIFN-α4 (A145G) comprising the amino acid sequence set forth in SEQ ID NO: 29, mIFN-α4 (R149A) comprising the amino acid sequence set forth in SEQ ID NO: 31, mIFN-α4 (S152A) comprising the amino acid sequence set forth in SEQ ID NO: 33, or hIFN-α2 (Q124R) comprising the amino acid sequence set forth in SEQ ID NO: 35.

* * * * *